US012715909B2

(12) United States Patent
Amabile

(10) Patent No.: US 12,715,909 B2
(45) Date of Patent: Aug. 25, 2026

(54) INHIBITORS AND USES THEREOF

(71) Applicant: ENTHERA S.R.L., Milan (IT)

(72) Inventor: Giovanni Amabile, Milan (IT)

(73) Assignee: ENTHERA S.R.L., Milan (IT)

( * ) Notice: Subject to any disclaimer, the term of this patent is extended or adjusted under 35 U.S.C. 154(b) by 956 days.

(21) Appl. No.: 17/800,407

(22) PCT Filed: Feb. 19, 2021

(86) PCT No.: PCT/EP2021/054215
§ 371 (c)(1),
(2) Date: Aug. 17, 2022

(87) PCT Pub. No.: WO2021/165499
PCT Pub. Date: Aug. 26, 2021

(65) Prior Publication Data

US 2023/0192827 A1 Jun. 22, 2023

(30) Foreign Application Priority Data

Feb. 20, 2020 (EP) .................................... 20158553

(51) Int. Cl.
*C07K 16/18* (2006.01)
*A61P 11/00* (2006.01)
*A61P 19/04* (2006.01)

(52) U.S. Cl.
CPC .............. *C07K 16/18* (2013.01); *A61P 11/00* (2018.01); *A61P 19/04* (2018.01); *C07K 2317/21* (2013.01); *C07K 2317/24* (2013.01)

(58) Field of Classification Search
None
See application file for complete search history.

(56) References Cited

U.S. PATENT DOCUMENTS 3,773,919 A 11/1973 Boswell et al.
5,215,534 A 6/1993 De Harde et al.
6,066,464 A 5/2000 Khosravi et al.
6,428,781 B1 8/2002 Sakano et al.
6,602,684 B1 8/2003 Umana et al.
7,083,784 B2 8/2006 Dall'Acqua et al.
7,521,541 B2 4/2009 Eigenbrot et al.
8,101,396 B2 1/2012 Sabbadini et al.
8,323,962 B2 12/2012 Dall'Acqua et al.
9,248,242 B2 2/2016 Verespej et al.
9,427,531 B2 8/2016 Hourmand et al.
9,566,395 B2 2/2017 Denny et al.
10,682,391 B2 6/2020 D'Addio et al.
11,020,453 B2 6/2021 D'Addio et al.
11,786,585 B2 10/2023 Oh et al.
2003/0157108 A1 8/2003 Presta
2004/0093621 A1 5/2004 Shitara et al.
2004/0132028 A1 7/2004 Stumpp et al.
2005/0123546 A1 6/2005 Umana et al.
2015/0044209 A1 2/2015 Brodt et al.
2018/0169184 A1 6/2018 D'Addio et al.
2018/0172708 A1 6/2018 D'Addio et al.
2018/0243367 A1 8/2018 D'Addio et al.
2020/0316168 A1 10/2020 D'Addio et al.
2021/0169973 A1 6/2021 D'Addio et al.
2021/0388072 A1 12/2021 Fiorina et al.
2023/0039165 A1 2/2023 Amabile et al.
2023/0242649 A1 8/2023 Fiorina et al.

FOREIGN PATENT DOCUMENTS

CN 105504058 A 4/2016
CN 107921094 A 4/2018
CN 107921132 A 4/2018
EP 0965596 A1 12/1999
EP 3302564 B1 10/2019
EP 3632929 A1 4/2020
JP 2018-516975 A 6/2018
JP 2018-520212 A 7/2018
WO WO-9203471 A * 3/1992 ............... C07K 3/00
WO WO 1997/030087 A1 8/1997
WO WO 1997/039032 A1 10/1997
WO WO 98/029451 A1 7/1998
WO WO 1998/058964 A1 12/1998
WO WO 1999/022764 A1 5/1999
WO WO 1999/046597 A1 9/1999
WO WO 2001/053837 A1 7/2001
WO WO 2001/087238 A2 11/2001
WO WO 2002/020565 A2 3/2002
WO WO 2002/034916 A2 5/2002
WO WO 2003/011878 A2 2/2003
WO WO 2006/113880 A2 10/2006
WO WO 2007/024715 A2 3/2007
WO WO 2008/153788 A2 12/2008
WO WO 2011/133886 A2 10/2011
WO WO 2012/113900 A1 8/2012
WO WO 2013/152989 A2 10/2013
WO WO 2014/089262 A1 6/2014
WO WO 2016/193496 A1 12/2016
WO WO 2016/193497 A1 12/2016
WO WO 2018/085252 A1 5/2018
WO WO 2019/099706 A1 5/2019
WO WO 2020/070224 A1 4/2020
WO WO 2021/094620 A1 5/2021
WO WO 2021/099574 A1 5/2021
WO WO 2021/165499 A1 8/2021

OTHER PUBLICATIONS

Melone et al., J Cell Physiol. Oct. 2000;185(1):143-53. PMID: 10942528 DOI: 10.1002/1097-4652(200010)185:1<143::AID-JCP14> 3.0.CO;2-U.*

(Continued)

*Primary Examiner* — Michael Szperka
(74) *Attorney, Agent, or Firm* — FENWICK & WEST LLP

(57) ABSTRACT

The present invention relates to inhibitors of IGFBP5 and/or of at least one of its receptors, wherein said inhibitor has anti-fibrotic effect, methods for their production, pharmaceutical compositions containing said inhibitors, and uses thereof. In particular, the invention relates to antibodies or antigen binding fragments thereof that bind specifically to human IGFBP5 and/or to at least one of its receptors.

15 Claims, 2 Drawing Sheets

Specification includes a Sequence Listing.

(56) References Cited

OTHER PUBLICATIONS

Janeway et al., Immunobiology, 3rd edition, Garland Publishing Inc., 1997, pp. 3:1-3:11.*
Rudikoff et al., Proc Natl Acad Sci U S A. Mar. 1982;79(6):1979-83. doi: 10.1073/pnas.79.6.1979. PMID: 6804947.*
Edwards et al., J Mol Biol. Nov. 14, 2003;334(1):103-18. doi: 10.1016/j.jmb.2003.09.054. PMID: 14596803.*
Llyod et al., Protein Eng Des Sel. Mar. 2009;22(3):159-68. doi: 10.1093/protein/gzn058. Epub Oct. 29, 2008. PMID: 18974080.*
Goel et al., J Immunol. Dec. 15, 2004; 173(12):7358-67 PMID: 15585860 DOI: 10.4049/jimmunol.173.12.7358.*
Lescar et al., J Biol Chem. Jul. 28, 1995;270(30):18067-76. doi: 10.1074/jbc.270.30.18067. PMID: 7629116.*
Kanyavuz et al., Nat Rev Immunol. Jun. 2019;19(6):355-368. doi: 10.1038/S41577-019-0126-7. PMID: 30718829.*
Melone M A B et al, "Increased expression of IGF-binding protein-5 in Duchenne muscular dystrophy (DMD) fibroblasts correlates with the fibroblast induced downregulation of DMD myoblast growth: an in vitro analysis", *Journal of Cellular Physiology, Wiley Subscription Services, Inc, US*,vol. 185, Jan. 1, 2000 (Jan. 1, 2000), p. 143-153, abstract, p. 145, last paragraph, p. 136, 2nd paragraph, p. 148, left-hand column, 1st paragraph through p. 149, right-hand column, 1st paragraph.
M. Rita Lecca et al, "Fibrotic response in fibroblasts from congenital disorders of glycosylation", *Journal of Cellular and Molecular Medicine*, vol. 15, No. 8, Aug. 1, 2011 (Aug. 1, 2011), p. 1788-1796, Abstract, p. 1789, right-hand column, last paragraph, figure 3, p. 1794, left-hand column, 1st paragraph through right-hand column, 1st paragraph.
Seok Kwang et al, "Induction of Cellular Senescence by Insulin-like Growth Factor Binding Protein-5 through a p53-dependent Mechanism", DOI:10.2091/MBC.E07-03-0280, Sep. 5, 2007 (Sep. 5, 2007), p. 4543-4552, Retrieved from the Internet: URL:https://www.ncbi.nlm.nih.gov/pmc/articles/PMC2043568/pdf/zmk4543.pdf, Abstract, p. 4545, right-hand column, last paragraph through p. 4547, left-hand column, 1st paragraph, figures 1 and 2, p. 4549 , left-hand column, last paragraph through right-hand column, 1st paragraph.
Catherine S. Wright et al, "Cell motility in models of wounded human skin is improved by Gap27 despite raised glucose, insulin and IGFBP-5", *Experimental Cell Research*,vol. 319, No. 4, Feb. 1, 2013 (Feb. 1, 2013), p. 390-401, DOI: 10.1016/j.yexcr.2012.12.013, ISSN:0014-4827, Abstract, p. 391, left-hand column, paragraph 2; p. 393, right-hand column, paragraph 2 , figure 2, figure 3, p. 398, right-hand column, paragraph 3.
PCT International Search Report and Written Opinion, International Application No. PCT/EP2021/054215, dated Apr. 19, 2021, 11 pages.
Abdiche, Y.N. et al., "Exploring blocking assays using Octet, ProteOn, and Biacore biosensors," Analytical Biochemistry, Mar. 2009, vol. 386, No. 2, pp. 172-180.
Alper, C.A. et al., "Incomplete penetrance of susceptibility genes for MHC-determined immunoglobin deficiencies in monozygotic twins discordant for type 1 diabetes," *Journal of Autoimmunity*, 2006, vol. 27, pp. 89-95.
Angal, S. et al., "A single amino acid substitution abolishes the heterogeneity of chimeric mouse/human (IgG4) antibody," *Molecular Immunology*, 1993, vol. 30, No. 1, pp. 105-108.
Atkinson, M.A. et al., "Current concepts on the pathogenesis of type 1 diabetes—considerations for attempts to prevent and reverse the disease," Diabetes Care, 2015, vol. 38, pp. 979-988.
Atkinson, M.A. et al., "Does the gut microbiata have a role in type 1 diabetes? Early evidence from humans and animal models of the disease," Diabetologia, 2012, vol. 55, pp. 2868-2877.
Atkinson, M.A. et al., "Type 1 diabetes," Lancet, 2013, vol. 383, pp. 69-82.
Barker, N., "Adult intestinal stem cells: critical drivers of epithelial homeostasis and regeneration," Nat Rev Mol Cell Biol, 2014, vol. 15, pp. 19-33.
Bartfeld, S. et al., "In Vitro Expansion of Human Gastric Epithelial Stem Cells and Their Responses to Bacterial Infection," Gastroenterology, 2015, vol. 148, pp. 126-136.
Baxter, R., "Igf binding proteins in cancer: mechanistic and clinical insights," Nature Reviews, 2014, vol. 14, pp. 329-341.
Baxter, R.C., "Insulin-like growth factor binding protein-3 (IGFBP-3): Novel ligands mediate unexpected functions," J Cell Commun Signal, 2013, vol. 7, pp. 179-189.
Beck, A. et al., "Strategies and challenges for the next generation of therapeutic antibodies," Nature Reviews Immunology, 2010, vol. 10, pp. 345-352.
Ben Nasr, M. et al., "Co-transplantation of autologous MSCs delays islet allograft rejection and generates a local immunoprivileged site," Acta Diabetologica, 2015, vol. 52, pp. 917-927.
Ben Nasr, M. et al., "The rise, fall, and resurgence of immunotherapy in type 1 diabetes," Pharmacological Research, 2015, vol. 98, pp. 31-38.
Binz, H.K. et al., "Designing Repeat Proteins: Well-expressed, Soluble and Stable Proteins from Combinatorial Libraries of Consensus Ankyrin Repeat Proteins," J Mol Biol, 2003, vol. 332, pp. 489-503.
Bluestone, J.A. et al., "Genetics, pathogenesis and clinical interventions in type 1 diabetes," Nature, 2010, vol. 464, pp. 1293-1300.
Boman, B.M. et al., "Human colon cancer stem cells: a new paradigm in gastrointestinal oncology," Journal of Clinical Oncology, 2008, vol. 26, pp. 2828-2838.
Bondy, C.A. et al., "Clinical uses of insulin-like growth factor I," Ann Intern Med, 1994, vol. 120, pp. 593-601.
Bortvedt, S.F. et al., "Insulin-like growth factor 1," *Current Opinion in Gastroenterology*, vol. 28, No. 2, Mar. 1, 2012, pp. 89-98.
Boucher, J. et al., "A kinase-independent role for unoccupied insulin and IGF-1 receptors in control of apoptosis," Sci Signal, 2010, vol. 3, pp. ra87.
Breault, D.T. et al., "Generation of mTert-GFP mice as a model to identify and study tissue progenitor cells," Proc Natl Acad Sci, 2008, vol. 105, pp. 10420-10425.
Brennand, K. et al., "Slow and steady is the key to beta-cell replication," Journal of Cellular and Molecular Medicine, 2009, vol. 13, pp. 472-487.
Brooks, B.D., "The Importance of Epitope Binning in Drug Discovery," Current Drug Discovery Technology, 2014, vol. 11, pp. 109-112.
Burgess, W.H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, Nov. 1990, vol. 111, pp. 2129-2138.
Bytzer, P. et al., "GI symptoms in diabetes mellitus are associated with both poor glycemic control and diabetic complications," Am J Gastroenterol, 2002, vol. 97, pp. 604-611.
Camilleri, M., "Diabetic gastroparesis," N Engl J Med, 2007, vol. 356, pp. 820-829.
Cano, A.E. et al., "Gastrointestinal symptoms in patients with end-stage renal disease undergoing treatment by hemodialysis or peritoneal dialysis," Am J Gastroenterol, 2007, vol. 102, pp. 1990-1997.
Carlone, D.L. et al., "Tales from the crypt: the expanding role of slow cycling intestinal stem cells," Cell Stem Cell, 2012, vol. 10, pp. 2-4.
Carpentino, J.E. et al., "Aldehyde dehydrogenase-expressing colon stem cells contribute to tumorigenesis in the transition from colitis to cancer," Cancer Res, 2009, vol. 69, pp. 8208-8215.
Carrington, E.V. et al., "Traditional measures of normal anal sphincter function using high-resolution anorectal manometry (HRAM) in 115 healthy volunteers," Neurogastroenterology and Motility: The Official Journal of the European Gastrointestinal Motility Society, 2014, vol. 26, pp. 625-635.
Carvello, M. et al., "Inotuzumab ozogamicin murine analog-mediated B-cell depletion reduces anti-islet allo- and autoimmune responses," Diabetes, 2012, vol. 61, pp. 155-165.
Chothia, C. et al., "Structural repertoire of the human VH segments," Journal of Molecular Biology, 1992, vol. 227, No. 3, pp. 799-817.

(56) References Cited

OTHER PUBLICATIONS

Cui, S. et al., "Current understanding concerning intestinal stem cells," World J Gastroenterol, 2016, vol. 22, No. 31, pp. 7099-7110.
D'Addio, F. et al., "Autologous nonmyeloablative hematopoietic stem cell transplantation in new-onset type 1 diabetes: a multicenter analysis," Diabetes, 2014, vol. 63, pp. 3041-3046.
D'Addio, F., et al., "Circulating IGF-I and IGFBP3 levels control human colonic stem cell function and are disrupted in diabetic enteropathy," Cell Stem Cell, Oct. 1, 2015, vol. 17, No. 4, pp. 486-498.
Dall'Acqua, W.F. et al., "Properties of Human IgG1s Engineered for Enhanced Binding to the Neonatal Fc Receptor (FcRn)*," The Journal of Biological Chemistry, 2006, vol. 281, No. 33, pp. 23514-23524.
De Kort, S. et al., "Diabetes mellitus, genetic variants in the insulin-like growth factor pathway and colorectal cancer risk," International Journal of Cancer, 2019, vol. 145, pp. 1774-1781.
De Santi, M. et al., "Use of hormones in doping and cancer risk," Annali di igiene: medicina preventiva e di comunita, 2019, vol. 31, No. 6, pp. 590-594.
Dhingra, A.K. et al., "An update on anti-inflammatory compounds: a review," Anti-Inflammatory & Anti-Allergy Agents in Medicinal Chemistry, 2015, vol. 14, No. 2, pp. 81-97.
Di Cairano, E.S. et al., "The glial glutamate transporter (GLT1) is expressed by pancreatic beta-cells and prevents glutamate-induced beta-cell death," The Journal of Biological Chemistry, 2011, vol. 286, pp. 14007-14018.
D'Mello, S. et al., "Innate Dysfunction Promotes Linear Growth Failure in Pediatric Crohn Disease and Growth Hormone Resistance in Murine Ileitis," Inflammatory Bowel Diseases, 2012, vol. 18, pp. 236-245.
Domenech, A. et al., "Morphofunctional changes underlying intestinal dysmotility in diabetic RIP-I/hIFNbeta transgenic mice," Int J Exp Pathol, 2011, vol. 92, pp. 400-412.
Drogan, D. et al., "Insulin-Like Growth Factor 1 and Insulin-Like Growth Factor-Binding Protein 3 in Relation to the Risk of Type 2 Diabetes Mellitus: Results from the EPIC-Potsdam Study," Am J Epidemiol, 2016, vol. 183, No. 6, pp. 553-560.
Eichele, D.D. et al., "Dextran sodium sulfate colitis murine model: an indispensable tool for advancing our understanding of inflammatory bowel disease pathogenesis," World J Gastroenterol, 2017, vol. 23, No. 33, pp. 6016-6029.
Eisenbarth, G.S., "Type I diabetes mellitus. A chronic autoimmune disease," The New England Journal of Medicine, 1986, vol. 314, pp. 1360-1368.
Faraj, J. et al., "Oesophageal dysmotility, delayed gastric emptying and gastrointestinal symptoms in patients with diabetes mellitus," Diabet Med, 2007, vol. 24, pp. 1235-1239.
Feldman, M. et al., "Disorders of gastrointestinal motility associated with diabetes mellitus," Ann Intern Med, 1983, vol. 98, pp. 378-384.
Filippi, C.M. et al., "Viral trigger for type 1 diabetes: pros and cons," Diabetes, 2008, vol. 57, pp. 2863-2871.
Fiorina, P. et al., "Effects of kidney-pancreas transplantation on atherosclerotic risk factors and endothelial function in patients with uremia and type 1 diabetes," Diabetes, 2001, vol. 50, pp. 496-501.
Fiorina, P. et al., "Long-term beneficial effect of islet transplantation on diabetic macro- /microangiopathy in type 1 diabetic kidney-transplanted patients," Diabetes Care, 2003, vol. 26, pp. 1129-1136.
Fiorina, P. et al., "Natural history of kidney graft survival, hypertrophy, and vascular function in end-stage renal disease type 1 diabetic kidney-transplanted patients: beneficial impact of pancreas and successful islet cotransplantation," Diabetes Care, 2005, vol. 28, pp. 1303-1310.
Fiorina, P. et al., "Normalization of multiple hemostatic abnormalities in uremic type 1 diabetes patients after kidney-pancreas transplantation," Diabetes, 2004, vol. 53, pp. 2291-2300.
Flynn, R.S. et al., "Endogenous IGFBP-3 regulates excess collagen expression in intestinal smooth muscle cells of Crohn's disease strictures," Inflammatory Bowel Diseases, vol. 17, No. 1, Jan. 1, 2011, pp. 193-201.
Folli, F. et al., "Proteomics reveals novel oxidative and glycolytic mechanisms in type 1 diabetic patients' skin which are normalized by kidney-pancreas transplantation," PLoS One, 2010, vol. 5, pp. e9923.
Forbes, K. et al., "Transforming growth factor-β (TGFβ) receptors I/II differentially regulate TGFB1 and IGF-binding protein-3 mitogenic effects in the human placenta," Endocrinology, 2010, vol. 151, pp. 1723-1731.
Ge et al., "Generation of Soluble Leptin Receptor by Ectodomain Shedding of Membrane-spanning Receptors in Vitro and in Vivo," *Journal of Biological Chemistry*, vol. 277, Issue 48, Nov. 29, 2002, pp. 45898-45903.
GenBank: AAH17488.1 "TMEM219 protein, partial [*Homo sapiens*]" NCBI, Jun. 16, 2008, 2 Pages, can be retrieved at <URL:https://www.ncbi.nlm.nih.gov/protein/AAH17488>.
George, M.J. et al., Current Treatment Option for Type 2 Diabetes Mellitus in Youth: Today's Realities and Lessons from the TODAY Study, Curr Diab Rep, 2013, vol. 13, No. 1, pp. 72-80.
Gersemann, M. et al., "From intestinal stem cells to inflammatory bowel diseases," World Journal of Gastroenterology, 2011, vol. 17, pp. 3198-3203.
Giustina, A. et al., "Insulin and GH-IGF-I axis: endocrine pacer or endocrine disruptor?" Acta Diabetol, 2014, vol. 52, pp. 433-443.
Goswami, S. et al., "Developments and Challenges for mAb-Based Therapeutics," Antibodies, 2013, vol. 2, pp. 452-500.
Gracz, A.D. et al., "Brief Report: CD24 and CD44 mark human intestinal epithelial cell populations with characteristics of active and facultative stem cells," Stem Cells, 2013, vol. 31, pp. 2024-2030.
Hinton, P.R et al., "An Engineered Human IgG1 Antibody with Longer Serum Half-Life," The Journal of Immunology, 2006, vol. 176, No. 1, pp. 346-356.
Huch, M. et al., "In vitro expansion of single Lgr5+ liver stem cells induced by Wnt-driven regeneration," Nature, 2013, vol. 494, pp. 247-250.
Hughes, K.R. et al., "Expression profiling of Wnt family of genes in normal and inflammatory bowel disease primary human intestinal myofibroblasts and normal human colonic crypt epithelial cells," Inflamm Bowel Dis, 2011, vol. 17, pp. 213-220.
Ingermann, A.R. et al., "Identification of a Novel Cell Death Receptor Mediating IGFBP-3-induced Anti-tumor Effects in Breast and Prostate Cancer," The Journal of Biological Chemistry, Sep. 24, 2010, vol. 285, No. 39, pp. 30233-30246.
International Preliminary Report on Patentability Chapter II, Patent Cooperation Treaty Application No. PCT/EP2016/062792, May 23, 2017, 10 pages.
International Search Report and Written Opinion, Patent Cooperation Treaty Application No. PCT/EP2016/062790, Sep. 26, 2016, 12 pages.
International Search Report and Written Opinion, Patent Cooperation Treaty Application No. PCT/EP2016/062792, Sep. 30, 2016, 9 pages.
International Search Report and Written Opinion, Patent Cooperation Treaty Application No. PCT/EP2019/076771, Mar. 16, 2020, 27 pages.
International Search Report and Written Opinion, Patent Cooperation Treaty Application No. PCT/EP2020/082292, Mar. 29, 2021, 17 pages.
International Search Report and Written Opinion, Patent Cooperation Treaty Application No. PCT/EP2020/082890, Feb. 22, 2021, 13 pages.
Jain, V., "Management of Type 1 Diabetes in Children and Adolescents," Indian J Pediatr, 2014, vol. 81, No. 2, pp. 170-177.
Jung, P. et al., "Isolation and in vitro expansion of human colonic stem cells," Nat Med, 2011, vol. 17, pp. 1225-1227.
Kam, N.W.S. et al., "Carbon nanotubes as multifunctional biological transporters and near-infrared agents for selective cancer cell destruction," PNAS, 2005, vol. 102, No. 33, p. 11600-11605.
Kaplan, G.G., "The global burden of IBD: from 2015 to 2025," Nat Rev Gastroenterol Hepatol, 2015, vol. 12, No. 12, pp. 720-727.

(56) References Cited

OTHER PUBLICATIONS

Katsanos, K.H. et al., "Reduced serum insulin-like growth factor-1 (IGF-1) and IGF-binding protein-3 levels in adults with inflammatory bowel disease," Growth Hormone & IGF Research, 2001, vol. 11, pp. 364-367.
Keenan, H.A. et al., "Residual insulin production and pancreatic β-cell turnover after 50 years of diabetes: Joslin Medalist Study," Diabetes, 2010, vol. 59, No. 11, pp. 2846-2853.
Kirman, I. et al., "Insulin-like Growth Factor Binding Protein 3 in Inflammatory Bowel Disease," Digestive Diseases and Sciences, Apr. 2005, vol. 50, No. 4, pp. 780-784.
Kohl, A. et al., "Designed to be stable: Crystal structure of a consensus ankyrin repeat protein," PNAS, 2003, vol. 100, No. 4, pp. 1700-1705.
Kosinksi, C. et al., "Gene expression patterns of human colon tops and basal crypts and BMP antagonists as intestinal stem cell niche factors," Proceedings of the National Academy of Sciences of the United States of America, 2007, vol. 104, pp. 15418-15423.
Kuemmerle, J.F. et al., "IGFBP-3 actives TFG-β receptors and directly inhibits growth in human intestinal smooth muscle cells," Am J Physiol Gastrointest Liver Physiol, Jun. 3, 2004, vol. 287, pp. G795-G802.
Kundu, P. et al., "An EphB-Abl signaling pathway is associated with intestinal tumor initiation and growth," Science Translational Medicine, 2015, vol. 7, pp. 281ra44.
Lazar, E. et al., "Transforming Growth Factor alpha: mutation of aspartic acid 47 and leucine 48 results in different biological activities," Molecular and Cellular Biology, Mar. 1988, vol. 8, No. 3, pp. 1247-1252.
Le Roith, D., "Seminars in medicine of the Beth Israel Deaconess Medical Center. Insulin-like growth factors," N Engl J Med, 1997, vol. 336, pp. 633-640.
Lin, M.C. et al. "Structure-function relations in glucagon. Properties of highly purified Des-his1-, monoiodo-, and [Des-Asn28, Thr29](homoserine lactone27)-glucagon," Biochemistry, 1975, vol. 14, No. 8, pp. 1559-1563.
Lui, J.C. et al., "EZH1 and EZH2 promote skeletal growth by repressing inhibitors of chondrocyte proliferation and hypertrophy," *Nature Communications*, 7, Article No. 13685, Nov. 29, 2016, 12 pages.
Ma, X. et al., "A new mutation in BFSP2 (G1091A) causes autosomal dominant congenital lamellar cataracts," Molecular Vision, 2008, vol. 14, pp. 1906-1911.
Mahe, M.M. et al., "Establishment of gastrointestinal epithelial organoids," Curr Protoc Mouse Biol, 2013, vol. 3, pp. 217-240.
Marsha, J.D., "Lipid Management in Patients with Type 2 Diabetes," Am Health Drug Benefits, 2011, vol. 4, No. 5, pp. 312-322.
Mclean, M.H. et al., "Does the microbiota play a role in the pathogenesis of autoimmune diseases?", Gut, 2015, vol. 64, pp. 332-341.
Medema, J.P. et al., "Microenvironmental regulation of stem cells in intestinal homeostasis and cancer," Nature, 2011, vol. 474, pp. 318-326.
Meier, J.J. et al., "Sustained beta cell apoptosis in patients with long-standing type 1 diabetes: indirect evidence for islet regeneration? ", Diabetologia, 2005, vol. 48, No. 11, pp. 2221-2228.
Merlos-Suarez, A. et al., "The intestinal stem cell signature identifies colorectal cancer stem cells and predicts disease relapse," Cell Stem Cell, 2011, vol. 8, pp. 511-524.
Müllberg at al., "The soluble interleukin-6 receptor is generated by shedding," *European Journal of Immunology*, vol. 23, Issue 2, Feb. 1993, pp. 473-480.
Munoz, J. et al., "The lgr5 intestinal stem cell signature: robust expression of proposed quiescent '+4' cell markers," EMBO J, 2012, vol. 31, pp. 3079-3091.
Muzumdar, R., et al., "Central and Opposing Effects of IGF-1 and IGF-Binding Protein-3 on Systemic Insulin Action," Diabetes, Oct. 2006, vol. 55, pp. 2788-2796.
Nano, R. et al., "Islet isolation for alltransplantation: variables associated with successful islet yield and graft function," Diabetologia, 2005, vol. 48, pp. 906-912.
Nathan, D.M., "Diabetes: Advances in Diagnosis and Treatment," Jama, 2015, vol. 314, pp. 1052-1062.
Nguyen, K.H. et al., "Human IGF Binding Protein-3 Overexpression Impairs Glucose Regulation in Mice via an Inhibition of Insulin Secretion," Endocrinology, 2011, vol. 152, No. 6, pp. 2184-2196.
Oh, Y. et al., "Antiproliferative actions of insulin-like growth factor binding protein (IGFBP)-3 in human breast cancer cells," Prog Growth Factor Res, 1995, vol. 6, pp. 503-512.
Oilinki, T. et al., "Prevalence and characteristics of diabetes among Somali children and adolescents living in Helsinki, Finland," Pediatric Diabetes, 2012, vol. 13, pp. 176-180.
Pambianco, G. et al. "The 30-year natural history of type 1 diabetes complications: the Pittsburgh Epidemiology of Diabetes Complications Study experience," Diabetes, 2006, vol. 55, pp. 1463-1469.
Peet, A. et al., "Circulating IGF1 and IGFBP3 in relation to the development of β-cell autoimmunity in young children," Eur J Endocrinol, 2015, vol. 173, No. 2, pp. 129-137.
Petkova, S.B. et al., "Enhanced half-life of genetically engineered human IgG1 antibodies in a humanized FcRn mouse model: potential application in humorally mediated autoimmune disease," International Immunology, 2006, vol. 18, No. 12, pp. 1759-1769.
Petrelli, A. et al., "IL-21 is an antitolerogenic cytokine of the late-phase alloimmune response," Diabetes, 2011, vol. 60, pp. 3223-3234.
Piscaglia, A.C. et al., "Circulating hematopoietic stem cells and putative intestinal stem cells in coeliac disease," Journal of Translational Medicine, 2015, vol. 13, pp. 220.
Pithadia, A.B. et al., "Treatment of inflammatory bowel disease (IBD)" Pharmacological Reports, 2011, vol. 63, pp. 629-642.
Pupim, L.B. et al., "Accelerated lean body mass loss in incident chronic dialysis patients with diabetes mellitus," Kidney Int, 2005, vol. 68, pp. 2368-2374.
Remes-Troche, J.M., et al., "Rectoanal reflexes and sensorimotor response in rectal hyposensitivity," Diseases of the Colon and Rectum, 2010, vol. 53, pp. 1047-1054.
Sato, T. et al., "Growing self-organizing mini-guts from a single intestinal stem cell: mechanism and applications," Science, 2013, vol. 340, pp. 1190-1194.
Schonhoff, S.E. et al., "Minireview: Development and Differentiation of Gut Endocrine Cells," Endocrinology, 2004, vol. 145, pp. 2639-2644.
Schwartz, G.P. et al., "A superactive insulin: [B10 Aspartic acid]insulin(human)," Proc Natl Acad Sci, Sep. 1987, vol. 84, pp. 6408-6411.
Schwarz, P.E. et al., "Nonpharmacological interventions for the prevention of type 2 diabetes mellitus," Nature Reviews Endocrinology, 2012, vol. 8, pp. 363-373.
Secchi, A. et al., "Cardiovascular disease and neoplasms after pancreas transplantation," Lancet, 1998, vol. 352, pp. 65-66.
Senger, S. et al., "Celiac Disease Histopathology Recapitulates Hedgehog Downregulation, Consistent with Wound Healing Processes Activation," PloS One, 2015, vol. 10, pp. e0144634.
Smets, Y.F. et al., "Effect of simultaneous pancreas-kidney transplantation on mortality of patients with type-1 diabetes mellitus and end-stage renal failure," Lancet, 1999, vol. 1915-1919.
Spinelli, A. et al. "Intestinal fibrosis in Crohn's disease: medical treatment or surgery?" Current Drug Targets, 2010, vol. 11, No. 2, pp. 242-248.
Sridhar, S.S. et al., "Insulin-insulin-like growth factor axis and colon cancer," J Clin Oncol, 2009, vol. 27, pp. 165-167.
Stange, D.E. et al., "Concise review: the yin and yang of intestinal (cancer) stem cells and their progenitors," Stem Cells, 2013, vol. 31, pp. 2287-2295.
Svedlund, J. et al., "GSRS—a clinical rating scale for gastrointestinal symptoms in patients with irritable bowel syndrome and peptic ulcer disease," Digestive diseases, 1988, vol. 33, pp. 129-134.
Taghipour, N. et al., "An experimental model of colitis induced by dextran sulfate sodium from acute progresses to chronicity in

(56) References Cited

OTHER PUBLICATIONS

C57BL/6: correlation between conditions of mice and the environment," Gastroenterology and Hepatology from Bed to Bench, 2016, vol. 9, No. 1, pp. 45-52.
Talley, N.J. et al., "Impact of chronic gastrointestinal symptoms in diabetes mellitus on health-related quality of life," Am J Gastroenterol, 2001, vol. 96, pp. 71-76.
The Diabetes Control and Complications Research Group, "The effect of intensive treatment of diabetes on the development and progression of long-term complications in insulin-dependent mellitus," N Engl J Med, Sep. 30, 1993, vol. 329, pp. 977-986.
Tomlinson, I.M. et al., "The repertoire of human germline VH sequences reveals about fifty groups of VH segments with different hypervariable loops," Journal of Molecular Biology, 1992, vol. 227, No. 3, pp. 776-798.
United States Office Action, U.S. Appl. No. 16/855,992, filed Apr. 12, 2021, fourteen pages.
United States Office Action, U.S. Appl. No. 17/174,893, filed Sep. 20, 2023, 14 pages.
Van Der Flier, L.G. et al., "Stem cells, self-renewal, and differentiation in the intestinal epithelium," Annual Review of Physiology, 2009, vol. 71, pp. 241-290.
Venepalli, N.K. et al., "Phase I Study of IGF-Methotrexate Conjugate in the Treatment of Advanced Tumors Expressing IGF-1 R," American Journal of Clinical Oncology, Nov. 2019, vol. 42, No. 11, pp. 862-869.
Vergani, A. et al., "A novel clinically relevant strategy to abrogate autoimmunity and regulate alloimmunity in NOD mice," Diabetes, 2010, vol. 59, pp. 2253-2264.
Vergani, A. et al., "Effect of the purinergic inhibitor oxidized ATP in a model of islet allograft rejection," Diabetes, 2013, vol. 62, pp. 1665-1675.
Wang, S. et al., "Circulating IGF-1 promotes prostate adenocarcinoma via FOXO31/BIM signaling in a double-transgenic mouse model," Oncogene, Jul. 16, 2019, vol. 38, pp. 6338-6353.
Wang, Z. et al., "Integrin targeted drug and gene delivery," Expert Opinion on Drug Delivery, 2010, vol. 7, No. 2, pp. 159-171.
Williams, A.C. et al., "Insulin-like growth factor binding protein 3 (IGFBP-3) potentiates TRAIL-induced apoptosis of human colorectal carcinoma cells through inhibition of NF-kappaB," Cell Death Differ, 2007, vol. 14, pp. 137-145.
Wright, A. et al., "Effect of glycosylation on antibody function: implications for genetic engineering," Trends in Biotechnology, 1997, vol. 15, No. 1, pp. 26-32.
Wu, M.J. et al., "Colonic transit time in long-term dialysis patients," Am J Kidney Dis, 2004, vol. 44, pp. 322-327.
Yakar, S. et al., "Serum complexes of insulin-like growth factor-1 modulate skeletal integrity and carbohydrate metabolism," FASEB J, 2009, vol. 23, No. 3, pp. 709-719.
Yancu, D. et al., "A phenotype of IGFBP-3 knockout mice revealed by dextran sulfate-induced colitis," Journal of gastroenterology and hepatology, 2017, vol. 32, No. 1, pp. 146-153.
Yeung, Y.A. et al., "Engineering Human lgG1 Affinity to Human Neonatal Fc Receptor: Impact of Affinity Improvement on Pharmacokinetics in Primates," The Journal of Immunology, 2009, vol. 182, No. 12, pp. 7663-7671.
Yi, P. et al., "Perspectives on the activities of ANGPTL8/betatrophin," Cell, 2014, vol. 159, pp. 467-468.
Zahnd, C. et al., "A Designed Ankyrin Repeat Protein Evolved to Picomolar Affinity to Her2," J Mol Biol, 2007, vol. 369, pp. 1015-1028.
Zeki, S.S. et al., "Stem cells and their implications for colorectal cancer," Nature Reviews, Gastroenterology & Hepatology, 2011, vol. 8, pp. 90-100.
Zhao, J. et al., "Biomechanical and morphometric intestinal remodelling during experimental diabetes in rats," Diabetologia, 2003, vol. 46, pp. 1688-1697.
Ziegler, A.G. et al., "Seroconversion to multiple islet autoantibodies and risk of progression to diabetes in children," Jama, 2013, vol. 309, pp. 2473-2479.
Ziskin, J.L. et al., "In situ validation of an intestinal stem cell signature in colorectal cancer," Gut, 2013, vol. 62, pp. 1012-1023.
Collard, T.J. et al., "Transcriptional upregulation of the insulin-like growth factor binding protein IGFBP-3 by sodium butyrate increases IGF-independent apoptosis in human colonic adenoma-derived epithelial cells," Carcinogenesis, 2003, vol. 24, pp. 393-401.
Katrucha, A.G. "Obtaining Recombinant Antibodies and Methods for Increasing their Affinity," Advances in Biological Chemistry, vol. 50, 2010, pp. 207.
Koiko, R. et al., "Detection of Antibodies and Determination of their Characteristics," Immunology, 2008, pp. 61-62.

* cited by examiner

SEQUENCE LISTING

```
<160> NUMBER OF SEQ ID NOS: 153

<210> SEQ ID NO 1
<211> LENGTH: 5
<212> TYPE: PRT
<213> ORGANISM: Artificial Sequence
<220> FEATURE:
<223> OTHER INFORMATION: synthetic
```

<400> SEQUENCE: 1

Ser Tyr Gly Ile Ser
1 5

<210> SEQ ID NO 2
<211> LENGTH: 5
<212> TYPE: PRT
<213> ORGANISM: Artificial Sequence
<220> FEATURE:
<223> OTHER INFORMATION: synthetic

<400> SEQUENCE: 2

Ser Tyr Ala Met Ser
1 5

<210> SEQ ID NO 3
<211> LENGTH: 5
<212> TYPE: PRT
<213> ORGANISM: Artificial Sequence
<220> FEATURE:
<223> OTHER INFORMATION: synthetic

<400> SEQUENCE: 3

Ser Tyr Ala Ile Ser
1 5

<210> SEQ ID NO 4
<211> LENGTH: 5
<212> TYPE: PRT
<213> ORGANISM: Artificial Sequence
<220> FEATURE:
<223> OTHER INFORMATION: synthetic

<400> SEQUENCE: 4

Ser Tyr Gly Met His
1 5

<210> SEQ ID NO 5
<211> LENGTH: 5
<212> TYPE: PRT
<213> ORGANISM: Artificial Sequence
<220> FEATURE:
<223> OTHER INFORMATION: synthetic

<400> SEQUENCE: 5

Gly Tyr Gly Met Asn
1 5

<210> SEQ ID NO 6
<211> LENGTH: 17
<212> TYPE: PRT
<213> ORGANISM: Artificial Sequence
<220> FEATURE:
<223> OTHER INFORMATION: synthetic

<400> SEQUENCE: 6

Trp Ile Ser Ala Tyr Asn Gly Asn Thr Asn Tyr Ala Gln Lys Leu Gln
1 5 10 15

Gly

<210> SEQ ID NO 7
<211> LENGTH: 17
<212> TYPE: PRT
<213> ORGANISM: Artificial Sequence
<220> FEATURE:

<223> OTHER INFORMATION: synthetic

<400> SEQUENCE: 7

Ala Ile Ser Gly Ser Gly Gly Ser Thr Tyr Tyr Ala Asp Ser Val Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: synthetic

<400> SEQUENCE: 8

Gly Ile Ile Pro Ile Phe Gly Thr Ala Asn Tyr Ala Gln Lys Phe Gln
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: synthetic

<400> SEQUENCE: 9

Val Ile Ser Tyr Asp Gly Ser Asn Lys Tyr Tyr Ala Asp Ser Val Lys
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: synthetic

<400> SEQUENCE: 10

Gly Ile Thr Pro Ile Phe Gly Thr Ala Asn Tyr Ala Gln Lys Phe Gln
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: synthetic

<400> SEQUENCE: 11

Tyr Val Gly Ser Ser Ser Ser Thr Ile Tyr Tyr Ala Asp Ser Val Lys
1               5                   10                  15

Gly

<210> SEQ ID NO 12
<211> LENGTH: 10
<212> TYPE: PRT
<213> ORGANISM: Artificial Sequence
<220> FEATURE:
<223> OTHER INFORMATION: synthetic

<400> SEQUENCE: 12

Glu Trp Glu Leu Leu Gly Gly Leu Asp Tyr
1 5 10

<210> SEQ ID NO 13
<211> LENGTH: 7
<212> TYPE: PRT
<213> ORGANISM: Artificial Sequence
<220> FEATURE:
<223> OTHER INFORMATION: synthetic

<400> SEQUENCE: 13

Gly Ala Gly Thr Leu Asp Tyr
1 5

<210> SEQ ID NO 14
<211> LENGTH: 7
<212> TYPE: PRT
<213> ORGANISM: Artificial Sequence
<220> FEATURE:
<223> OTHER INFORMATION: synthetic

<400> SEQUENCE: 14

Gly Arg Gly Val Ile Asp Tyr
1 5

<210> SEQ ID NO 15
<211> LENGTH: 9
<212> TYPE: PRT
<213> ORGANISM: Artificial Sequence
<220> FEATURE:
<223> OTHER INFORMATION: synthetic

<400> SEQUENCE: 15

Asp Arg Tyr Leu Gly Trp Phe Asp Pro
1 5

<210> SEQ ID NO 16
<211> LENGTH: 7
<212> TYPE: PRT
<213> ORGANISM: Artificial Sequence
<220> FEATURE:
<223> OTHER INFORMATION: synthetic

<400> SEQUENCE: 16

Gly Arg Gly Ser Phe Asp Pro
1 5

<210> SEQ ID NO 17
<211> LENGTH: 10
<212> TYPE: PRT
<213> ORGANISM: Artificial Sequence
<220> FEATURE:
<223> OTHER INFORMATION: synthetic

<400> SEQUENCE: 17

Asp Leu Ala Val Gly Thr His Gly Asp Tyr
1 5 10

<210> SEQ ID NO 18
<211> LENGTH: 10
<212> TYPE: PRT
<213> ORGANISM: Artificial Sequence
<220> FEATURE:
<223> OTHER INFORMATION: synthetic

<400> SEQUENCE: 18

Asn Val Arg Leu Pro Gly Trp Phe Asp Pro 1 5 10

<210> SEQ ID NO 19
<211> LENGTH: 14
<212> TYPE: PRT
<213> ORGANISM: Artificial Sequence
<220> FEATURE:
<223> OTHER INFORMATION: synthetic

<400> SEQUENCE: 19

Gly Asp Tyr Ser Asp Thr Ser Gly Thr Asp Phe Phe Gln His
1 5 10

<210> SEQ ID NO 20
<211> LENGTH: 9
<212> TYPE: PRT
<213> ORGANISM: Artificial Sequence
<220> FEATURE:
<223> OTHER INFORMATION: synthetic

<400> SEQUENCE: 20

Leu Gly Arg Glu Leu Ser Phe Asp Tyr
1 5

<210> SEQ ID NO 21
<211> LENGTH: 12
<212> TYPE: PRT
<213> ORGANISM: Artificial Sequence
<220> FEATURE:
<223> OTHER INFORMATION: synthetic

<400> SEQUENCE: 21

Phe Gly Arg Pro Gln Leu Gly Tyr Ala Phe Asp Ile
1 5 10

<210> SEQ ID NO 22
<211> LENGTH: 12
<212> TYPE: PRT
<213> ORGANISM: Artificial Sequence
<220> FEATURE:
<223> OTHER INFORMATION: synthetic

<400> SEQUENCE: 22

Met Ser Val Ala Gly Pro Ser Ile Ser Phe Asp Tyr
1 5 10

<210> SEQ ID NO 23
<211> LENGTH: 11
<212> TYPE: PRT
<213> ORGANISM: Artificial Sequence
<220> FEATURE:
<223> OTHER INFORMATION: synthetic

<400> SEQUENCE: 23

Ala Gly Ile Leu Thr Gly Tyr Tyr Phe Asp Tyr
1 5 10

<210> SEQ ID NO 24
<211> LENGTH: 5
<212> TYPE: PRT
<213> ORGANISM: Artificial Sequence
<220> FEATURE:
<223> OTHER INFORMATION: synthetic

<400> SEQUENCE: 24

Gly Leu Gly Gly Asn
1 5

<210> SEQ ID NO 25
<211> LENGTH: 9
<212> TYPE: PRT
<213> ORGANISM: Artificial Sequence
<220> FEATURE:
<223> OTHER INFORMATION: synthetic

<400> SEQUENCE: 25

Leu Ser Gly Pro Asn Gly Val Asp Tyr
1               5

<210> SEQ ID NO 26
<211> LENGTH: 8
<212> TYPE: PRT
<213> ORGANISM: Artificial Sequence
<220> FEATURE:
<223> OTHER INFORMATION: synthetic

<400> SEQUENCE: 26

Ile Thr Glu Gly Ala Phe Asp Tyr
1               5

<210> SEQ ID NO 27
<211> LENGTH: 14
<212> TYPE: PRT
<213> ORGANISM: Artificial Sequence
<220> FEATURE:
<223> OTHER INFORMATION: synthetic

<400> SEQUENCE: 27

Thr Gly Thr Ser Ser Asp Val Gly Gly Tyr Asn Tyr Val Ser
1               5                   10

<210> SEQ ID NO 28
<211> LENGTH: 17
<212> TYPE: PRT
<213> ORGANISM: Artificial Sequence
<220> FEATURE:
<223> OTHER INFORMATION: synthetic

<400> SEQUENCE: 28

Lys Ser Ser Gln Ser Val Leu Tyr Ser Ser Asn Asn Lys Asn Tyr Leu
1               5                   10                  15

Ser

<210> SEQ ID NO 29
<211> LENGTH: 17
<212> TYPE: PRT
<213> ORGANISM: Artificial Sequence
<220> FEATURE:
<223> OTHER INFORMATION: synthetic

<400> SEQUENCE: 29

Lys Ser Ser Gln Ser Val Leu Tyr Ser Ser Asn Asn Lys Asn Tyr Leu
1               5                   10                  15

Ala

<210> SEQ ID NO 30
<211> LENGTH: 11
<212> TYPE: PRT
<213> ORGANISM: Artificial Sequence
<220> FEATURE:
<223> OTHER INFORMATION: synthetic

<400> SEQUENCE: 30

```
Arg Ala Ser Gln Ser Ile Ser Ser Trp Leu Ala
1               5                   10


<210> SEQ ID NO 31
<211> LENGTH: 11
<212> TYPE: PRT
<213> ORGANISM: Artificial Sequence
<220> FEATURE:
<223> OTHER INFORMATION: synthetic

<400> SEQUENCE: 31

Arg Ala Ser Gln Ser Ile Ser Ser Tyr Leu Asn
1               5                   10


<210> SEQ ID NO 32
<211> LENGTH: 12
<212> TYPE: PRT
<213> ORGANISM: Artificial Sequence
<220> FEATURE:
<223> OTHER INFORMATION: synthetic

<400> SEQUENCE: 32

Arg Ala Ser Gln Ser Leu Ser Ala Asp Tyr Leu Ala
1               5                   10


<210> SEQ ID NO 33
<211> LENGTH: 13
<212> TYPE: PRT
<213> ORGANISM: Artificial Sequence
<220> FEATURE:
<223> OTHER INFORMATION: synthetic

<400> SEQUENCE: 33

Thr Arg Ser Ser Gly Ser Ile Ala Ser Asn Tyr Val Gln
1               5                   10


<210> SEQ ID NO 34
<211> LENGTH: 13
<212> TYPE: PRT
<213> ORGANISM: Artificial Sequence
<220> FEATURE:
<223> OTHER INFORMATION: synthetic

<400> SEQUENCE: 34

Ser Gly Ser Arg Ser Asn Ile Gly Ser Asn Tyr Val His
1               5                   10


<210> SEQ ID NO 35
<211> LENGTH: 11
<212> TYPE: PRT
<213> ORGANISM: Artificial Sequence
<220> FEATURE:
<223> OTHER INFORMATION: synthetic

<400> SEQUENCE: 35

Gln Gly Asp Ser Val Arg Lys Tyr Tyr Thr Asn
1               5                   10


<210> SEQ ID NO 36
<211> LENGTH: 11
<212> TYPE: PRT
<213> ORGANISM: Artificial Sequence
<220> FEATURE:
<223> OTHER INFORMATION: synthetic

<400> SEQUENCE: 36
```

```
Arg Ala Ser Arg Thr Val Gly Ser Trp Leu Ala
1               5                   10


<210> SEQ ID NO 37
<211> LENGTH: 7
<212> TYPE: PRT
<213> ORGANISM: Artificial Sequence
<220> FEATURE:
<223> OTHER INFORMATION: synthetic

<400> SEQUENCE: 37

Glu Val Ser Asn Arg Pro Ser
1               5


<210> SEQ ID NO 38
<211> LENGTH: 7
<212> TYPE: PRT
<213> ORGANISM: Artificial Sequence
<220> FEATURE:
<223> OTHER INFORMATION: synthetic

<400> SEQUENCE: 38

Trp Ala Ser Thr Arg Glu Ser
1               5


<210> SEQ ID NO 39
<211> LENGTH: 7
<212> TYPE: PRT
<213> ORGANISM: Artificial Sequence
<220> FEATURE:
<223> OTHER INFORMATION: synthetic

<400> SEQUENCE: 39

Glu Val Ser Asn Arg Pro Ser
1               5


<210> SEQ ID NO 40
<211> LENGTH: 7
<212> TYPE: PRT
<213> ORGANISM: Artificial Sequence
<220> FEATURE:
<223> OTHER INFORMATION: synthetic

<400> SEQUENCE: 40

Lys Ala Ser Ser Leu Glu Ser
1               5


<210> SEQ ID NO 41
<211> LENGTH: 7
<212> TYPE: PRT
<213> ORGANISM: Artificial Sequence
<220> FEATURE:
<223> OTHER INFORMATION: synthetic

<400> SEQUENCE: 41

Ala Ala Ser Ser Leu Gln Ser
1               5


<210> SEQ ID NO 42
<211> LENGTH: 7
<212> TYPE: PRT
<213> ORGANISM: Artificial Sequence
<220> FEATURE:
<223> OTHER INFORMATION: synthetic

<400> SEQUENCE: 42

Gly Ala Ser Thr Arg Ala Thr
```

1 5

<210> SEQ ID NO 43
<211> LENGTH: 7
<212> TYPE: PRT
<213> ORGANISM: Artificial Sequence
<220> FEATURE:
<223> OTHER INFORMATION: synthetic

<400> SEQUENCE: 43

Ala Ala Ser Ser Leu Gln Arg
1 5

<210> SEQ ID NO 44
<211> LENGTH: 7
<212> TYPE: PRT
<213> ORGANISM: Artificial Sequence
<220> FEATURE:
<223> OTHER INFORMATION: synthetic

<400> SEQUENCE: 44

Glu Asp Asn Gln Arg Pro Ser
1 5

<210> SEQ ID NO 45
<211> LENGTH: 7
<212> TYPE: PRT
<213> ORGANISM: Artificial Sequence
<220> FEATURE:
<223> OTHER INFORMATION: synthetic

<400> SEQUENCE: 45

Arg Asn Asp Gln Arg Pro Ser
1 5

<210> SEQ ID NO 46
<211> LENGTH: 7
<212> TYPE: PRT
<213> ORGANISM: Artificial Sequence
<220> FEATURE:
<223> OTHER INFORMATION: synthetic

<400> SEQUENCE: 46

Gly Lys Asn Tyr Arg Pro Ser
1 5

<210> SEQ ID NO 47
<211> LENGTH: 7
<212> TYPE: PRT
<213> ORGANISM: Artificial Sequence
<220> FEATURE:
<223> OTHER INFORMATION: synthetic

<400> SEQUENCE: 47

Asp Ala Ser Asn Leu Gln Ser
1 5

<210> SEQ ID NO 48
<211> LENGTH: 10
<212> TYPE: PRT
<213> ORGANISM: Artificial Sequence
<220> FEATURE:
<223> OTHER INFORMATION: synthetic

<400> SEQUENCE: 48

Ser Ser Tyr Thr Ser Ser Ser Thr Val Val
1 5 10

<210> SEQ ID NO 49
<211> LENGTH: 9
<212> TYPE: PRT
<213> ORGANISM: Artificial Sequence
<220> FEATURE:
<223> OTHER INFORMATION: synthetic

<400> SEQUENCE: 49

Gln Gln Tyr Tyr Ser Thr Pro Leu Thr
1 5

<210> SEQ ID NO 50
<211> LENGTH: 11
<212> TYPE: PRT
<213> ORGANISM: Artificial Sequence
<220> FEATURE:
<223> OTHER INFORMATION: synthetic

<400> SEQUENCE: 50

Ser Ser Tyr Thr Ser Ser Ser Thr Pro Tyr Val
1 5 10

<210> SEQ ID NO 51
<211> LENGTH: 12
<212> TYPE: PRT
<213> ORGANISM: Artificial Sequence
<220> FEATURE:
<223> OTHER INFORMATION: synthetic

<400> SEQUENCE: 51

Ser Ser Tyr Thr Ser Ser Ser Thr Leu Glu Val Val
1 5 10

<210> SEQ ID NO 52
<211> LENGTH: 9
<212> TYPE: PRT
<213> ORGANISM: Artificial Sequence
<220> FEATURE:
<223> OTHER INFORMATION: synthetic

<400> SEQUENCE: 52

Gln Gln Tyr Asn Ser Tyr Pro Leu Thr
1 5

<210> SEQ ID NO 53
<211> LENGTH: 8
<212> TYPE: PRT
<213> ORGANISM: Artificial Sequence
<220> FEATURE:
<223> OTHER INFORMATION: synthetic

<400> SEQUENCE: 53

Gln Gln Ser Tyr Ser Thr Pro Gly
1 5

<210> SEQ ID NO 54
<211> LENGTH: 9
<212> TYPE: PRT
<213> ORGANISM: Artificial Sequence
<220> FEATURE:
<223> OTHER INFORMATION: synthetic

<400> SEQUENCE: 54

Gln Gln Ser Tyr Ser Glu Ser Trp Thr
1 5

<210> SEQ ID NO 55
<211> LENGTH: 9
<212> TYPE: PRT
<213> ORGANISM: Artificial Sequence
<220> FEATURE:
<223> OTHER INFORMATION: synthetic

<400> SEQUENCE: 55

Gln Gln Asn Asp Asn Trp Pro Tyr Thr
1               5

<210> SEQ ID NO 56
<211> LENGTH: 9
<212> TYPE: PRT
<213> ORGANISM: Artificial Sequence
<220> FEATURE:
<223> OTHER INFORMATION: synthetic

<400> SEQUENCE: 56

Gln Glu Thr Tyr Ser Asn Leu Trp Thr
1               5

<210> SEQ ID NO 57
<211> LENGTH: 11
<212> TYPE: PRT
<213> ORGANISM: Artificial Sequence
<220> FEATURE:
<223> OTHER INFORMATION: synthetic

<400> SEQUENCE: 57

Gln Ser Tyr Asp Ser Ser Asn Arg Pro Trp Val
1               5                   10

<210> SEQ ID NO 58
<211> LENGTH: 10
<212> TYPE: PRT
<213> ORGANISM: Artificial Sequence
<220> FEATURE:
<223> OTHER INFORMATION: synthetic

<400> SEQUENCE: 58

Ala Ala Trp Asp Asp Gly Leu Ser Val Leu
1               5                   10

<210> SEQ ID NO 59
<211> LENGTH: 12
<212> TYPE: PRT
<213> ORGANISM: Artificial Sequence
<220> FEATURE:
<223> OTHER INFORMATION: synthetic

<400> SEQUENCE: 59

His Ser Arg Asp Thr Ser Asp Ile His Leu Asn Val
1               5                   10

<210> SEQ ID NO 60
<211> LENGTH: 9
<212> TYPE: PRT
<213> ORGANISM: Artificial Sequence
<220> FEATURE:
<223> OTHER INFORMATION: synthetic

<400> SEQUENCE: 60

Gln Gln Tyr Asn Ser Ser Pro Tyr Thr
1               5

```
<210> SEQ ID NO 61
<211> LENGTH: 119
<212> TYPE: PRT
<213> ORGANISM: Artificial Sequence
<220> FEATURE:
<223> OTHER INFORMATION: synthetic

<400> SEQUENCE: 61

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Trp Glu Leu Leu Gly Gly Leu Asp Tyr Trp Gly Gln Gly
            100                 105                 110

Thr Leu Val Thr Val Ser Ser
        115


<210> SEQ ID NO 62
<211> LENGTH: 116
<212> TYPE: PRT
<213> ORGANISM: Artificial Sequence
<220> FEATURE:
<223> OTHER INFORMATION: synthetic

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Gly Thr Leu Asp Tyr Trp Gly Gln Gly Thr Leu Val
            100                 105                 110

Thr Val Ser Ser
        115


<210> SEQ ID NO 63
<211> LENGTH: 116
<212> TYPE: PRT
<213> ORGANISM: Artificial Sequence
<220> FEATURE:
<223> OTHER INFORMATION: synthetic

<400> SEQUENCE: 63

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Arg Gly Val Ile Asp Tyr Trp Gly Gln Gly Thr Leu Val
            100                 105                 110

Thr Val Ser Ser
        115
```

<210> SEQ ID NO 64
<211> LENGTH: 118
<212> TYPE: PRT
<213> ORGANISM: Artificial Sequence
<220> FEATURE:
<223> OTHER INFORMATION: synthetic

<400> SEQUENCE: 64

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Tyr Leu Gly Trp Phe Asp Pro Trp Gly Gln Gly Thr
            100                 105                 110

Leu Val Thr Val Ser Ser
        115
```

<210> SEQ ID NO 65
<211> LENGTH: 116
<212> TYPE: PRT
<213> ORGANISM: Artificial Sequence
<220> FEATURE:
<223> OTHER INFORMATION: synthetic

<400> SEQUENCE: 65

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
```

```
65                  70                  75                  80

Met Glu Leu Arg Ser Leu Arg Ser Asp Asp Thr Ala Val Tyr Tyr Cys
                85                  90                  95

Ala Arg Gly Arg Gly Ser Phe Asp Pro Trp Gly Gln Gly Thr Leu Val
            100                 105                 110

Thr Val Ser Ser
        115


<210> SEQ ID NO 66
<211> LENGTH: 119
<212> TYPE: PRT
<213> ORGANISM: Artificial Sequence
<220> FEATURE:
<223> OTHER INFORMATION: synthetic

<400> SEQUENCE: 66

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Ala Val Gly Thr His Gly Asp Tyr Trp Gly Gln Gly
            100                 105                 110

Thr Leu Val Thr Val Ser Ser
        115


<210> SEQ ID NO 67
<211> LENGTH: 119
<212> TYPE: PRT
<213> ORGANISM: Artificial Sequence
<220> FEATURE:
<223> OTHER INFORMATION: synthetic

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Arg Leu Pro Gly Trp Phe Asp Pro Trp Gly Gln Gly
            100                 105                 110

Thr Leu Val Thr Val Ser Ser
        115
```

```
<210> SEQ ID NO 68
<211> LENGTH: 123
<212> TYPE: PRT
<213> ORGANISM: Artificial Sequence
<220> FEATURE:
<223> OTHER INFORMATION: synthetic

<400> SEQUENCE: 68

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Ser Asp Thr Ser Gly Thr Asp Phe Phe Gln His
            100                 105                 110

Trp Gly Gln Gly Thr Gln Val Thr Val Ser Ser
        115                 120


<210> SEQ ID NO 69
<211> LENGTH: 118
<212> TYPE: PRT
<213> ORGANISM: Artificial Sequence
<220> FEATURE:
<223> OTHER INFORMATION: synthetic

<400> SEQUENCE: 69

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Gly Arg Glu Leu Ser Phe Asp Tyr Trp Gly Gln Gly Thr
            100                 105                 110

Leu Val Thr Val Ser Ser
        115


<210> SEQ ID NO 70
<211> LENGTH: 121
<212> TYPE: PRT
<213> ORGANISM: Artificial Sequence
<220> FEATURE:
<223> OTHER INFORMATION: synthetic

<400> SEQUENCE: 70

Gln Val Gln Leu Val Gln Ser Gly Ala Glu Val Lys Lys Pro Gly Ser
```

```
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Gly Arg Pro Gln Leu Gly Tyr Ala Phe Asp Ile Trp Gly
            100                 105                 110

Gln Gly Thr Met Val Thr Val Ser Ser
        115                 120


<210> SEQ ID NO 71
<211> LENGTH: 121
<212> TYPE: PRT
<213> ORGANISM: Artificial Sequence
<220> FEATURE:
<223> OTHER INFORMATION: synthetic

<400> SEQUENCE: 71

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Met Ser Val Ala Gly Pro Ser Ile Ser Phe Asp Tyr Trp Gly
            100                 105                 110

Gln Gly Thr Leu Val Thr Val Ser Ser
        115                 120


<210> SEQ ID NO 72
<211> LENGTH: 120
<212> TYPE: PRT
<213> ORGANISM: Artificial Sequence
<220> FEATURE:
<223> OTHER INFORMATION: synthetic

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Thr Pro Ile Phe Gly Thr Ala Asn Tyr Ala Gln Lys Phe
    50                  55                  60
```

```
Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Ile Leu Thr Gly Tyr Tyr Phe Asp Tyr Trp Gly Gln
            100                 105                 110

Gly Thr Leu Val Thr Val Ser Ser
        115                 120


<210> SEQ ID NO 73
<211> LENGTH: 114
<212> TYPE: PRT
<213> ORGANISM: Artificial Sequence
<220> FEATURE:
<223> OTHER INFORMATION: synthetic

<400> SEQUENCE: 73

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Tyr
            20                  25                  30

Gly Met Asn Trp Val Arg Gln Ala Pro Gly Lys Gly Leu Glu Trp Val
        35                  40                  45

Ser Tyr Val Gly Ser Ser Ser Ser Thr Ile Tyr Tyr Ala Asp Ser Val
    50                  55                  60

Lys Gly Arg Phe Thr Ile Ser Arg Asp Asn Ala Asn Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Gly Gly Asn Trp Gly Gln Gly Thr Met Val Thr Val
            100                 105                 110

Ser Ser


<210> SEQ ID NO 74
<211> LENGTH: 118
<212> TYPE: PRT
<213> ORGANISM: Artificial Sequence
<220> FEATURE:
<223> OTHER INFORMATION: synthetic

<400> SEQUENCE: 74

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Pro Asn Gly Val Asp Tyr Trp Gly Gln Gly Thr
            100                 105                 110

Leu Val Thr Val Ser Ser
        115
```

<210> SEQ ID NO 75
<211> LENGTH: 117
<212> TYPE: PRT
<213> ORGANISM: Artificial Sequence
<220> FEATURE:
<223> OTHER INFORMATION: synthetic

<400> SEQUENCE: 75

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ile Thr Glu Gly Ala Phe Asp Tyr Trp Gly Gln Gly Thr Leu
            100                 105                 110

Val Thr Val Ser Ser
        115
```

<210> SEQ ID NO 76
<211> LENGTH: 110
<212> TYPE: PRT
<213> ORGANISM: Artificial Sequence
<220> FEATURE:
<223> OTHER INFORMATION: synthetic

<400> SEQUENCE: 76

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Val Val Phe Gly Gly Gly Thr Lys Leu Thr Val Leu
            100                 105                 110
```

<210> SEQ ID NO 77
<211> LENGTH: 113
<212> TYPE: PRT
<213> ORGANISM: Artificial Sequence
<220> FEATURE:
<223> OTHER INFORMATION: synthetic

<400> SEQUENCE: 77

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
```

```
            20                  25                  30

Ser Asn Asn Lys Asn Tyr Leu Ser Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys


<210> SEQ ID NO 78
<211> LENGTH: 113
<212> TYPE: PRT
<213> ORGANISM: Artificial Sequence
<220> FEATURE:
<223> OTHER INFORMATION: synthetic

<400> SEQUENCE: 78

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Asp Ile
            100                 105                 110

Lys


<210> SEQ ID NO 79
<211> LENGTH: 111
<212> TYPE: PRT
<213> ORGANISM: Artificial Sequence
<220> FEATURE:
<223> OTHER INFORMATION: synthetic

<400> SEQUENCE: 79

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95
```

```
Ser Thr Pro Tyr Val Phe Gly Thr Gly Thr Lys Leu Thr Val Leu
            100                 105                 110


<210> SEQ ID NO 80
<211> LENGTH: 113
<212> TYPE: PRT
<213> ORGANISM: Artificial Sequence
<220> FEATURE:
<223> OTHER INFORMATION: synthetic

<400> SEQUENCE: 80

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys


<210> SEQ ID NO 81
<211> LENGTH: 112
<212> TYPE: PRT
<213> ORGANISM: Artificial Sequence
<220> FEATURE:
<223> OTHER INFORMATION: synthetic

<400> SEQUENCE: 81

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Glu Val Val Phe Gly Gly Gly Thr Lys Leu Thr Val Leu
            100                 105                 110


<210> SEQ ID NO 82
<211> LENGTH: 107
<212> TYPE: PRT
<213> ORGANISM: Artificial Sequence
<220> FEATURE:
<223> OTHER INFORMATION: synthetic

<400> SEQUENCE: 82

Asp Ile Gln Met Thr Gln Ser Pro Ser Thr Leu Ser Ala Ser Val Gly
```

```
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105


<210> SEQ ID NO 83
<211> LENGTH: 106
<212> TYPE: PRT
<213> ORGANISM: Artificial Sequence
<220> FEATURE:
<223> OTHER INFORMATION: synthetic

<400> SEQUENCE: 83

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gly
                85                  90                  95

Phe Gly Gly Gly Thr Lys Val Glu Ile Lys
            100                 105


<210> SEQ ID NO 84
<211> LENGTH: 107
<212> TYPE: PRT
<213> ORGANISM: Artificial Sequence
<220> FEATURE:
<223> OTHER INFORMATION: synthetic

<400> SEQUENCE: 84

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Glu Ser Trp
                85                  90                  95
```

```
Thr Phe Gly Gln Gly Thr Thr Val Asp Ile Lys
            100                 105


<210> SEQ ID NO 85
<211> LENGTH: 108
<212> TYPE: PRT
<213> ORGANISM: Artificial Sequence
<220> FEATURE:
<223> OTHER INFORMATION: synthetic

<400> SEQUENCE: 85

Glu Thr Thr Leu Thr Gln Ser Pro Gly Thr Leu Ser Val Ser Pro Gly
1               5                   10                  15

Asp Arg Ala Thr Leu Ser Cys Arg Ala Ser Gln Ser Leu Ser Ala Asp
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Val Ser Ser Leu Gln
65                  70                  75                  80

Ser Glu Asp Phe Ala Val Tyr Tyr Cys Gln Gln Asn Asp Asn Trp Pro
                85                  90                  95

Tyr Thr Phe Gly Gln Gly Thr Lys Leu Glu Ile Lys
            100                 105


<210> SEQ ID NO 86
<211> LENGTH: 107
<212> TYPE: PRT
<213> ORGANISM: Artificial Sequence
<220> FEATURE:
<223> OTHER INFORMATION: synthetic

<400> SEQUENCE: 86

Asp Ile Gln Met Thr Gln Ser Pro Ser Ser Leu Ser Ala Ser Val Gly
1               5                   10                  15

Asp Arg Val Ala Ile Pro Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Glu Thr Tyr Ser Asn Leu Trp
                85                  90                  95

Thr Phe Gly Gln Gly Thr Lys Val Glu Ile Lys
            100                 105


<210> SEQ ID NO 87
<211> LENGTH: 112
<212> TYPE: PRT
<213> ORGANISM: Artificial Sequence
<220> FEATURE:
<223> OTHER INFORMATION: synthetic

<400> SEQUENCE: 87

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
```

```
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Arg Pro Trp Val Phe Gly Gly Gly Thr Lys Leu Thr Val Leu
            100                 105                 110


<210> SEQ ID NO 88
<211> LENGTH: 109
<212> TYPE: PRT
<213> ORGANISM: Artificial Sequence
<220> FEATURE:
<223> OTHER INFORMATION: synthetic

<400> SEQUENCE: 88

Gln Pro Gly Leu Thr Gln Pro Pro Ser Ala Ser Gly Ala Pro Gly Gln
1               5                   10                  15

Arg Val Thr Ile Ser Cys Ser Gly Ser Arg Ser Asn Ile Gly Ser Asn
            20                  25                  30

Tyr Val His Trp Tyr Gln Gln Leu Pro Gly Thr Ala Pro Lys Leu Ile
        35                  40                  45

Ile Tyr Arg Asn Asp Gln Arg Pro Ser Gly Val Pro Ala Arg Phe Ser
    50                  55                  60

Ala Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Gly Leu
                85                  90                  95

Ser Val Leu Phe Gly Gly Gly Thr Lys Leu Thr Val Leu
            100                 105


<210> SEQ ID NO 89
<211> LENGTH: 109
<212> TYPE: PRT
<213> ORGANISM: Artificial Sequence
<220> FEATURE:
<223> OTHER INFORMATION: synthetic

<400> SEQUENCE: 89

Ser Ser Glu Leu Thr Gln Asp Pro Ser Val Ser Val Ala Leu Gly Gln
1               5                   10                  15

Thr Val Thr Ile Thr Cys Gln Gly Asp Ser Val Arg Lys Tyr Tyr Thr
            20                  25                  30

Asn Trp Tyr Gln Gln Lys Pro Gly Gln Ala Pro Ile Leu Val Leu Tyr
        35                  40                  45

Gly Lys Asn Tyr Arg Pro Ser Gly Ile Pro Asp Arg Phe Ser Gly Ser
    50                  55                  60

Thr Ser Gly Asp Thr Ala Tyr Leu Thr Ile Thr Gly Ala Gln Ala Glu
65                  70                  75                  80

Asp Ala Ala Asp Tyr Tyr Cys His Ser Arg Asp Thr Ser Asp Ile His
                85                  90                  95

Leu Asn Val Phe Gly Thr Gly Thr Lys Val Thr Val Leu
            100                 105
```

```
<210> SEQ ID NO 90
<211> LENGTH: 107
<212> TYPE: PRT
<213> ORGANISM: Artificial Sequence
<220> FEATURE:
<223> OTHER INFORMATION: synthetic

<400> SEQUENCE: 90

Ala Ile Gln Leu Thr Gln Ser Pro Ser Thr Leu Ser Ala Ser Val Gly
1               5                   10                  15

Asp Arg Val Thr Ile Thr Cys Arg Ala Ser Arg Thr Val Gly Ser Trp
            20                  25                  30

Leu Ala Trp Tyr Gln Gln Lys Pro Gly Lys Ala Pro Lys Leu Leu Ile
        35                  40                  45

Tyr Asp Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Leu Ser Thr Tyr Tyr Cys Gln Gln Tyr Asn Ser Ser Pro Tyr
                85                  90                  95

Thr Phe Gly Gln Gly Thr Lys Val Glu Ile Lys
            100                 105


<210> SEQ ID NO 91
<211> LENGTH: 357
<212> TYPE: DNA
<213> ORGANISM: Artificial Sequence
<220> FEATURE:
<223> OTHER INFORMATION: synthetic

<400> SEQUENCE: 91

caggtgcagc tggtggagtc tggagctgag gtgaagaagc ctggggcctc agtgaaggtc      60

tcctgcaagg cttctggtta cacctttacc agctatggta tcagctgggt gcgacaggcc     120

cctggacaag ggcttgagtg gatgggatgg atcagcgctt acaatggtaa cacaaactat     180

gcacagaagc tccagggcag agtcaccatg accacagaca catccacgag cacagcctac     240

atggagctga gaagcctgag atctgacgac acggccgtgt attactgtgc gagagagtgg     300

gagctacttg gggggcttga ctactggggc cagggaaccc tggtcaccgt gtcctca        357


<210> SEQ ID NO 92
<211> LENGTH: 348
<212> TYPE: DNA
<213> ORGANISM: Artificial Sequence
<220> FEATURE:
<223> OTHER INFORMATION: synthetic

<400> SEQUENCE: 92

gaggtgcagc tgttggagtc tgggggaggc ttggtacagc ctggggggtc cctgagactc      60

tcctgtgcag cctctggatt cacctttagc agctatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcaaatga acagcctgag agccgaggac acggccgtat attactgtgc gagggggct      300

ggtacgcttg actactgggg ccagggaacc ctggtcaccg tgtcctca                  348


<210> SEQ ID NO 93
<211> LENGTH: 348
<212> TYPE: DNA
```

```
<213> ORGANISM: Artificial Sequence
<220> FEATURE:
<223> OTHER INFORMATION: synthetic

<400> SEQUENCE: 93

caggttcagc tggtgcagtc tggggctgag gtgaagaagc ctggggcctc agtgaaggtc     60

tcctgcaagg cttctggtta cacctttacc agctatggta tcagctgggt gcgacaggcc    120

cctggacaag ggcttgagtg gatgggatgg atcagcgctt acaatggtaa cacaaactat    180

gcacagaagc tccagggcag agtcaccatg accacagaca catccacgag cacagcctac    240

atggagctga ggagcctgag atctgacgac acggccgtgt attactgtgc gagaggtcgg    300

ggagttatag actactgggg ccagggaacc ctggtcaccg tgtcctca                 348


<210> SEQ ID NO 94
<211> LENGTH: 354
<212> TYPE: DNA
<213> ORGANISM: Artificial Sequence
<220> FEATURE:
<223> OTHER INFORMATION: synthetic

<400> SEQUENCE: 94

caggtgcagc tggtgcagtc tggggctgag gtgaagaagc ctggggcctc agtgaaggtc     60

tcctgcaagg cttctggtta cacctttacc agctatggta tcagctgggt gcgacaggcc    120

cctggacaag ggcttgagtg gatgggatgg atcagcgctt acaatggtaa cacaaactat    180

gcacagaagc tccagggcag agtcaccatg accacagaca catccacgag cacagcctac    240

atggagctga ggagcctgag atctgacgac acggccgtgt attactgtgc gagagatcga    300

tatttggggt ggttcgaccc ctggggccag ggaaccctgg tcaccgtgtc ctca          354


<210> SEQ ID NO 95
<211> LENGTH: 348
<212> TYPE: DNA
<213> ORGANISM: Artificial Sequence
<220> FEATURE:
<223> OTHER INFORMATION: synthetic

<400> SEQUENCE: 95

caggttcagc tggtgcagtc tggagctgag gtgaagaagc ctggggcctc agtgaaggtc     60

tcctgcaagg cttctggtta cacctttacc agctacggta tcagctgggt gcgacaggcc    120

cctggacaag ggcttgagtg gatgggatgg atcagcgctt acaatggtaa cacaaactat    180

gcacagaagc tccagggcag agtcaccatg accacagaca catccacgag cacagcctac    240

atggagctga ggagcctgag atctgacgac acggccgtgt attactgtgc gagaggtaga    300

ggtagtttcg acccctgggg ccagggaacc ctggtcaccg tgtcctca                 348


<210> SEQ ID NO 96
<211> LENGTH: 357
<212> TYPE: DNA
<213> ORGANISM: Artificial Sequence
<220> FEATURE:
<223> OTHER INFORMATION: synthetic

<400> SEQUENCE: 96

caggtgtagc tggtgcaatc tggagctgag gtgaagaagc ctggggcctc agtgaaggtc     60

tcctgcaagg cttctggtta cacctttacc agctatggta tcagctgggt gcgacaggcc    120

cctggacaag ggcttgagtg gatgggatgg atcagcgctt acaatggtaa cacaaactat    180

gcacagaagc tccagggcag agttaccatg accacagaca catccacgag cacagcctac    240
```

atggagctga ggagcctgag atctgacgac acggccgtgt attactgtgc gagagatctg 300
gcagttggga cccacggtga ctactggggc cagggaaccc tggtcaccgt gtcctca 357

<210> SEQ ID NO 97
<211> LENGTH: 357
<212> TYPE: DNA
<213> ORGANISM: Artificial Sequence
<220> FEATURE:
<223> OTHER INFORMATION: synthetic

<400> SEQUENCE: 97
caggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggaca aatccacgag cacagcctac 240
atggagctga gcagcctgag atctgaggac acggccgtgt attactgtgc gagaaacgtc 300
cgtctcccag gctggttcga cccctggggc cagggaaccc tggtcaccgt gtcctca 357

<210> SEQ ID NO 98
<211> LENGTH: 369
<212> TYPE: DNA
<213> ORGANISM: Artificial Sequence
<220> FEATURE:
<223> OTHER INFORMATION: synthetic

<400> SEQUENCE: 98
gaggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agctgaggac acagctgtat actactgtgc gagaggggac 300
tattctgata ccagtggtac cgatttcttc cagcactggg gccagggcac ccaggtcacc 360
gtgtcctca 369

<210> SEQ ID NO 99
<211> LENGTH: 354
<212> TYPE: DNA
<213> ORGANISM: Artificial Sequence
<220> FEATURE:
<223> OTHER INFORMATION: synthetic

<400> SEQUENCE: 99
caggtgcagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt attactgtgc gaccctcggg 300
agggagctca gctttgacta ctggggccag ggaaccctgg tcaccgtgtc ctca 354

<210> SEQ ID NO 100
<211> LENGTH: 363
<212> TYPE: DNA
<213> ORGANISM: Artificial Sequence
<220> FEATURE:

<223> OTHER INFORMATION: synthetic

<400> SEQUENCE: 100

```
caggtccagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagattcgga    300
aggccgcagc tgggctatgc ttttgatatc tggggccaag ggacaatggt caccgtgtct    360
tca                                                                  363
```

<210> SEQ ID NO 101
<211> LENGTH: 363
<212> TYPE: DNA
<213> ORGANISM: Artificial Sequence
<220> FEATURE:
<223> OTHER INFORMATION: synthetic

<400> SEQUENCE: 101

```
caaatgcagc tggtgcaatc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc aacaatgtca    300
gtggctggtc cttcaatatc ttttgactac tggggccagg gaaccctggt caccgtgtcc    360
tca                                                                  363
```

<210> SEQ ID NO 102
<211> LENGTH: 360
<212> TYPE: DNA
<213> ORGANISM: Artificial Sequence
<220> FEATURE:
<223> OTHER INFORMATION: synthetic

<400> SEQUENCE: 102

```
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcaccccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagcggga    300
attttgactg gttattactt tgactactgg ggccagggaa ccctggtcac cgtgtcctca    360
```

<210> SEQ ID NO 103
<211> LENGTH: 342
<212> TYPE: DNA
<213> ORGANISM: Artificial Sequence
<220> FEATURE:
<223> OTHER INFORMATION: synthetic

<400> SEQUENCE: 103

```
gaggtgcagc tggtggagtc tgggggaggc ttggtacagc ctgggggtc cctgaaactc     60
tcctgtgcag cctctggatt caccttcagt ggctatggca tgaactgggt ccgccaggct    120
ccagggaagg ggctggagtg ggtttcatac gttggtagta gtagtagtac catatactac    180
```

```
gcagattctg tgaagggccg attcaccatc tccagagaca atgccaacaa ctcactgtat    240

ctgcaaatga acagcctgag agccgaggac acggctgtgt attactgtgc gagaggcctc    300

ggtggtaatt ggggccaagg gacaatggtc accgtgtctt ca                       342
```

<210> SEQ ID NO 104
<211> LENGTH: 354
<212> TYPE: DNA
<213> ORGANISM: Artificial Sequence
<220> FEATURE:
<223> OTHER INFORMATION: synthetic

<400> SEQUENCE: 104

```
gaggtgcagc tggtggagtc tgggggaggc gtggtccagc ctgggaggtc cctgagactc     60

tcctgtgcag cctctggatt caccttcagt agctatggca tgcactgggt ccgccaggct    120

ccaggcaagg ggctggagtg ggtggcagtt atatcatatg atggaagtaa taaatactat    180

gcagactccg tgaagggccg attcaccatc tccagagaca attccaagaa cacgctgtat    240

ctgcaaatga acagcctgag agctgaggac acggctgtgt attactgtgc gaaactttcc    300

gggcccaacg gtgtggacta ctggggccag ggaaccctgg tcaccgtgtc ctca          354
```

<210> SEQ ID NO 105
<211> LENGTH: 351
<212> TYPE: DNA
<213> ORGANISM: Artificial Sequence
<220> FEATURE:
<223> OTHER INFORMATION: synthetic

<400> SEQUENCE: 105

```
caggttcagc tggtgcagtc tggggctgag gtgaagaagc ctgggtcctc ggtgaaggtc     60

tcctgcaagg cttctggagg caccttcagc agctatgcta tcagctgggt gcgacaggcc    120

cctggacaag ggcttgagtg gatgggaggg atcatcccta tctttggtac agcaaactac    180

gcacagaagt tccagggcag agtcacgatt accgcggacg aatccacgag cacagcctac    240

atggagctga gcagcctgag atctgaggac acggccgtgt attactgtgc gagcattacg    300

gagggggcct ttgactactg gggccaggga accctggtca ccgtgtcctc a             351
```

<210> SEQ ID NO 106
<211> LENGTH: 330
<212> TYPE: DNA
<213> ORGANISM: Artificial Sequence
<220> FEATURE:
<223> OTHER INFORMATION: synthetic

<400> SEQUENCE: 106

```
cagtctgccc tgactcagcc tgcctccgtg tctgggtctc ctggacagtc gatcaccatc     60

tcctgcactg gaaccagcag tgacgttggt ggttataact atgtctcctg gtaccaacag    120

cacccaggca aagcccccaa actcatgatt tatgaggtca gtaatcggcc ctcaggggtt    180

tctaatcgct tctctggctc caagtctggc aacacggcct ccctgaccat ctctgggctc    240

caggctgagg acgaggctga ttattactgc agctcatata caagcagcag cactgtggta    300

ttcggcggag ggaccaagct gaccgtccta                                     330
```

<210> SEQ ID NO 107
<211> LENGTH: 339
<212> TYPE: DNA
<213> ORGANISM: Artificial Sequence
<220> FEATURE:

<223> OTHER INFORMATION: synthetic

<400> SEQUENCE: 107

```
gacatcgtga tgacccagtc tccagactcc ctggctgtgt ctctgggcga gagggccacc     60
atcaactgca agtccagcca gagtgtttta tacagctcca acaataagaa ctacttatct    120
tggtaccagc agaaaccagg tcagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
ccgctcactt tcggcggagg gaccaaggtg gaaatcaaa                           339
```

<210> SEQ ID NO 108
<211> LENGTH: 339
<212> TYPE: DNA
<213> ORGANISM: Artificial Sequence
<220> FEATURE:
<223> OTHER INFORMATION: synthetic

<400> SEQUENCE: 108

```
gaaatagtga tgacgcagtc tccagactcc ctggctgtgt ctctgggcga gagggccacc     60
atcaactgca agtccagcca gagtgtttta tacagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
ccgctcactt tcggcggagg gaccaaagtg gatatcaaa                           339
```

<210> SEQ ID NO 109
<211> LENGTH: 333
<212> TYPE: DNA
<213> ORGANISM: Artificial Sequence
<220> FEATURE:
<223> OTHER INFORMATION: synthetic

<400> SEQUENCE: 109

```
cagtctgccc tgactcagcc tgcctccgtg tctgggtctc ctggacagtc gatcaccatc     60
tcctgcactg gaaccagcag tgacgttggt ggttataact atgtctcctg gtaccaacag    120
cacccaggca aagcccccaa actcatgatt tatgaggtca gtaatcggcc ctcaggggtt    180
tctaatcgct tctctggctc caagtctggc aacacggcct ccctgaccat ctctgggctc    240
caggctgagg atgaggctga ttattactgc agctcatata caagcagcag cacccccttat   300
gtcttcggaa ctgggaccaa gctgaccgtc cta                                 333
```

<210> SEQ ID NO 110
<211> LENGTH: 339
<212> TYPE: DNA
<213> ORGANISM: Artificial Sequence
<220> FEATURE:
<223> OTHER INFORMATION: synthetic

<400> SEQUENCE: 110

```
gacatccagt tgacccagtc tccagactcc ctggctgtgt ctctgggcga gagggccacc     60
atcaactgca agtccagcca gagtgtttta tacagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcagcc tgcaggccga agatgtggca gtttattact gtcagcaata ttatagtact    300
```

cctctcactt tcggcggagg gaccaaggtg gagatcaaa 339

<210> SEQ ID NO 111
<211> LENGTH: 336
<212> TYPE: DNA
<213> ORGANISM: Artificial Sequence
<220> FEATURE:
<223> OTHER INFORMATION: synthetic

<400> SEQUENCE: 111
cagtctgccc tgactcagcc tgcctccgtg tctgggtctc ctggacagtc gatcaccatc 60
tcctgcactg gaaccagcag tgacgttggt ggttataact atgtctcctg gtaccaacag 120
cacccaggca aagcccccaa actcatgatt tatgaggtca gtaatcggcc ctcaggggtt 180
tctaatcgct tctctggctc caagtctggc aacacggcct ccctgaccat ctctgggctc 240
caggctgagg acgaggctga ttattactgc agctcataca caagcagcag cactctcgag 300
gtggtattcg gcggagggac caagctgacc gtccta 336

<210> SEQ ID NO 112
<211> LENGTH: 321
<212> TYPE: DNA
<213> ORGANISM: Artificial Sequence
<220> FEATURE:
<223> OTHER INFORMATION: synthetic

<400> SEQUENCE: 112
gacatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgccaacag tataatagtt acccgctcac tttcggcgga 300
gggaccaagg tggagatcaa a 321

<210> SEQ ID NO 113
<211> LENGTH: 318
<212> TYPE: DNA
<213> ORGANISM: Artificial Sequence
<220> FEATURE:
<223> OTHER INFORMATION: synthetic

<400> SEQUENCE: 113
gacatcgtga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta ccccagggtt cggcggaggg 300
accaaggtgg agatcaaa 318

<210> SEQ ID NO 114
<211> LENGTH: 321
<212> TYPE: DNA
<213> ORGANISM: Artificial Sequence
<220> FEATURE:
<223> OTHER INFORMATION: synthetic

<400> SEQUENCE: 114

```
gatattgtga tgactcagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcaacag agttacagtg agtcgtggac gttcggccag    300

gggaccacgg tggacatcaa a                                              321


<210> SEQ ID NO 115
<211> LENGTH: 324
<212> TYPE: DNA
<213> ORGANISM: Artificial Sequence
<220> FEATURE:
<223> OTHER INFORMATION: synthetic

<400> SEQUENCE: 115

gaaacgacac tcacgcagtc tccaggcacc ctgtctgtgt ctccagggga tagagccacc     60

ctctcctgca gggccagtca gagtcttagc gccgactact tagcctggta ccagcagaaa    120

cctggccagg ctcccaggct cctcatctat ggtgcatcca caagggccac tggtatccca    180

gccaggttca gtggcagtgg gtctgggaca gagttcactc tcaccgtcag cagcctgcag    240

tctgaagatt ttgcagttta ttactgtcag cagaatgata actggccgta cacttttggc    300

caggggacca agctggagat caaa                                           324


<210> SEQ ID NO 116
<211> LENGTH: 321
<212> TYPE: DNA
<213> ORGANISM: Artificial Sequence
<220> FEATURE:
<223> OTHER INFORMATION: synthetic

<400> SEQUENCE: 116

gacatccaga tgacccagtc tccatcttcc ctgtccgcat ctgtgggaga cagagtcgcc     60

atcccttgcc gggcaagtca gagcattagc agctacttaa attggtatca gcagaaacca    120

gggaaagccc ctaaactgct gatctacgct gcatccagtt tgcaaagagg ggtcccatca    180

aggttcagtg gcagtggatc tgggacagat ttcactctca ccatcagcag tctgcaacct    240

gaagattttg caacttacta ttgtcaagag acttacagta acctgtggac gttcggccaa    300

gggaccaagg tggaaatcaa a                                              321


<210> SEQ ID NO 117
<211> LENGTH: 336
<212> TYPE: DNA
<213> ORGANISM: Artificial Sequence
<220> FEATURE:
<223> OTHER INFORMATION: synthetic

<400> SEQUENCE: 117

aattttatgc tgactcagcc ccactctgtg tcggagtctc cggggaagac ggtaaccatc     60

tcctgcaccc gcagcagtgg cagcattgcc agcaactatg tgcagtggta ccagcagcgc    120

ccgggcagtt cccccaccac tgtgatctat gaggataacc aaagaccctc tggggtccct    180

gatcggttct ctggctccat cgacagctcc tccaactctg cctccctcac catctctgga    240

ctgaagactg aggacgaggc tgactactac tgtcagtctt atgatagcag caatcggcct    300

tgggtgttcg gcggagggac caagctgacc gtccta                              336
```

<210> SEQ ID NO 118
<211> LENGTH: 327
<212> TYPE: DNA
<213> ORGANISM: Artificial Sequence
<220> FEATURE:
<223> OTHER INFORMATION: synthetic

<400> SEQUENCE: 118

```
cagcctgggc tgactcagcc accctcagcg tctggggccc ccgggcagag ggtcaccatc     60

tcttgttctg gaagcaggtc caatatcggt tctaattatg tacactggta ccaacaactc    120

ccaggaacgg cccccaaact catcatttat aggaatgatc agcggccctc aggggtccct    180

gcccgattct ctgcctccaa gtctggcacc tcagcctccc tggccatcag tgggctccgg    240

tccgaggatg aagctgatta ctactgtgca gcgtgggatg acggactgag tgtcctattc    300

ggcggaggga ccaagttgac cgtccta                                        327
```

<210> SEQ ID NO 119
<211> LENGTH: 327
<212> TYPE: DNA
<213> ORGANISM: Artificial Sequence
<220> FEATURE:
<223> OTHER INFORMATION: synthetic

<400> SEQUENCE: 119

```
tcttctgagc tgactcagga ccccctctgtg tctgtggcct tgggacaaac agtcactatc     60

acgtgccaag gagacagtgt cagaaagtat tatacgaact ggtatcaaca gaagccagga    120

caggcccccta tccttgtcct ctatggtaaa aactaccggc cctcagggat cccagaccga    180

ttctctggct ccacgtccgg agacacagcg tacttgacca tcactggggc tcaggcggag    240

gatgcggcag actattattg tcactcccgg gacaccagtg atatccatct aaatgtcttc    300

ggcactggga ccaaggtcac cgtccta                                        327
```

<210> SEQ ID NO 120
<211> LENGTH: 321
<212> TYPE: DNA
<213> ORGANISM: Artificial Sequence
<220> FEATURE:
<223> OTHER INFORMATION: synthetic

<400> SEQUENCE: 120

```
gccatccagt tgacccagtc tccttccacc ctgtctgcat ctgtaggaga cagagtcacc     60

atcacttgcc gggccagtcg gactgttggt agctggttgg cctggtatca gcagaaacca    120

gggaaagccc ctaagctcct gatctatgat gcctccaatt tgcaaagtgg ggtcccatca    180

aggttcagcg gcagtggatc tgggacagaa ttcactctca ccatcagcag cctgcagcct    240

gatgatttgt caacttatta ctgccaacag tataatagtt ccccgtacac ttttggccag    300

gggaccaagg tggagatcaa a                                              321
```

<210> SEQ ID NO 121
<211> LENGTH: 327
<212> TYPE: PRT
<213> ORGANISM: Artificial Sequence
<220> FEATURE:
<223> OTHER INFORMATION: synthetic

<400> SEQUENCE: 121

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
```

```
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 122
<211> LENGTH: 326
<212> TYPE: PRT
<213> ORGANISM: Artificial Sequence
<220> FEATURE:
<223> OTHER INFORMATION: synthetic

<400> SEQUENCE: 122

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 123
<211> LENGTH: 106
<212> TYPE: PRT
<213> ORGANISM: Artificial Sequence
<220> FEATURE:
<223> OTHER INFORMATION: synthetic

<400> SEQUENCE: 123

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
```

```
                85                  90                  95

Glu Lys Thr Val Ala Pro Thr Glu Cys Ser
            100                 105


<210> SEQ ID NO 124
<211> LENGTH: 106
<212> TYPE: PRT
<213> ORGANISM: Artificial Sequence
<220> FEATURE:
<223> OTHER INFORMATION: synthetic

<400> SEQUENCE: 124

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 125
<211> LENGTH: 107
<212> TYPE: PRT
<213> ORGANISM: Artificial Sequence
<220> FEATURE:
<223> OTHER INFORMATION: synthetic

<400> SEQUENCE: 125

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Phe Thr Phe Ser Ser Tyr
```

1 5

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 127

Gly Phe Thr Phe Ser Ser Tyr Ala Met Ser
1 5 10

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

Ser Ser Tyr Ala Met Ser
1 5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Gly Phe Thr Phe Ser Ser Tyr Ala
1 5

<210> SEQ ID NO 130
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Ser Gly Ser Gly Gly Ser
1 5

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Ala Ile Ser Gly Ser Gly Gly Ser Thr Tyr
1 5 10

<210> SEQ ID NO 132
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Trp Val Ser Ala Ile Ser Gly Ser Gly Gly Ser Thr Tyr
1 5 10

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Ile Ser Gly Ser Gly Gly Ser Thr
1 5

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

Ala Arg Gly Ala Gly Thr Leu Asp
1 5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 135

Ala Arg Gly Ala Gly Thr Leu Asp Tyr
1 5

<210> SEQ ID NO 136
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 136

Leu Tyr Ser Ser Asn Asn Lys Asn Tyr Leu Ser Trp Tyr
1 5 10

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

Gln Ser Val Leu Tyr Ser Ser Asn Asn Lys Asn Tyr
1 5 10

<210> SEQ ID NO 138

<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

Leu Leu Ile Tyr Trp Ala Ser Thr Arg Glu
1 5 10

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 139

Gln Gln Tyr Tyr Ser Thr Pro Leu
1 5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

Gly Tyr Thr Phe Thr Ser Tyr
1 5

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Gly Tyr Thr Phe Thr Ser Tyr Gly Ile Ser
1 5 10

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 142

Thr Ser Tyr Gly Ile Ser
1 5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 143

Gly Tyr Thr Phe Thr Ser Tyr Gly
1 5

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 144

Ser Ala Tyr Asn Gly Asn
1 5

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Trp Ile Ser Ala Tyr Asn Gly Asn Thr Asn
1 5 10

<210> SEQ ID NO 146
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Trp Met Gly Trp Ile Ser Ala Tyr Asn Gly Asn Thr Asn
1 5 10

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Ile Ser Ala Tyr Asn Gly Asn Thr
1 5

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Ala Arg Asp Leu Ala Val Gly Thr His Gly Asp
1 5 10

<210> SEQ ID NO 149
<211> LENGTH: 12
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 149

Ala Arg Asp Leu Ala Val Gly Thr His Gly Asp Tyr
1               5                   10


<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Val Gly Gly Tyr Asn Tyr Val Ser Trp Tyr
1               5                   10


<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ser Ser Asp Val Gly Gly Tyr Asn Tyr
1               5


<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Leu Met Ile Tyr Glu Val Ser Asn Arg Pro
1               5                   10


<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Ser Tyr Thr Ser Ser Ser Thr Leu Glu Val
1               5                   10
```

INHIBITORS AND USES THEREOF

CROSS-REFERENCE TO RELATED APPLICATIONS

This application is the National Stage of International Application No. PCT/EP2021/054215, filed Feb. 19, 2021, which claims priority to European Patent Application Serial No. 20158553.6, filed Feb. 20, 2020, the entire contents of each of which is hereby incorporated by reference herein.

SEQUENCE LISTING

The instant application contains a Sequence Listing which has been submitted electronically in ASCII format and is hereby incorporated by reference in its entirety. Said ASCII copy, created on Feb. 24, 2026, is named 45494US_CRF_sequencelisting.txt and is 75,894 bytes in size.

TECHNICAL FIELD

The present invention relates to inhibitors of IGFBP5 and/or of at least one of its receptors, wherein said inhibitor has anti-fibrotic effect, methods for their production, pharmaceutical compositions containing said inhibitors, and uses thereof. In particular, the invention relates to antibodies or antigen binding fragments thereof that bind specifically to human IGFBP5 and/or to at least one of its receptors.

BACKGROUND ART

IGFBP5

The insulin-like growth factor binding proteins constitute a family of six binding proteins which modulate the bioavailability of insulin-like growth factors (IGFs). Among them, Insulin-like growth factor-binding protein 5 (IGFBP5) is the most conserved member of the IGFBP family (Schneider, et al. Journal of Endocrinology 172, 423-440 (2002)); it binds IGFs with high affinity forming a ternary complex with IGF-1 or -2 and the acid labile subunit (ALS) (Baxter et al. Am J Physiol Endocrinol Metab. 278: E967-E976 (2000)).

In addition to its ability to regulate availability of IGFs, IGFBP5 has also been shown to have IGF-independent functions (Schneider, et al. Journal of Endocrinology 172, 423-440 (2002)). Indeed, it is able to promote fibrosis directly by inducing the expression of extracellular matrix (ECM) genes and indirectly by increasing levels of other growth factors with pro-fibrotic activity, such as connective tissue growth factor (CTGF), resulting in further increase of ECM production. Besides regulating ECM and growth factor genes, IGFBP5 also increases the expression of Lysyl oxidase (LOX), an enzyme responsible for cross-linking the matrix, rendering the ECM more resistant to proteolytic degradation. Moreover, IGFBP5 may bind ECM components and protect them from degradation, thus promoting ECM accumulation and fibrosis, and altering tissue structure and function. Further, IGFBP5 promotes its own expression, generating a positive feedback loop (Nguyen et al. Frontiers in Endocrinology. 9:601 (2018)). IGFBP5 as an important mediator in fibrosis that is upstream of known pro-fibrotic factors, as transforming growth factor beta (TGF-β) signaling. All these data strongly suggest that IGFBP5 exerts its pro-fibrotic activity by directly inducing expression of the majority of the ECM and pro-fibrotic genes. Finally, while majority of the drugs are targeting only one single pro-fibrotic factor downstream the cascade, by targeting IGFBP5 we will be able to block the entire pathway with consequent downregulation of several pro-fibrotic factors and ECM genes.

To the best of our knowledge there are no commercially available monoclonal antibodies against IGFBP5 capable of inhibiting IGFBP5 pro-fibrotic activities, and other detrimental effects on target tissues/cells.

IGFBP5 in Idiopathic Pulmonary Fibrosis

Idiopathic Pulmonary fibrosis (IPF) is a nonneoplastic chronic lung syndrome that is characterized by aberrant accumulation of fibroblasts/myofibroblasts and progressive abnormal remodeling of lung parenchyma, with subsequent scarring and disruption of its structure and function. Despite considerable recent progress, current treatment regimens are largely unpromising with a median survival rate of less than three years from the date of diagnosis (Sureshbabu et al. Pulmonary Medicine. 517687 (2011)). A central event in IPF is the abnormal proliferation and migration of fibroblasts into the alveolar space after lung injury. Although under normal circumstances fibroblasts are important for wound healing and connective tissue production, their function in the fibrotic lung is out of control, leading to formation of fibroblastic foci which consist of highly proliferative fibroblasts, certain immune cells, and excessive ECM protein deposition. The consequences of these processes are disproportionate levels of scar tissue, alterations of the alveolar framework, changes in the lung epithelium structure, stiffening of the functional lung tissue, loss of the gas exchange function of the lung, and dramatically decreased oxygen saturation of the blood (Coward, et al. Ther. Adv. Respir. Dis. 4, 367-388 (2010)).

It has been shown that IGFBP5 is increased in the extracellular milieu when primary fibroblasts are cultured from fibrotic lung tissues of patients with IPF, and that IGFBP5 is deposited in ECM produced by these cells.

Moreover, adenoviral mediated expression of IGFBP5, or addition of recombinant IGFBP5, leads to increased ECM production by primary normal adult lung fibroblasts (Pilewski et al. Am J Pathol 166 (2): 399-407 (2005)).

Interestingly, it has been also observed that transgenic mice for murine dermal fibrosis model utilizes overexpression of IGFBP5 to promote a pro-fibrotic environment leading to fibroblast activation, myofibroblast conversion, and increased deposition of ECM (Yasuoka et al., Am. J. of Pathology 169 (5): 1633-42. (2006)). Using this model, it has been shown that IGFBP5 exerts its pro-fibrotic effects in an IGF-independent manner (Yasuoka et al. Plos One 9 (2) 2014).

IGFBP5 in Scleroderma

Systemic sclerosis (SSc) is a rare systemic autoimmune connective tissue disease characterized by vasculopathy, immune dysregulation and progressive fibrosis, affecting primarily the skin, gastrointestinal tract, lungs, heart and kidneys (Henes et all. Haematologica. (2020)). It is associated with high disease related mortality and the main causes of death are related to cardiac, pulmonary and renal involvement. There are still no effective treatments to prevent or halt the progression of fibrosis in SSc and other fibrosing diseases (Tyndall et al. Ann Rheum Dis. 69 (10): 1809-1815 (2010)).

The excessive fibrosis of the skin and internal organs is due to fibroblast proliferation and excessive production of ECM (Henes et all. Haematologica. (2020)). Fibrotic changes lead to destruction of normal histologic structures in the skin and other organs. IGFBP5 appears to be involved in the early stages of fibrosis and it could be an initiating event in ECM production, suggesting its involvement in the development of fibrosis in SSc. In fact, it has been shown that the expression of IGFBP5 at mRNA and protein levels is increased in vitro in primary fibroblasts cultured from disease-affected skin of patients with SSc, compared with the skin from their healthy twins. It has been also demonstrated that IGFBP5 induces collagen and fibronectin (FN1) production from fibroblasts and induces fibroblast/myofibroblast transdifferentiation in vitro and in vivo (Yasuoka et al., American Journal Of Pathologyl69 (5): 1633-42. (2006)). Moreover, in vivo overexpression of IGFBP5, using replication-deficient adenovirus, induced skin fibrosis in mice which included increased thickness of the dermis and increased collagen bundle thickness (Henes et all. Haematologica. (2020)). Increased expression of alpha smooth muscle actin (α-SMA) and vimentin in dermal fibroblasts was also evident with overexpression of IGFBP5.

IGFBP5 is overexpressed in SSc and IPF (Nguyen X-X, Muhammad L, Nietert P J and Feghali-Bostwick C (2018) Front. Endocrinol. 9:601.doi: 10.3389/fendo.2018.00601 suggesting that strategies to inhibit IGFBP5 function might be effective for the amelioration of fibrosis.

Thus, there is the need for potent and specific IGFBP5 inhibitors, in particular neutralizing antibodies.

SUMMARY OF THE INVENTION

In the present invention it was surprisingly found that disruption, neutralization or blockade of the IGFBP5 axis, including IGFBP5 and any of its receptors has a beneficial effect on fibrosis.

Disclosed herein are inhibitors of IGFBP5 and/or of at least one of its receptors, wherein said inhibitors have anti-fibrotic activity.

The anti-fibrotic activity may be measured by any means known in the art, including as described herein. The isolated antibody or antigen binding fragment thereof is considered to have anti-fibrotic effect when fibrosis is inhibited by at least 10% when compared to a control condition without antibody or antigen binding fragment thereof. Preferably the inhibitor is considered to have anti-fibrotic effect when fibrosis is inhibited by at least 15, 20, 25, 30, 35, 40, 50, 60, 70, 80 or 90% when compared to a control condition without antibody or antigen binding fragment thereof.

Preferably the inhibitor of IGFBP5 and/or of at least one of its receptors is for use in the treatment and/or prevention of fibrosis or of a fibrotic condition.

Still preferably said inhibitor is selected from the group consisting of:

a) a polypeptide;
b) a polynucleotide or a polynucleotide coding for said polypeptide;
c) a vector comprising or expressing said polynucleotide;
d) a host cell genetically engineered expressing said polypeptide or said polynucleotide;
e) a small molecule;
f) a peptide, a protein, an antibody, an antisense oligonucleotide, a siRNA, antisense expression vector or recombinant virus.

More preferably said inhibitor is an isolated antibody or antigen binding fragment thereof that binds to human IGFBP5 or to at least one of its receptors, wherein said isolated antibody or antigen binding fragment thereof has anti-fibrotic effect.

Preferably the inhibitor inhibits, reduces, or neutralizes the formation of αSMA induced by a pro-fibrotic mediator and/or that inhibits, reduces, or neutralizes the formation of FN1 induced by a pro-fibrotic mediator.

Preferably the inhibitor is an isolated antibody or antigen binding fragment thereof that binds to human IGFBP5 and has anti-fibrotic activity.

Preferably the isolated antibody or antigen binding fragment thereof comprises:

a. a heavy chain variable domain (VH) comprising:
   i. a CDR1 sequence of the amino acid sequence selected from the group consisting of: SEQ ID NO: 1, 2, 3, 4 and 5;
   ii. a CDR2 sequence of the amino acid sequence selected from the group consisting of: SEQ ID NO: 6, 7, 8, 9, 10 and 11; and
   iii. a CDR3 sequence of the amino acid sequence selected from the group consisting of: SEQ ID NO: 12, 13, 14, 15, 16, 17, 18, 19, 20, 21, 22, 23, 24, 25 and 26; and/or
b. a light chain variable domain (VL) comprising:
   i. a CDR1 sequence of the amino acid sequence selected from the group consisting of: SEQ ID NO:27, 28, 29, 30, 31, 32, 33, 34, 35 and 36;
   ii. a CDR2 sequence of the amino acid sequence selected from the group consisting of: SEQ ID NO:37, 38, 39, 40, 41, 42, 43, 44, 45, 46, 47; and
   iii. a CDR3 sequence of the amino acid sequence selected from the group consisting of: SEQ ID NO: 48, 49, 50, 51, 52, 53, 54, 55, 56, 57, 58, 59, 60.

Still preferably, the isolated antibody or antigen binding fragment thereof comprises:

a. a heavy chain variable domain (VH) comprising:
   i. a CDR1 sequence of the amino acid sequence selected from the group consisting of a sequence as defined using abysis tool analysis (www.abysis.org) preferably as shown in Table 4.1;
   ii. a CDR2 sequence of the amino acid sequence selected from the group consisting of a sequence as defined using abysis tool analysis (www.abysis.org) preferably as shown in Table 4.1; and
   iii. a CDR3 sequence of the amino acid sequence selected from the group consisting of a sequence as defined using abysis tool analysis (www.abysis.org) preferably as shown in Table 4.1; and/or
b. a light chain variable domain (VL) comprising:
   i. a CDR1 sequence of the amino acid sequence selected from the group consisting of a sequence as defined using abysis tool analysis (www.abysis.org) preferably as shown in Table 4.1;
   ii. a CDR2 sequence of the amino acid sequence selected from the group consisting of a sequence as defined using abysis tool analysis (www.abysis.org) preferably as shown in Table 4.1; and
   iii. a CDR3 sequence of the amino acid sequence selected from the group consisting of a sequence as defined using abysis tool analysis (www.abysis.org) preferably as shown in Table 4.1.

Still preferably, the isolated antibody or antigen binding fragment thereof comprises:

a. a heavy chain variable domain (VH) comprising:
   i. a CDR1 sequence of the amino acid sequence selected from the group consisting of a sequence as defined using abysis tool analysis (www.abysis.org) preferably as shown in Table 5.1;
   ii. a CDR2 sequence of the amino acid sequence selected from the group consisting of a sequence as defined using abysis tool analysis (www.abysis.org) preferably as shown in Table 5.1; and iii. a CDR3 sequence of the amino acid sequence selected from the group consisting of a sequence as defined using abysis tool analysis (www.abysis.org) preferably as shown in Table 5.1; and/or b. a light chain variable domain (VL) comprising:

i. a CDR1 sequence of the amino acid sequence selected from the group consisting of a sequence as defined using abysis tool analysis (www.abysis.org) preferably as shown in Table 5.1;

ii. a CDR2 sequence of the amino acid sequence selected from the group consisting of a sequence as defined using abysis tool analysis (www.abysis.org) preferably as shown in Table 5.1; and iii. a CDR3 sequence of the amino acid sequence selected from the group consisting of a sequence as defined using abysis tool analysis (www.abysis.org) preferably as shown in Table 5.1.

Still preferably, the isolated antibody or antigen binding fragment thereof comprises:

a. a heavy chain variable domain sequence of the amino acid sequence selected from the group consisting of: SEQ ID NO:61, 62, 63, 64, 65, 66, 67, 68, 69, 70, 71, 72, 73, 74 and 75 or b. a light chain variable domain sequence of the amino acid sequence selected from the group consisting of: SEQ ID NO: 76, 77, 78, 79, 80, 81, 82, 83, 84, 85, 86, 87, 88, 89, and 90 or c. the heavy chain variable domain of (a) and the light chain variable domain of (b).

Still preferably, the isolated antibody or antigen binding fragment thereof is selected from the group consisting of: A09, B06, C02, D10, F05, B09, B11, C11, C12, D12, E02, E03, E05, F04, G01, preferably the isolated antibody or antigen binding fragment thereof is the antibody B06 or B09.

Still preferably, the isolated antibody or antigen binding fragment thereof VH CDR1, CDR2 and CDR3 selected from Table 2 and VL CDR1, CDR2 and CDR3 selected from Table 3.

Yet preferably, the isolated antibody or antigen binding fragment thereof having an affinity constant lower than or equal to $10^{-8}$ M for human IGFBP5.

It is also disclosed an isolated antibody or antigen binding fragment thereof that:

(a) binds specifically to an epitope on IGFBP5, said epitope being the same or similar epitope as the epitope recognized by the monoclonal antibody A09, B06, C02, D10, F05, B09, B11, C11, C12, D12, E02, E03, E05, F04, G01 as defined in Tables 2-8; or (b) cross-competes for binding with the monoclonal antibody A09, B06, C02, D10, F05, B09, B11, C11, C12, D12, E02, E03, E05, F04, G01 as defined in Tables 2-8; or (c) shows the same or similar binding affinity or specificity, or both, as any of A09, B06, C02, D10, F05, B09, B11, C11, C12, D12, E02, E03, E05, F04, G0 as defined in Tables 2-8; or (d) has one or more biological properties of an antibody molecule described herein, e.g., an antibody molecule chosen from, e.g., any of A09, B06, C02, D10, F05, B09, B11, C11, C12, D12, E02, E03, E05, F04, G01 as defined in Tables 2-8 and; or (e) has one or more pharmacokinetic properties of an antibody molecule described herein, e.g., an antibody molecule chosen from, e.g., any of A09, B06, C02, D10, F05, B09, B11, C11, C12, D12, E02, E03, E05, F04, G01 as defined in Tables 2-8.

In a preferred embodiment the isolated antibody or antigen binding fragment as described above:

(a) binds specifically to an epitope on IGFBP5, said epitope being the same or similar epitope as the epitope recognized by the monoclonal antibody A09, B06, C02, D10, F05, B09, B11, C11, C12, D12, E02, E03, E05, F04, G01 as defined in Tables 2-8; or (b) cross-competes for binding with the monoclonal antibody A09, B06, C02, D10, F05, B09, B11, C11, C12, D12, E02, E03, E05, F04, G01 as defined in Tables 2-8; or (c) shows the same or similar binding affinity or specificity, or both, as any of A09, B06, C02, D10, F05, B09, B11, C11, C12, D12, E02, E03, E05, F04, G0 as defined in Tables 2-8; or (d) has one or more biological properties of an antibody molecule described herein, e.g., an antibody molecule chosen from, e.g., any of A09, B06, C02, D10, F05, B09, B11, C11, C12, D12, E02, E03, E05, F04, G01 as defined in Tables 2-8 and; or (e) has one or more pharmacokinetic properties of an antibody molecule described herein, e.g., an antibody molecule chosen from, e.g., any of A09, B06, C02, D10, F05, B09, B11, C11, C12, D12, E02, E03, E05, F04, G01 as defined in Tables 2-8.

Preferably the isolated antibody or antigen binding fragment thereof as defined above is a human or a humanized antibody, preferably it is an IgG2 or IgG4 antibody, preferably an IgG2 kappa antibody, an IgG2 lambda antibody, an IgG4 kappa antibody or an IgG4 lambda antibody.

Preferably the inhibitor as described above reduces or inhibits the binding of IGFBP5 to at least one of its receptors, preferably the at least one receptor is the $\alpha 2\beta 1$ integrin or $\alpha v\beta 6$ integrin.

Still preferably the inhibitor as defined above i) reduces or inhibits extracellular matrix production and/or ii) reduces or inhibits extracellular matrix deposition and/or iii) reduces or inhibits collagen and/or fibronectin production in primary lung fibroblasts and/or iv) reduces or inhibits collagen and/or fibronectin deposition in primary lung fibroblasts.

It is herein disclosed an isolated polynucleotide comprising at least one sequence that encodes the antibody or antigen binding fragment thereof as defined above, preferably said polynucleotide is a cDNA.

It is herein disclosed a vector comprising the polynucleotide as defined above, preferably said vector being selected from the group consisting of a plasmid, a viral vector, a non-episomal mammalian vector, an expression vector and a recombinant expression vector.

It is herein disclosed an isolated cell comprising the polynucleotide or the vector as defined above, preferably said isolated cell being a hybridoma or a Chinese Hamster Ovary (CHO) cell or a Human Embryonic Kidney cells (HEK293).

Preferably the inhibitor, the antibody or antigen binding fragment thereof or the polynucleotide or the vector or the cell as defined above is for use as a medicament, preferably for use in the treatment and/or prevention of fibrosis or of a fibrotic condition, preferably scleroderma or pulmonary fibrosis, preferably morphea, fibrosis as a result of Graft-Versus-Host Disease (GVHD), keloid and hypertrophic scar, subepithelial fibrosis, endomyocardial fibrosis, uterine fibrosis, myelofibrosis, retroperitoneal fibrosis, nephrogenic systemic fibrosis, scarring after surgery, asthma, aberrant wound healing, and multifocal fibrosclerosis, cryptogenic fibrosing alveolitis (CFA), and idiopathic pulmonary fibrosis (IPF).

It is herein disclosed a pharmaceutical composition comprising the inhibitor, isolated antibody or antigen binding fragment thereof or the polynucleotide or the vector or the cell as described above and pharmaceutically acceptable carrier, preferably for use in the treatment of fibrosis or of a fibrotic condition, preferably said composition further comprises a therapeutic agent.

The therapeutic agent may be nintedanib and pirfenidone.

Antibodies and antigen binding fragment thereof are disclosed herein that have anti-fibrotic activity.

In some embodiments, methods are disclosed for inhibiting fibrosis in vivo or in vitro. In additional embodiments, methods are disclosed for the treatment of fibrosis in a subject. In some specific non-limiting examples, the subject has scleroderma or pulmonary fibrosis.

The foregoing and other features and advantages will become more apparent from the following detailed description of several embodiments, which proceeds with reference to the accompanying figures.

DETAILED DESCRIPTION OF THE INVENTION

Figure 1:
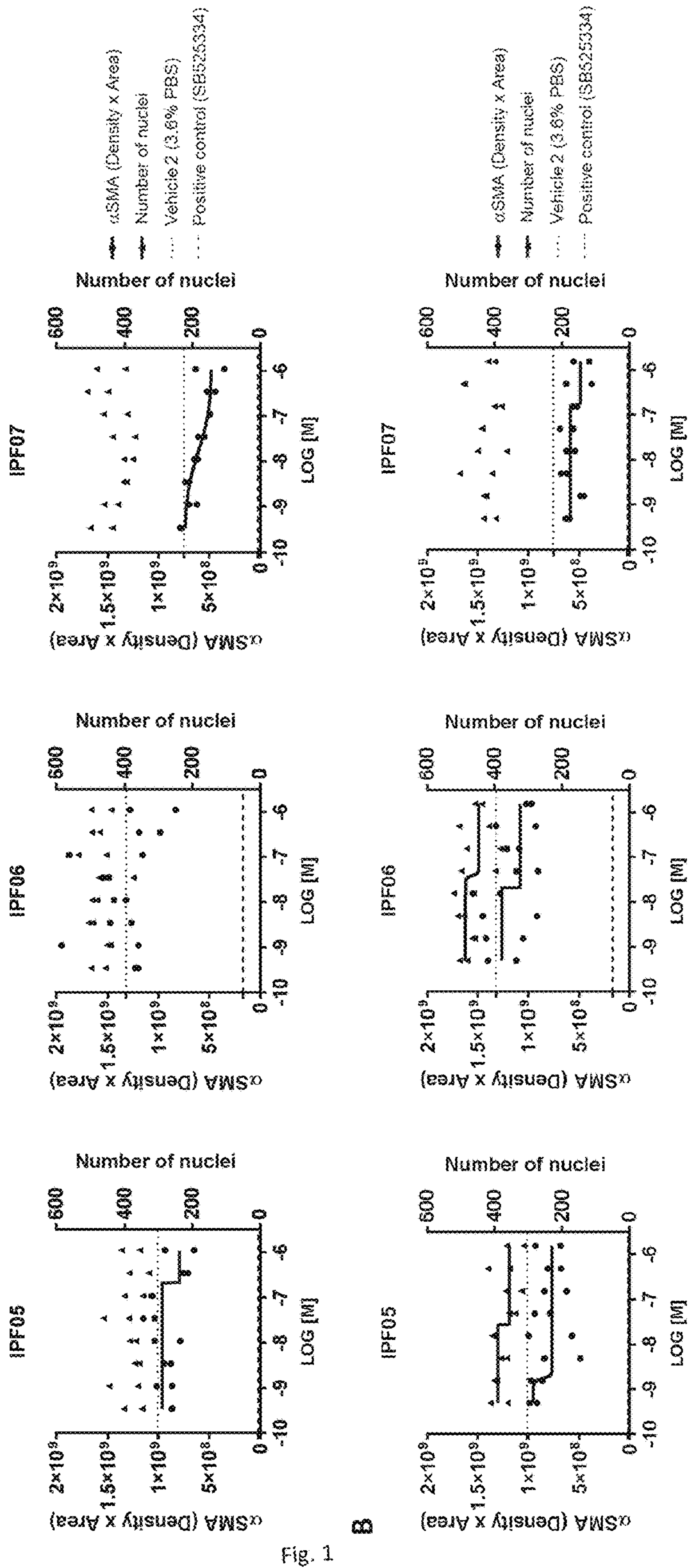
FIG. 1. Effect of anti-IGFBP5 mAbs on Fibroblast-to-Myofibroblast Transition (FMT) assay upon TGF-β1 exposure. Human primary lung fibroblasts from three IPF donors (IPF05, IPF06 and IPF07) were triggered with 1.25 ng/ml of TGF-β1 to induce FMT. The anti-IGFBP5 mAbs, B06 (A) and B09 (B) were tested in an FMT assay to check their capacity to inhibit αSMA expression. Vehicle 2: cells treated with 3.6% PBS and 1.25 ng/ml of TGF-β1.

Unless otherwise noted, technical terms are used according to conventional usage in the art.

The antibodies of the invention specifically bind human IGFBP5.

As discussed herein, these antibodies are collectively referred to as "anti-IGFBP5 antibodies". All of such antibodies are encompassed by the discussion herein. The respective antibodies can be used alone or in combination in the methods of the invention.

By "antibodies that specifically bind" IGFBP5 is intended that the antibodies will not substantially cross react with another, non-homologous, human polypeptide. By "not substantially cross react" is intended that the antibody or fragment has a binding affinity for a non-homologous protein which is less than 10%, more preferably less than 5%, and even more preferably less than 1%, of the binding affinity for IGFBP5.

In various embodiments, an antibody that "specifically binds" IGFBP5, as used herein, includes antibodies that bind human IGFBP5 with a $K_D$ of less than about $10^{-6}$ M, less than about $5\times10^{-7}$ M, less than about $3\times10^{-7}$ M, less than about $2\times10^{-7}$ M, less than about $10^{-7}$ M, less than about $9\times10^{-8}$ M, less than about $8\times10^{-8}$ M, less than about $7\times10^{-8}$ M, less than about $6\times10^{-8}$ M, less than about $5\times10^{-8}$ M, less than about $4\times10^{-8}$ M, less than about $3\times10^{-8}$ M, less than about $2\times10^{-8}$ M, less than about $10^{-8}$ M, less than about $5\times10^{-9}$ M, less than about $4\times10^{-9}$ M, less than about $3\times10^{-9}$ M, less than about $2\times10^{-9}$ M, less than about $10^{-9}$ M or about $5\times10^{-10}$ M, as measured in a surface plasmon resonance assay, for example using the BIAcore™ system (Biacore Life Sciences division of GE Healthcare, Piscataway, NJ) or kinetic exclusion assays or using Biomolecular Interaction Analysis performed by an Octet platform as described herein.

The term "antibody" herein is used in the broadest sense understood in the art, including all polypeptides described as antibodies in Sumit G, Wei W, Tsutomu and Satoshi O, Antibodies 2013; 2:452-500, incorporated herein by reference.

For example, the term "antibody", as used herein encompasses monoclonal antibodies, polyclonal antibodies, monospecific and multi-specific antibodies (e.g., bispecific antibodies), and antibody fragments so long as the fragment exhibits the desired antigen-binding activity (antigen-binding fragments).

The terms "antigen-binding fragment" of an antibody or equivalently "antigen-binding portion" of an antibody and the like, as used herein, include any naturally occurring, enzymatically obtainable, synthetic, or genetically engineered polypeptide or glycoprotein that comprises a portion of an antibody and that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As with full antibody molecules, antigen-binding fragments may be monospecific or multi-specific (e.g., bispecific). A multi-specific antigen-binding fragment of an antibody will typically comprise at least two different antigen binding moieties, wherein each antigen binding moiety is capable of specifically binding to a separate antigen or to a different epitope on the same antigen.

In particular embodiments, an antigen-binding fragment of an antibody comprises at least one variable domain covalently linked to at least one constant domain. Non-limiting, exemplary configurations of variable and constant domains that may be found within an antigen-binding fragment of an antibody include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may in various embodiments consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody may in various embodiments comprise a homodimer or hetero-dimer (or other multimer) of any of the variable and constant domain configurations listed above in non-covalent association with one another and/or with one or more monomeric VH or VL domain (e.g., by disulfide bond(s)).

The term "antigen-binding fragment" of an antibody further includes single domain antibodies.

A single-domain antibody is an antibody fragment consisting of a single monomeric variable antibody domain. In some embodiments, the single-domain antibody is derived from the variable domain of the antibody heavy chain from camelids (also termed nanobodies, or VHH fragments). In some embodiments, the single-domain antibody is an autonomous human heavy chain variable domain (aVH) or VNAR fragments derived from sharks.

Non-limiting examples of antigen-binding fragments include: (i) Fab fragments; (ii) F(ab') 2 fragments; (iii) Fd fragments; (iv) Fv fragments; (v) single-chain Fv (scFV) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, and bivalent nanobodies), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

The term "antibody," as used herein, also includes ADC (antibody drug conjugate) and payload fusion antibodies.

As used herein, the term "antigen binding molecule" refers in its broadest sense to a molecule that specifically binds an antigenic determinant. Examples of antigen binding molecules are antibodies, including antigen-binding antibody fragments, and scaffold antigen binding proteins.

The term "antigen binding moiety" refers to the portion of an antigen binding molecule that specifically binds to an antigenic determinant. Antigen binding moieties include antibodies and antigen-binding fragments thereof, such as scFv, that are capable of specific binding to an antigen on a target cell. In a particular aspect, the antigen binding moiety is able to direct the entity to which it is attached, such as a cell, to a target site. In addition, antigen binding moieties capable of specific binding to a target cell antigen include scaffold antigen binding proteins as defined herein below, e.g. binding domains which are based on designed repeat proteins or designed repeat domains such as designed ankyrin repeat proteins (DARPins) (see e.g. WO 2002/020565) or Lipocalins (Anticalin).

Designed Ankyrin Repeat Proteins (DARPins), which are derived from Ankyrin, which is a family of proteins that mediate attachment of integral membrane proteins to the cytoskeleton. A single ankyrin repeat is a 33-residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100 (4), 1700-1705 (2003) and J. Mol. Biol. 369, 1015-1028 (2007) and US20040132028.

In certain embodiments, antibodies and antigen binding molecules provided herein are altered to increase or decrease the extent to which the antigen binding moiety is glycosylated. Glycosylation variants of the molecules may be conveniently obtained by altering the amino acid sequence such that one or more glycosylation sites is created or removed. Where the antigen binding molecule comprises an Fc region, the carbohydrate attached thereto may be altered. In one aspect, variants of antigen binding molecules are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of antigen binding molecules of the invention include those with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.) and WO 1999/22764 (Raju, S.).

In certain embodiments, it may be desirable to create cysteine engineered variants of the antibody or antigen binding molecule of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the antibody or antigen binding molecules provided herein may be further modified to contain additional non-proteinaceous moieties that are known in the art and readily available. The moieties suitable for derivatization of the antibody or antigen binding molecule include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed. In another aspect, immunoconjugates of the antigen binding molecules provided herein may be obtained. An "immunoconjugate" is an antibody conjugated to one or more heterologous molecule(s), including but not limited to a cytotoxic agent.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity. In certain embodiments, the constant region is an IgG1, IgG2, IgG3, IgG4 constant region.

The instant invention encompasses in various embodiments antibodies having one or more mutations in the hinge, CH2 or CH3 region which may be desirable, for example, in production, to improve the yield of the desired antibody form. In some embodiments, for example, the antibodies described herein comprise a human IgG4 constant region. In particular embodiments, the IgG4 constant region has a single amino acid substitution in the hinge region of the human IgG4 hinge which reduced Fab arm exchange (Angal et al. (1993) Molecular Immunology 30:105) to levels typically observed using a human IgG1 hinge.

In certain embodiments, the antibody comprises one or more mutations in the constant region that increase serum half-life, including those described in U.S. Pat. Nos. 7,083,784, 8,323,962 and Dall'Aqua et al., *J. Biol. Chem.* 281 (33): 23514-23524 (2006); Hinton et al., *J. Immunology* 176:346-356 (2006); Yeung et al., *J. Immunology* 182:7663-7671 (2009); and Petkova et al., *Intn'l Immunology,* 18:1759-1769 (2006), incorporated herein by reference in their entireties.

The term "human antibody", as used herein, is intended to include antibodies having variable and constant regions derived from human germline immunoglobulin sequences. The human antibodies featured in the invention may in various embodiments nonetheless include amino acid residues not encoded by human germline immunoglobulin sequences (e.g., mutations introduced by random or site-specific mutagenesis in vitro or by somatic mutation in vivo), for example in the CDRs and, in some embodiments, CDR3. However, the term "human antibody", as used herein, is not intended to include antibodies in which CDR sequences are derived from the germline of another mammalian species, such as a mouse, which have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." In various embodiments, the isolated antibody also includes an antibody in situ within a recombinant cell. In other embodiments, isolated antibodies are antibodies that have been subjected to at least one purification or isolation step. In various embodiments, an isolated antibody may be substantially free of other cellular material and/or chemicals.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The anti-IGFBP5 antibodies described herein and useful for the methods featured herein may in various embodiments include one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases.

The present invention includes in various embodiments antibodies and methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations").

Numerous antibodies and antigen-binding fragments may be constructed which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies may contain any combination of two or more germline mutations within the framework and/or CDR regions, e.g., wherein certain individual residues are mutated to the corresponding residue of a certain germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes anti-IGFBP5 antibodies and methods involving the use of anti-IGFBP5 antibodies comprising variants of any of the HCVR, LCVR, and/or CDR amino acid sequences disclosed herein having one or more conservative substitutions. For example, the present invention includes the use of anti-IL-6R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. The term "bioequivalent" as used herein, refers to a molecule having similar bioavailability (rate and extent of availability) after administration at the same molar dose and under similar conditions (e.g., same route of administration), such that the effect, with respect to both efficacy and safety, can be expected to be essentially same as the comparator molecule. Two pharmaceutical compositions comprising an anti-IGFBP5 antibody are bioequivalent if they are pharmaceutically equivalent, meaning they contain the same amount of active ingredient (e.g., IGFBP5 antibody), in the same dosage form, for the same route of administration and meeting the same or comparable standards. Bioequivalence can be determined, for example, by an in vivo study comparing a pharmacokinetic parameter for the two compositions. Parameters commonly used in bioequivalence studies include peak plasma concentration (Cmax) and area under the plasma drug concentration time curve (AUC).

The invention in certain embodiments relates to antibodies and methods comprising administering to the subject an antibody which comprises the heavy chain variable region comprising a sequence chosen from the group of: SEQ ID No. 61 to SEQ ID No. 75 and the light chain variable region comprising a sequence chosen from the group of: SEQ ID No. 76 to SEQ ID No. 90. The disclosure provides pharmaceutical compositions comprising such antibody, and methods of using these compositions.

The antibody is administered to the subject in various embodiments in a formulation comprising suitable carriers, excipients, and other agents to provide improved transfer, delivery, tolerance, and the like, and suitable for an intravenous or subcutaneous injection.

The injectable preparations may be prepared by methods publicly known. For example, injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 20 or 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injectable preparation thus prepared can be filled in an appropriate ampoule.

The antibody according to the invention can be administered to the subject using any acceptable device or mechanism. For example, the administration can be accomplished using a syringe and needle or with a reusable pen and/or autoinjector delivery device. The methods of the present invention include the use of numerous reusable pen and/or autoinjector delivery devices to administer an antibody (or pharmaceutical formulation comprising the antibody). Examples of such devices include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen and/or autoinjector delivery devices having applications in subcutaneous delivery of a pharmaceutical composition of the present invention include, but are not limited to, the SOLOSTART pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), the HUMIRA™ Pen (Abbott Labs, Abbott Park, IL), the DAI® Auto Injector (SHL Group) and any auto-injector featuring the PUSH-CLICK™ technology (SHL Group), to name only a few.

In one embodiment, the antibody is administered with a prefilled syringe. In another embodiment, the antibody is administered with a prefilled syringe containing a safety system. For example, the safety system prevents an accidental needlestick injury. In various embodiments, the antibody is administered with a prefilled syringe containing an ÈRIS™ safety system (West Pharmaceutical Services Inc.). See also U.S. Pat. Nos. 5,215,534 and 9,248,242, incorporated herein by reference in their entireties. In another embodiment, the antibody is administered with an auto-injector. In various embodiments, the antibody is administered with an auto-injector featuring the PUSHCLICK™ technology (SHL Group). In various embodiments, the auto-injector is a device comprising a syringe that allows for administration of a dose of the composition and/or antibody to a subject. See also U.S. Pat. Nos. 9,427,531 and 9,566,395, incorporated herein by reference in their entireties.

According to the invention, "subject" means a human subject or human patient.

"Fibrosis" is the formation or development of excess fibrous connective tissue in an organ or tissue as a reparative or reactive process, as opposed to a formation of fibrous tissue as a normal constituent of an organ or tissue. It is the major histopathologic feature of a variety of clinical conditions. Many organs are susceptible to pathological fibrosis, including but not limited to skin, lungs, heart, and the gastrointestinal tract. The invention relates to an inhibitor that specifically targets the pathogenesis of fibrosis, having "anti-fibrotic activity or effects", by targeting IGFBP5, which is a pro-fibrotic mediator.

Fibrosis is defined by accumulation of fibrous connective tissue (components of the extracellular matrix (ECM) such as collagen and fibronectin) in and around inflamed or damaged tissue, which can lead to permanent scarring, organ malfunction and, ultimately, death. Fibrosis is a pathological feature of most chronic inflammatory diseases. Fibrosis affects nearly every tissue in the body. (Schruf et al. Respiratory Research (2019) 20:87).

Following activation by pro-fibrotic stimuli, fibroblasts differentiate into an aggressive phenotype, which secrete excessive amounts of collagen-rich extracellular matrix and thereby constitute the primary pathologic fibroblast phenotype (Geng et al. Respiratory Research (2015) 16:124).

Exemplary fibrotic conditions are scleroderma, idiopathic pulmonary fibrosis, morphea, fibrosis as a result of Graft-Versus-Host Disease (GVHD), keloid and hypertrophic scar, and subepithelial fibrosis, endomyocardial fibrosis, uterine fibrosis, myelofibrosis, retroperitoneal fibrosis, nephrogenic systemic fibrosis, scarring after surgery, asthma, aberrant wound healing, glomerulonephritis, and multifocal fibrosclerosis.

"Idiopathic Pulmonary Fibrosis" is a condition also known as cryptogenic fibrosing alveolitis (CFA) that is a chronic, progressive form of lung disease characterized by fibrosis of the supporting framework (interstitium) of the lungs. By definition, the term is used only when the cause of the pulmonary fibrosis is unknown ("idiopathic"). When lung tissue from patients with IPF is examined under a microscope by a pathologist, it shows a characteristic set of histologic/pathologic features known as usual interstitial pneumonia (UIP). UIP is characterized by progressive scarring of both lung that involves the supporting framework (interstitium) of the lung.

Inhibiting or treating a disease: Inhibiting a disease, such as fibrosis, refers to inhibiting or slowing the full development of a disease. In several examples, inhibiting a disease refers to lessening symptoms of a fibrosis, such as the formation of scar tissue or an increase in range of motion or a decrease in pain. "Treatment" refers to a therapeutic intervention that ameliorates a sign or symptom of a disease or pathological condition related to the disease, such as the fibrosis.

"Scleroderma" is a chronic autoimmune disease characterized by fibrosis (or hardening), vascular alterations, and autoantibodies. There are two major forms, one is a limited systemic scleroderma form that includes limited cutaneous scleroderma-mainly affects the hands, arms and face, although pulmonary hypertension is frequent. While, diffuse cutaneous scleroderma (or systemic sclerosis) is rapidly progressing and affects a large area of the skin and one or more internal organs, frequently the kidneys, esophagus, heart and lungs. Systemic scleroderma in both of its forms can be fatal. Other forms of scleroderma include systemic scleroderma, which lacks skin changes with systemic manifestations and two localized form that affect the skin, but not internal organs: morphea and linear scleroderma. The disclosed antibodies can be used to treat any form of scleroderma.

Therapeutic Methods and Pharmaceutical Compositions

The antibodies disclosed herein can be used to treat fibrosis occurring in several disease conditions. The antibodies disclosed herein may decrease fibrosis that has already occurred, resolving existing fibrosis and/or may decrease the rate or amount of additional fibrosis. In several examples, the antibodies are of use to decrease fibrosis in pathogenic processes, such as in a subject Thus, in several embodiments, the methods include administering to a subject a therapeutically effective amount of one or more of the antibodies disclosed herein, in order to decrease fibrosis. Any of the antibodies disclosed herein can be used to decrease fibrosis. In some embodiments, the antibodies can be administered as a unit dose.

Suitable subjects include those with a fibrosis of the skin or lungs, but fibrosis of any tissue can be treated using the methods disclosed herein. In one example, the subject has scleroderma. In other examples, the subject has idiopathic pulmonary fibrosis, morphea, fibrosis as a result of Graft-Versus-Host Disease (GVHD), a keloid or hypertrophic scar, subepithelial fibrosis, endomyocardial fibrosis, uterine fibrosis, myelofibrosis, retroperitoneal fibrosis, nephrogenic systemic fibrosis, scarring after surgery, asthma, aberrant wound healing, glomerulonephritis, and multifocal fibrosclerosis.

In further examples, the methods are used to treat the systemic form of scleroderma, such as limited cutaneous scleroderma or diffuse cutaneous scleroderma (or systemic sclerosis). The methods can be used to treat the localized form of scleroderma, including morphea and linear scleroderma.

The methods can include selecting a subject in need of treatment, such as a subject with a fibrotic disease, such as scleroderma, idiopathic pulmonary fibrosis, morphea, a keloid scar, a hypertrophic scar, or subepithelial fibrosis. In exemplary applications, compositions are administered to a subject having a fibrotic disease, such as scleroderma, idiopathic pulmonary fibrosis, morphea, a keloid scar, a hypertrophic scar, or subepithelial fibrosis, or any of the disorders listed above, in an amount sufficient to reduce the fibrosis. Amounts effective for this use will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer.

A method is provided herein for decreasing skin thickness. The method includes administering a therapeutically effective amount of an antibody, thereby decreasing skin thickness. In another embodiment, and methods is provided for decreasing lung fibrosis. The method includes administering a therapeutically effective amount of an antibody, thereby decreasing skin thickness. Any of the antibody disclosed herein can be used in these methods.

Methods are provided herein for decreasing αSMA or FN1 expression, such as transforming growth factor (TGF)-β induced αSMA or FN1 expression. The method includes contacting a cell with an effective amount of an antibody, thereby decreasing αSMA or FN1 expression. The methods can be practiced in vivo or in vitro. In some embodiments, the methods include comparing the amount of αSMA or FN1 expression produced by a cell contacted with an antibody to a control. The control can be a standard value, or the amount of αSMA or FN1 produced by a cell not contacted with the antibody, such as a cell contacted with a carrier.

An antibody herein disclosed can be administered by any means known to one of skill in the art either locally or systemically, such as by intradermal, intrathecal, intramuscular, subcutaneous, intraperitoneal or intravenous injection, but even oral, nasal, transdermal or anal administration is contemplated. In one embodiment, administration is by subcutaneous, intradermal, or intramuscular injection. In another embodiment, administration is by intraperitoneal or intrathecal administration. To extend the time during which the antibody is available to stimulate a response, the antibody can be provided as an implant, an oily injection, or as a particulate system. The particulate system can be a microparticle, a microcapsule, a microsphere, a nanocapsule, or similar particle. (see, e.g., Banga, supra).

For treatment of the skin, a therapeutically effective amount of at least antibody can be locally administered to the affected area of the skin, such as in the form of an ointment (RGA Jones and A Marino, "Targeted localized use of therapeutic antibodies: a review of non-systemic, topical and oral applications, *Crit. Rev. Biotechnol.* 36 (3): 506-520 (2016).

In one embodiment, the ointment is an entirely homogenous semi-solid external agent with a firmness appropriate for easy application to the skin. Such an ointment can include fats, fatty oils, lanoline, Vaseline, paraffin, wax, hard ointments, resins, plastics, glycols, higher alcohols, glycerol, water or emulsifier and a suspending agent. Using these ingredients as a base, a decoy compound can be evenly mixed. Depending on the base, the mixture can be in the form of an oleaginous ointment, an emulsified ointment, or a water-soluble ointment oleaginous ointments use bases such as plant and animal oils and fats, wax, Vaseline and liquid paraffin. Emulsified ointments are comprised of an oleaginous substance and water, emulsified with an emulsifier. They can take either an oil-in-water form (O/W) or a water-in-oil-form (W/O). The oil-in-water form (O/W) can be a hydrophilic ointment. The water-in-oil form (W/O) initially lacks an aqueous phase and can include hydrophilic Vaseline and purified lanoline, or it can contain a water-absorption ointment (including an aqueous phase) and hydrated lanoline. A water-soluble ointment can contain a completely water-soluble Macrogol base as its main ingredient.

Pharmaceutically acceptable carriers include a petroleum jelly, such as VASELINE®, wherein the petroleum jelly contains 5% stearyl alcohol, or petroleum jelly alone, or petroleum jelly containing liquid paraffin. Such carriers enable pharmaceutical compositions to be prescribed in forms appropriate for consumption, such as tablets, pills, sugar-coated agents, capsules, liquid preparations, gels, ointments, syrups, slurries, and suspensions. When locally administered into cells in an affected area or a tissue of interest, the at least one C-terminal endostatin polypeptide, or polynucleotide encoding the peptide can be administered in a composition that contains a synthetic or natural hydrophilic polymer as the carrier. Examples of such polymers include hydroxypropyl cellulose and polyethylene glycol. One or more antibody can be mixed with a hydrophilic polymer in an appropriate solvent. The solvent is then removed by methods such as air-drying, and the remainder is then shaped into a desired form (for example, a sheet) and applied to the target site. Formulations containing such hydrophilic polymers keep well as they have a low water-content. At the time of use, they absorb water, becoming gels that also store well. In the case of sheets, the firmness can be adjusted by mixing a polyhydric alcohol with a hydrophilic polymer similar to those above, such as cellulose, starch and its derivatives, or synthetic polymeric compounds. Hydrophilic sheets thus formed can be used. A therapeutically effective amount of one or more antibodies can also be incorporated into bandages and dressings.

For administration by inhalation, the antibody can be conveniently delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

In some embodiments, the antibody, can be administered by inhalation. For example, it can be administered in an aerosolized form, such as using a nebulizer or a metered dose inhaler. Technologies of use include micropump nebulizers (such as the AEROGEN GO® system), jet nebulizers designed to produce large fine particle fractions (such as the PARI LC STAR®), jet nebulizers developing less shear during atomization (such as the HUDSON MICROMISTR), and ultrasonic nebulizers (such as the DeVilbiss ULTRA-NEB®).

The antibody can be dissolved in a carrier, such as saline, and atomized using the devices above. The associated aerosols can be collected using a NEXT GENERATION IMPACTOR® (NGI) (MSP Corp., Shoreview, Minn.), which uses a series of aerodynamic stages to separate and collect the aerosol into separate fractions based on droplet size. Since droplet size is the primary determinant of deposition location in the lungs, this device allows us to specifically isolate the portion of the liquid aerosol that will deposit in the small airways and alveoli.

Aerosol particle size is often expressed in terms of mass median aerodynamic diameter (MMAD), a parameter that is based on particle size, shape, and density. For a spherical particle, MMAD is equal to MMD (p<1/2>), in which MMD is mass median diameter and r is the bulk density. For a non-spherical particle, MMAD is equal to MMD (p/x)<1/2>, in which X is the shape factor. Thus, particles with larger than unit density will have actual diameters smaller than their MMAD.

The site of particle deposition within the respiratory tract is demarcated based on particle size. In one example, particles of about 1 to about 500 microns are utilized, such as particles of about 25 to about 250 microns, or about 10 to about 25 microns are utilized. In other embodiments, particles of about 1 to 50 microns are utilized. For use in a metered dose inhaler, for administration to lungs particles of less than about 10 microns, such as particles of about 2 to about 8 microns, such as about 1 to about 5 microns, such as particles of 2 to 3 microns, can be utilized.

A therapeutically effect amount of an antibody can be administered in the pharmaceutically acceptable carrier. Pharmacologically acceptable carriers (e.g., physiologically or pharmaceutically acceptable carriers) are well known in the art, and include, but are not limited to buffered solutions as a physiological pH (e.g. from a pH of about 7.0 to about 8.0, or at a pH of about 7.4). One specific, non-limiting example of a physiologically compatible buffered solution is phosphate buffered saline. Other pharmacologically acceptable carriers include penetrants, which are particularly suitable for pharmaceutical formulations that are intended to be topically applied (for example in the application of surgical wounds to promote healing).

The pharmacological compositions disclosed herein facilitate the use of at least one antibody, either in vivo or ex vivo, to decrease fibrosis. Such a composition can be suitable for delivery of the active ingredient to any suitable subject, and can be manufactured in a manner that is itself known, e.g., by means of conventional mixing, dissolving, granulating, emulsifying, encapsulating, entrapping or lyophilizing processes. Pharmacological compositions can be formulated in a conventional manner using one or more pharmacologically (e.g., physiologically or pharmaceutically) acceptable carriers, as well as optional auxiliaries that facilitate processing of the active compounds into preparations which can be used pharmaceutically. Proper formulation is dependent upon the route of administration chosen. Thus, for injection, the active ingredient can be formulated in aqueous solutions. For transmucosal administration, penetrants appropriate to the barrier to be permeated are used in the formulation. Such penetrants are generally known in the art.

For oral administration, the active ingredient can be combined with carriers suitable for incorporation into tablets, pills, capsules, liquids, gels, syrups, slurries, suspensions and the like. The active ingredient can be formulated for parenteral administration by injection, such as by bolus injection or continuous infusion. Such compositions can take such forms as suspensions, solutions or emulsions in oily or aqueous vehicles, and can contain formulatory agents such as suspending, stabilizing and/or dispersing agents. Other pharmacological excipients are known in the art.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art. They include polymer-based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the at least one C-terminal endostatin polypeptide, or polynucleotide encoding the peptide is contained in a form within a matrix such as those described in U.S. Pat. Nos. 4,452,775; 4,667,014; 4,748,034; 5,239,660; and 6,218,371 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Use of a long-term sustained release implant may be particularly suitable for treatment of chronic conditions, such as scleroderma. Long-term release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. These systems have been described for use with oligodeoxynucleotides (see U.S. Pat. No. 6,218,371). For use in vivo, nucleic acids and peptides are preferably relatively resistant to degradation (such as via endo- and exo-nucleases). Thus, modifications, such as the inclusion of a C-terminal amide, can be used.

The therapeutically effective amount of the antibody will be dependent on the antibody that is utilized, the subject being treated, the severity and type of the affliction, and the manner of administration. For example, a therapeutically effective amount of an antibody can vary from about 0.01 μg per kilogram (kg) body weight to about 1 g per kg body weight, such as about 1 μg to about 5 mg per kg body weight, or about 5 μg to about 1 mg per kg body weight. The exact dose is readily determined by one of skill in the art based on the potency of the specific compound the age, weight, sex and physiological condition of the subject.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

In a further method, an additional agent is administered. In one example, this administration is sequential. In other examples, the additional agent is administered simultaneously with the antibody.

For the treatment of scleroderma, examples of additional agents that can be used with the antibody include nifedipine, amlodipine, diltiazem, felodipine, or nicardipine. An investigational drug Gleevec, is also used for the treatment of scleroderma. Gleevec or other tyrosine kinase inhibitors can be used with the antibodies disclosed herein. Patients with lung involvement of scleroderma benefit from oxygen therapy; the C-terminal endostatin polypeptides disclosed herein can be administered with this therapy. For the treatment of fibrosis of the skin and scleroderma, additional agents of use are d-penicillamine, colchicine, Relaxin, steroids, and cyclosporine. In some embodiments, the additional agent is SAR100842 (see Allanore et al., *Arthr. Rheum.* 70 (10): 1634-1643 (2018)). C-terminal endostatin polypeptides also can be used in combination with immunosuppressive agents. Additionally, the antibodies can be used with methotrexate, cyclophosphamide, azathioprine, mycophenolate, glitazones, endothelin receptor antagonists, or Fulvestrant (ICI-182,780).

The disclosure is illustrated by the following non-limiting Examples.

EXAMPLES

Example 1: Monoclonal Antibodies Development

Monoclonal anti-IGFBP5 antibodies were discovered from naïve human phage-display libraries. First, unspecific or cross-reactive antibody-phage was cleared from the library. For that purpose, the library was incubated in presence of: a) Streptavidin-Beads and BSA, or b) Streptavidin-Beads and BSA, IGFBP1 (R&D, cat n° 871-B1), IGFBP2 (R&D, cat n° 674-B2), IGFBP3 (R&D, cat n° 675-B3), IGFBP4 (R&D, cat n° 804-GB) and IGFBP6 (R&D, cat n° 876-B6).

Antibody-phage that bound to the negative antigens were removed from further selection. After that, the cleared library was selected for target antigen-specific antibodies. First, biotinylated IGFBP5 (R&D, human: cat n° 875-B5, mouse: cat n° 578-B5) was added in presence of the negative antigens to the library preparations a) and b). Antibody-phage that bound to the biotinylated target antigen were captured and recovered from the solution using magnetic streptavidin beads. The beads were washed multiple times with a BSA solution (containing 0.05% Tween20) and BSA in order to remove unspecific or weakly bound antibody-phage particles. Antigen-specific antibody phage were eluted from the beads by Trypsin treatment and rescued by *E. coli* infection. After short propagation, the bacteria were coinfected with M13K07 helper phage and antibody-phage amplification was induced. The amplified phage were used for two more selection cycles as described above. An overview of the antibody selection strategies is given in Table 1:

TABLE 1

| Overview of the antibody selection strategy | | | |
|---|---|---|---|
| Negative selection in selection cycle 1-3 | Positive selection in selection cycle 1 | Positive selection in selection cycle 2 | Positive selection in selection cycle 3 |
| a) Streptavidin-Beads, BSA | Human IGFBP5 | Human IGFBP5 | Human IGFBP5 or Mouse IGFBP5 |
| b) Streptavidin-Beads, BSA, IGFBP1, IGFBP2, IGFBP3, IGFBP4, IGFBP6 | Human IGFBP5 | Human IGFBP5 | Human IGFBP5 or Mouse IGFBP5 |

At the end of the discovery process, each selection output was screened for antigen-specific antibodies and the binding characteristics of monoclonal antibody clones was analysed. For this purpose, 3072 single colonies were used for scFv antibody production. These were then tested for specific antigen binding by ELISA on Streptavidin+biotinylated human IGFBP5, Streptavidin+biotinylated murine IGFBP5, Streptavidin and BSA and 842 clones showed cross-reactive binding between human and murine IGFBP5 with a S/N ratio of >10. 192 of those ELISA positive clones were selected for a secondary screening. For that purpose, a second batch of scFv were produced and tested on a broader panel of antigens: Streptavidin+biotinylated human IGFBP5, Streptavidin+biotinylated murine IGFBP5, Streptavidin, BSA, Human IGFBP1, Human IGFBP2, Human IGFBP3, Human IGFBP4, Human IGFBP5 and Human IGFBP6. 17 lead antibody clones were identified that showed binding to the Streptavidin-captured and directly immobilized human and murine IGFBP5. Binding to human IGFBP1, human IGFBP2, human IGFBP3, human IGFBP4 and human IGFBP6 was not detected. DNA sequence analysis of the 17 lead antibody clones revealed presence of 15 candidates with a unique antibody sequence (≥1 amino acid difference in the CDRs). The scFv DNA sequence was amplified by PCR and cloned into YUMAB's mammalian scFv-Fc expression vector, resulting in a genetic fusion of the scFv with a human IgG4 Fc. Bacterial clones with a correctly cloned scFv gene were used for isolation of transfection grade DNA. The DNA was used for the transient transfection of HEK cells which produced and secreted the antibody into the culture medium. The antibodies were purified by affinity chromatography (Protein A) and re-buffered in PBS. The protein concentration was determined by UV/VIS spectrometry and purity was checked by Coomassie staining. 13 of the 15 antibodies could be successfully produced in the scFv-Fc format.

The sequences of the 15 novel anti-IGFBP5 antibodies are reported in Tables 2-8.

TABLE 2

| VH CDR Sequences of exemplified antibodies (Kabat definitions) | | | |
|---|---|---|---|
| Antibody | VH CDR1 | VH CDR2 | VH CDR3 |
| A09 | SYGIS (SEQ ID No. 1) | WISAYNGNTNYAQKLQG (SEQ ID No. 6) | EWELLGGLDY (SEQ ID No. 12) |
| B06 | SYAMS (SEQ ID No. 2) | AISGSGGSTYYADSVKG (SEQ ID No. 7) | GAGTLDY (SEQ ID No. 13) |
| C02 | SYGIS (SEQ ID No. 1) | WISAYNGNTNYAQKLQG (SEQ ID No. 6) | GRGVIDY (SEQ ID No. 14) |
| D10 | SYGIS (SEQ ID No. 1) | WISAYNGNTNYAQKLQG (SEQ ID No. 6) | DRYLGWFDP (SEQ ID No. 15) |
| F05 | SYGIS (SEQ ID No. 1) | WISAYNGNTNYAQKLQG (SEQ ID No. 6) | GRGSFDP (SEQ ID No. 16) |
| B09 | SYGIS (SEQ ID No. 1) | WISAYNGNTNYAQKLQG (SEQ ID No. 6) | DLAVGTHGDY (SEQ ID No. 17) |
| B11 | SYAIS (SEQ ID No. 3) | GIIPIFGTANYAQKFQG (SEQ ID No. 8) | NVRLPGWFDP (SEQ ID No. 18) |
| C11 | SYGMH (SEQ ID No. 4) | VISYDGSNKYYADSVKG (SEQ ID No. 9) | GDYSDTSGTDFFQH (SEQ ID No. 19) |
| C12 | SYAIS (SEQ ID No. 3) | GIIPIFGTANYAQKFQG (SEQ ID No. 8) | LGRELSFDY (SEQ ID No. 20) |
| D12 | SYAIS (SEQ ID No. 3) | GIIPIFGTANYAQKFQG (SEQ ID No. 8) | FGRPQLGYAFDI (SEQ ID No. 21) |
| E02 | SYAIS (SEQ ID No. 3) | GIIPIFGTANYAQKFQG (SEQ ID No. 8) | MSVAGPSISFDY (SEQ ID No. 22) |

TABLE 2-continued

VH CDR Sequences of exemplified antibodies (Kabat definitions)

| Antibody | VH CDR1 | VH CDR2 | VH CDR3 |
|---|---|---|---|
| E03 | SYAIS (SEQ ID No. 3) | GITPIFGTANYAQKFQG (SEQ ID No. 10) | AGILTGYYFDY (SEQ ID No. 23) |
| E05 | GYGMN (SEQ ID No. 5) | YVGSSSSTIYYADSVKG (SEQ ID No. 11) | GLGGN (SEQ ID No. 24) |
| F04 | SYGMH (SEQ ID No. 4) | VISYDGSNKYYADSVKG (SEQ ID No. 9) | LSGPNGVDY (SEQ ID No. 25) |
| G01 | SYAIS (SEQ ID No. 3) | GIIPIFGTANYAQKFQG (SEQ ID No. 8) | ITEGAFDY (SEQ ID No. 26) |

TABLE 3

VL CDR sequences of exemplified antibodies (Kabat definitions)

| Antibody | VL CDR1 | VL CDR2 | VL CDR3 |
|---|---|---|---|
| A09 | TGTSSDVGGYNYVS (SEQ ID No. 27) | EVSNRPS (SEQ ID No. 37) | SSYTSSSTVV (SEQ ID No. 48) |
| B06 | KSSQSVLYSSNNKNYLS (SEQ ID No. 28) | WASTRES (SEQ ID No. 38) | QQYYSTPLT (SEQ ID No. 49) |
| C02 | KSSQSVLYSSNNKNYLA (SEQ ID No. 29) | WASTRES (SEQ ID No. 38) | QQYYSTPLT (SEQ ID No. 49) |
| D10 | TGTSSDVGGYNYVS (SEQ ID No. 27) | EVSNRPS (SEQ ID No. 39) | SSYTSSSTPYV (SEQ ID No. 50) |
| F05 | KSSQSVLYSSNNKNYLA (SEQ ID No. 29) | WASTRES (SEQ ID No. 38) | QQYYSTPLT (SEQ ID No. 49) |
| B09 | TGTSSDVGGYNYVS (SEQ ID No. 27) | EVSNRPS (SEQ ID No. 39) | SSYTSSSTLEVV (SEQ ID No. 51) |
| B11 | RASQSISSWLA (SEQ ID No. 30) | KASSLES (SEQ ID No. 40) | QQYNSYPLT (SEQ ID No. 52) |
| C11 | RASQSISSYLN (SEQ ID No. 31) | AASSLQS (SEQ ID No. 41) | QQSYSTPG (SEQ ID No. 53) |
| C12 | RASQSISSYLN (SEQ ID No. 31) | AASSLQS (SEQ ID No. 41) | QQSYSESWT (SEQ ID No. 54) |
| D12 | RASQSLSADYLA (SEQ ID No. 32) | GASTRAT (SEQ ID No. 42) | QQNDNWPYT (SEQ ID No. 55) |
| E02 | RASQSISSYLN (SEQ ID No. 31) | AASSLQR (SEQ ID No. 43) | QETYSNLWT (SEQ ID No. 56) |
| E03 | TRSSGSIASNYVQ (SEQ ID No. 33) | EDNQRPS (SEQ ID No. 44) | QSYDSSNRPWV (SEQ ID No. 57) |
| E05 | SGSRSNIGSNYVH (SEQ ID No. 34) | RNDQRPS (SEQ ID No. 45) | AAWDDGLSVL (SEQ ID No. 58) |
| F04 | QGDSVRKYYTN (SEQ ID No. 35) | GKNYRPS (SEQ ID No. 46) | HSRDTSDIHLNV (SEQ ID No. 59) |
| G01 | RASRTVGSWLA (SEQ ID No. 36) | DASNLQS (SEQ ID No. 47) | QQYNSSPYT (SEQ ID No. 60) |

TABLE 4

| VH amino acid sequences of exemplified antibodies | |
|---|---|
| Antibody | AA of VH |
| A09 | QVQLVESGAEVKKPGASVKVSCKASGYTFTSYGISWVRQAPGQGLEWMGWISAYNGNTNYAQKLQGRVTMTTDTSTSTAYMELRSLRSDDTAVYYCAREWELLGGLDYWGQGTLVTVSS (SEQ ID No. 61) |
| B06 | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARGAGTLDYWGQGTLVTVSS (SEQ ID No. 62) |
| C02 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARGRGVIDYWGQGTLVTVSS (SEQ ID No. 63) |
| D10 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARDRYLGWFDPWGQGTLVTVSS (SEQ ID No. 64) |
| F05 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARGRGSFDPWGQGTLVTVSS (SEQ ID No. 65) |
| B09 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARDLAVGTHGDYWGQGTLVTVSS (SEQ ID No. 66) |
| B11 | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCARNVRLPGWFDPWGQGTLVTVSS (SEQ ID No. 67) |
| C11 | EVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCARGDYSDTSGTDFFQHWGQGTQVTVSS (SEQ ID No. 68) |
| C12 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCATLGRELSFDYWGQGTLVTVSS (SEQ ID No. 69) |
| D12 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARFGRPQLGYAFDIWGQGTMVTVSS (SEQ ID No. 70) |
| E02 | QMQLVQSGAEVKKPGSSVKVSCKASGGTFSSYAISWVRQAPGQGLEWMGGIIPIFGTANYAQKFQGRVTITADESTSTAYMELSSLRSEDTAVYYCATMSVAGPSISFDYWGQGTLVTVSS (SEQ ID No. 71) |
| E03 | QVQLVQSGAEVKKPGSSVKVSCKASGGTFSSYAISWVRQAPGQGLEWMGGITPIFGTANYAQKFQGRVTITADESTSTAYMELSSLRSEDTAVYYCARAGILTGYYFDYWGQGTLVTVSS (SEQ ID No. 72) |
| E05 | EVQLVESGGGLVQPGGSLKLSCAASGFTFSGYGMNWVRQAPGKGLEWVSYVGSSSSTIYYADSVKGRFTISRDNANNSLYLQMNSLRAEDTAVYYCARGLGGNWGQGTMVTVSS (SEQ ID No. 73) |
| F04 | EVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAKLSGPNGVDYWGQGTLVTVSS (SEQ ID No. 74) |
| G01 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCASITEGAFDYWGQGTLVTVSS (SEQ ID No. 75) |

TABLE 5

| VL amino acid sequences of exemplified antibodies | |
|---|---|
| Antibody | AA of VL |
| A09 | QSALTQPASVSGSPGQSITISCTGTSSDVGGYNYVSWYQQHPGKAPKLMIYEVSNRPSGVSNRFSGSKSGNTASLTISGLQAEDEADYYCSSYTSSSTVVFGGGTKLTVL (SEQ ID No. 76) |
| B06 | DIVMTQSPDSLAVSLGERATINCKSSQSVLYSSNNKNYLSWYQQKPGQPPKLLIYWASTRESGVPDRFSGSGSGTDFTLTISSLQAEDVAVYYCQQYYSTPLTFGGGTKVEIK (SEQ ID No. 77) |

TABLE 5-continued

VL amino acid sequences of exemplified antibodies

| Antibody | AA of VL |
|---|---|
| C02 | EIVMTQSPDSLAVSLGERATINCKSSQSVLYSSNNKNYLAWYQQKPGQPPKLLIYWA STRESGVPDRFSGSGSGTDFTLTISSLQAEDVAVYYCQQYYSTPLTFGGGTKVDIK (SEQ ID No. 78) |
| D10 | QSALTQPASVSGSPGQSITISCTGTSSDVGGYNYVSWYQQHPGKAPKLMIYEVSNR PSGVSNRFSGSKSGNTASLTISGLQAEDEADYYCSSYTSSSTPYVFGTGTKLTVL (SEQ ID No. 79) |
| F05 | DIQLTQSPDSLAVSLGERATINCKSSQSVLYSSNNKNYLAWYQQKPGQPPKLLIYWA STRESGVPDRFSGSGSGTDFTLTISSLQAEDVAVYYCQQYYSTPLTFGGGTKVEIK (SEQ ID No. 80) |
| B09 | QSALTQPASVSGSPGQSITISCTGTSSDVGGYNYVSWYQQHPGKAPKLMIYEVSNR PSGVSNRFSGSKSGNTASLTISGLQAEDEADYYCSSYTSSSTLEVVFGGGTKLTVL (SEQ ID No. 81) |
| B11 | DIQMTQSPSTLSASVGDRVTITCRASQSISSWLAWYQQKPGKAPKLLIYKASSLESG VPSRFSGSGSGTEFTLTISSLQPDDFATYYCQQYNSYPLTFGGGTKVEIK (SEQ ID No. 82) |
| C11 | DIVMTQSPSSLSASVGDRVTITCRASQSISSYLNWYQQKPGKAPKLLIYAASSLQSG VPSRFSGSGSGTDFTLTISSLQPEDFATYYCQQSYSTPGFGGGTKVEIK (SEQ ID No. 83) |
| C12 | DIVMTQSPSSLSASVGDRVTITCRASQSISSYLNWYQQKPGKAPKLLIYAASSLQSG VPSRFSGSGSGTDFTLTISSLQPEDFATYYCQQSYSESWTFGQGTTVDIK (SEQ ID No. 84) |
| D12 | ETTLTQSPGTLSVSPGDRATLSCRASQSLSADYLAWYQQKPGQAPRLLIYGASTRA TGIPARFSGSGSGTEFTLTVSSLQSEDFAVYYCQQNDNWPYTFGQGTKLEIK (SEQ ID No. 85) |
| E02 | DIQMTQSPSSLSASVGDRVAIPCRASQSISSYLNWYQQKPGKAPKLLIYAASSLQRG VPSRFSGSGSGTDFTLTISSLQPEDFATYYCQETYSNLWTFGQGTKVEIK (SEQ ID No. 86) |
| E03 | NFMLTQPHSVSESPGKTVTISCTRSSGSIASNYVQWYQQRPGSSPTTVIYEDNQRP SGVPDRFSGSIDSSSNSASLTISGLKTEDEADYYCQSYDSSNRPWVFGGGTKLTVL (SEQ ID No. 87) |
| E05 | QPGLTQPPSASGAPGQRVTISCSGSRSNIGSNYVHWYQQLPGTAPKLIIYRNDQRP SGVPARFSASKSGTSASLAISGLRSEDEADYYCAAWDDGLSVLFGGGTKLTVL (SEQ ID No. 88) |
| F04 | SSELTQDPSVSVALGQTVTITCQGDSVRKYYTNWYQQKPGQAPILVLYGKNYRPSG IPDRFSGSTSGDTAYLTITGAQAEDAADYYCHSRDTSDIHLNVFGTGTKVTVL (SEQ ID No. 89) |
| G01 | AIQLTQSPSTLSASVGDRVTITCRASRTVGSWLAWYQQKPGKAPKLLIYDASNLQSG VPSRFSGSGSGTEFTLTISSLQPDDLSTYYCQQYNSSPYTFGQGTKVEIK (SEQ ID No. 90) |

CDR definitions are also provided using the annotation tool from http://www.abysis.org/based on full VH and VL amino acid sequences as defined in Tables 4 and 5. For example, the VH or VL amino acid sequence of any antibody disclosed herein is plugged into the annotation tool and Kabat defined CDR sequences, or IMGT, or Chothia, or AbM or Contact defined CDR sequences are provided. Using the “All, side by side” feature, defined CDR sequences are provided.

Table 4.1 shows such sequences related to B06 VH and VL.

TABLE 4.1

B-06 VH and VL CDRs according to different definitions as sorted by inserting aa VH (SEQ ID No. 62) and VL (SEQ ID No. 77) sequence in the www.abysis.org annotation tool.

| $V_H$ | | | | | |
|---|---|---|---|---|---|
| Region | Definition | SEQ ID NO: | Sequence Fragment | Residues | Length |
| CDR-H1 | Chothia | 126 | GFTFSSY--- | 26-32 | 7 |
| | AbM | 127 | GFTFSSYAMS | 26-35 | 10 |

TABLE 4.1-continued

B-06 VH and VL CDRs according to different definitions as sorted by inserting aa VH (SEQ ID No. 62) and VL (SEQ ID No. 77) sequence in the www.abysis.org annotation tool.

| Region | Definition | SEQ ID NO: | Sequence Fragment | Residues | Length |
|---|---|---|---|---|---|
| | Kabat | 2 | -----SYAMS | 31-35 | 5 |
| | Contact | 128 | ----SSYAMS | 30-35 | 6 |
| | IMGT | 129 | GFTFSSYA-- | 26-33 | 8 |
| CDR-H2 | Chothia | 130 | -----SGSGGS--------- | 52-57 | 6 |
| | AbM | 131 | ---AISGSGGSTY------- | 50-59 | 10 |
| | Kabat | 7 | ---AISGSGGSTYYADSVKG | 50-66 | 17 |
| | Contact | 132 | WVSAISGSGGSTY --- | 47-59 | 13 |
| | IMGT | 133 | ----ISGSGGST-------- | 51-58 | 8 |
| CDR-H3 | Chothia | 13 | --GAGTLDY | 99-105 | 7 |
| | AbM | 13 | --GAGTLDY | 99-105 | 7 |
| | Kabat | 13 | --GAGTLDY | 99-105 | 7 |
| | Contact | 134 | ARGAGTLD- | 97-104 | 8 |
| | IMGT | 135 | ARGAGTLDY | 97-105 | 9 |

$V_L$

| Region | Definition | SEQ ID NO: | Sequence Fragment | Residues | Length |
|---|---|---|---|---|---|
| CDR-L1 | Chothia | 28 | KSSQSVLYSSNNKNYLS-- | 24-40 | 17 |
| | AbM | 28 | KSSQSVLYSSNNKNYLS-- | 24-40 | 17 |
| | Kabat | 28 | KSSQSVLYSSNNKNYLS-- | 24-40 | 17 |
| | Contact | 136 | ------LYSSNNKNYLSWY | 30-42 | 13 |
| | IMGT | 137 | ---QSVLYSSNNKNY---- | 27-38 | 12 |
| CDR-L2 | Chothia | 38 | ----WASTRES | 56-62 | 7 |
| | AbM | 38 | ----WASTRES | 56-62 | 7 |
| | Kabat | 38 | ----WASTRES | 56-62 | 7 |
| | Contact | 138 | LLIYWASTRE- | 52-61 | 10 |
| | IMGT | | ----WA----- | 56-57 | 2 |
| CDR-L3 | Chothia | 49 | QQYYSTPLT | 95-103 | 9 |
| | AbM | 49 | QQYYSTPLT | 95-103 | 9 |
| | Kabat | 49 | QQYYSTPLT | 95-103 | 9 |
| | Contact | 139 | QQYYSTPL- | 95-102 | 8 |
| | IMGT | 49 | QQYYSTPLT | 95-103 | 9 |

Table 5.1 shows such sequences related to B09 VH and VL.

TABLE 5.1

B-09 VH and VL CDRs according to different definitions as sorted by inserting aa VH (SEQ ID No. 66) and VL (SEQ ID No. 81) sequence in the www.abysis.org annotation tool.

$V_H$

| Region | Definition | SEQ ID NO: | Sequence Fragment | Residues | Length |
|---|---|---|---|---|---|
| CDR-H1 | Chothia | 140 | GYTFTSY--- | 26-32 | 7 |
| | AbM | 141 | GYTFTSYGIS | 26-35 | 10 |
| | Kabat | 1 | -----SYGIS | 31-35 | 5 |
| | Contact | 142 | ----TSYGIS | 30-35 | 6 |
| | IMGT | 143 | GYTFTSYG-- | 26-33 | 8 |
| CDR-H2 | Chothia | 144 | -----SAYNGN--------- | 52-57 | 6 |
| | AbM | 145 | ---WISAYNGNTN------- | 50-59 | 10 |
| | Kabat | 6 | ---WISAYNGNTNYAQKLQG | 50-66 | 17 |
| | Contact | 146 | WMGWISAYNGNTN------- | 47-59 | 13 |
| | IMGT | 147 | ----ISAYNGNT-------- | 51-58 | 8 |
| CDR-H3 | Chothia | 17 | --DLAVGTHGDY | 99-108 | 10 |
| | AbM | 17 | --DLAVGTHGDY | 99-108 | 10 |
| | Kabat | 17 | --DLAVGTHGDY | 99-108 | 10 |
| | Contact | 148 | ARDLAVGTHGD- | 97-107 | 11 |
| | IMGT | 149 | ARDLAVGTHGDY | 97-108 | 12 |

TABLE 5.1 -continued

B-09 VH and VL CDRs according to different definitions as sorted by inserting aa VH (SEQ ID No. 66) and VL (SEQ ID No. 81) sequence in the www.abysis.org annotation tool.

| | | | $V_L$ | | |
|---|---|---|---|---|---|
| Region | Definition | SEQ ID NO: | Sequence Fragment | Residues | Length |
| CDR-L1 | Chothia | 27 | TGTSSDVGGYNYVS-- | 23-36 | 14 |
| | AbM | 27 | TGTSSDVGGYNYVS-- | 23-36 | 14 |
| | Kabat | 27 | TGTSSDVGGYNYVS-- | 23-36 | 14 |
| | Contact | 150 | ------VGGYNYVSWY | 29-38 | 10 |
| | IMGT | 151 | ---SSDVGGYNY---- | 26-34 | 9 |
| CDR-L2 | Chothia | 37 | ----EVSNRPS | 52-58 | 7 |
| | AbM | 37 | ----EVSNRPS | 52-58 | 7 |
| | Kabat | 37 | ----EVSNRPS | 52-58 | 7 |
| | Contact | 152 | LMIYEVSNRP- | 48-57 | 10 |
| | IMGT | | ----EV----- | 52-53 | 2 |
| CDR-L3 | Chothia | 51 | SSYTSSSTLEVV | 91-102 | 12 |
| | AbM | 51 | SSYTSSSTLEVV | 91-102 | 12 |
| | Kabat | 51 | SSYTSSSTLEVV | 91-102 | 12 |
| | Contact | 153 | SSYTSSSTLEV- | 91-101 | 11 |
| | IMGT | 51 | SSYTSSSTLEVV | 91-102 | 12 |

TABLE 6

VH nucleotide sequences of exemplified antibodies

| Antibody | DNA of VH |
|---|---|
| A09 | CAGGTGCAGCTGGTGGAGTCTGGAGCTGAGGTGAAGAAGCCTGGGGCCTCAGTG AAGGTCTCCTGCAAGGCTTCTGGTTACACCTTTACCAGCTATGGTATCAGCTGGG TGCGACAGGCCCCTGGACAAGGGCTTGAGTGGATGGGATGGATCAGCGCTTACA ATGGTAACACAAACTATGCACAGAAGCTCCAGGGCAGAGTCACCATGACCACAGA CACATCCACGAGCACAGCCTACATGGAGCTGAGAAGCCTGAGATCTGACGACAC GGCCGTGTATTACTGTGCGAGAGAGTGGGAGCTACTTGGGGGGCTTGACTACTG GGGCCAGGGAACCCTGGTCACCGTGTCCTCA (SEQ ID No. 91) |
| B06 | GAGGTGCAGCTGTTGGAGTCTGGGGGAGGCTTGGTACAGCCTGGGGGGTCCCT GAGACTCTCCTGTGCAGCCTCTGGATTCACCTTTAGCAGCTATGCCATGAGCTGG GTCCGCCAGGCTCCAGGGAAGGGGCTGGAGTGGGTCTCAGCTATTAGTGGTAGT GGTGGTAGCACATACTACGCAGACTCCGTGAAGGGCCGGTTCACCATCTCCAGA GACAATTCCAAGAACACGCTGTATCTGCAAATGAACAGCCTGAGAGCCGAGGACA CGGCCGTATATTACTGTGCGAGGGGGGGCTGGTACGCTTGACTACTGGGGCCAGG GAACCCTGGTCACCGTGTCCTCA (SEQ ID No. 92) |
| C02 | CAGGTTCAGCTGGTGCAGTCTGGGGCTGAGGTGAAGAAGCCTGGGGCCTCAGTG AAGGTCTCCTGCAAGGCTTCTGGTTACACCTTTACCAGCTATGGTATCAGCTGGG TGCGACAGGCCCCTGGACAAGGGCTTGAGTGGATGGGATGGATCAGCGCTTACA ATGGTAACACAAACTATGCACAGAAGCTCCAGGGCAGAGTCACCATGACCACAGA CACATCCACGAGCACAGCCTACATGGAGCTGAGGAGCCTGAGATCTGACGACAC GGCCGTGTATTACTGTGCGAGAGGTCGGGGAGTTATAGACTACTGGGGCCAGGG AACCCTGGTCACCGTGTCCTCA (SEQ ID No. 93) |
| D10 | CAGGTGCAGCTGGTGCAGTCTGGGGCTGAGGTGAAGAAGCCTGGGGCCTCAGT GAAGGTCTCCTGCAAGGCTTCTGGTTACACCTTTACCAGCTATGGTATCAGCTGG GTGCGACAGGCCCCTGGACAAGGGCTTGAGTGGATGGGATGGATCAGCGCTTAC AATGGTAACACAAACTATGCACAGAAGCTCCAGGGCAGAGTCACCATGACCACAG ACACATCCACGAGCACAGCCTACATGGAGCTGAGGAGCCTGAGATCTGACGACA CGGCCGTGTATTACTGTGCGAGAGATCGATATTTGGGGTGGTTCGACCCCTGGG GCCAGGGAACCCTGGTCACCGTGTCCTCA (SEQ ID No. 94) |
| F05 | CAGGTTCAGCTGGTGCAGTCTGGAGCTGAGGTGAAGAAGCCTGGGGCCTCAGTG AAGGTCTCCTGCAAGGCTTCTGGTTACACCTTTACCAGCTACGGTATCAGCTGGG TGCGACAGGCCCCTGGACAAGGGCTTGAGTGGATGGGATGGATCAGCGCTTACA ATGGTAACACAAACTATGCACAGAAGCTCCAGGGCAGAGTCACCATGACCACAGA CACATCCACGAGCACAGCCTACATGGAGCTGAGGAGCCTGAGATCTGACGACAC GGCCGTGTATTACTGTGCGAGAGGTAGAGGTAGTTTCGACCCCTGGGGCCAGGG AACCCTGGTCACCGTGTCCTCA (SEQ ID No. 95) |
| B09 | CAGGTGTAGCTGGTGCAATCTGGAGCTGAGGTGAAGAAGCCTGGGGCCTCAGTG AAGGTCTCCTGCAAGGCTTCTGGTTACACCTTTACCAGCTATGGTATCAGCTGGG TGCGACAGGCCCCTGGACAAGGGCTTGAGTGGATGGGATGGATCAGCGCTTACA ATGGTAACACAAACTATGCACAGAAGCTCCAGGGCAGAGTTACCATGACCACAGA CACATCCACGAGCACAGCCTACATGGAGCTGAGGAGCCTGAGATCTGACGACAC |

TABLE 6-continued

VH nucleotide sequences of exemplified antibodies

| Antibody | DNA of VH |
|---|---|
| | GGCCGTGTATTACTGTGCGAGAGATCTGGCAGTTGGGACCCACGGTGACTACTG<br>GGGCCAGGGAACCCTGGTCACCGTGTCCTCA (SEQ ID No. 96) |
| B11 | CAGGTCCAGCTGGTGCAGTCTGGGGCTGAGGTGAAGAAGCCTGGGTCCTCGGTG<br>AAGGTCTCCTGCAAGGCTTCTGGAGGCACCTTCAGCAGCTATGCTATCAGCTGGG<br>TGCGACAGGCCCCTGGACAAGGGCTTGAGTGGATGGGAGGGATCATCCCTATCT<br>TTGGTACAGCAAACTACGCACAGAAGTTCCAGGGCAGAGTCACGATTACCGCGGA<br>CAAATCCACGAGCACAGCCTACATGGAGCTGAGCAGCCTGAGATCTGAGGACAC<br>GGCCGTGTATTACTGTGCGAGAAACGTCCGTCTCCCAGGCTGGTTCGACCCCTG<br>GGGCCAGGGAACCCTGGTCACCGTGTCCTCA (SEQ ID No. 97) |
| C11 | GAGGTGCAGCTGGTGGAGTCTGGGGGAGGCGTGGTCCAGCCTGGGAGGTCCCT<br>GAGACTCTCCTGTGCAGCCTCTGGATTCACCTTCAGTAGCTATGGCATGCACTGG<br>GTCCGCCAGGCTCCAGGCAAGGGGCTGGAGTGGGTGGCAGTTATATCATATGAT<br>GGAAGTAATAAATACTATGCAGACTCCGTGAAGGGCCGATTCACCATCTCCAGAG<br>ACAATTCCAAGAACACGCTGTATCTGCAAATGAACAGCCTGAGAGCTGAGGACAC<br>AGCTGTATACTACTGTGCGAGAGGGGACTATTCTGATACCAGTGGTACCGATTTCT<br>TCCAGCACTGGGGCCAGGGCACCCAGGTCACCGTGTCCTCA (SEQ ID No. 98) |
| C12 | CAGGTGCAGCTGGTGCAGTCTGGGGCTGAGGTGAAGAAGCCTGGGTCCTCGGTG<br>AAGGTCTCCTGCAAGGCTTCTGGAGGCACCTTCAGCAGCTATGCTATCAGCTGGG<br>TGCGACAGGCCCCTGGACAAGGGCTTGAGTGGATGGGAGGGATCATCCCTATCT<br>TTGGTACAGCAAACTACGCACAGAAGTTCCAGGGCAGAGTCACGATTACCGCGGA<br>CGAATCCACGAGCACAGCCTACATGGAGCTGAGCAGCCTGAGATCTGAGGACAC<br>GGCCGTGTATTACTGTGCGACCCTCGGGAGGGAGCTCAGCTTTGACTACTGGGG<br>CCAGGGAACCCTGGTCACCGTGTCCTCA (SEQ ID No. 99) |
| D12 | CAGGTCCAGCTGGTGCAGTCTGGGGCTGAGGTGAAGAAGCCTGGGTCCTCGGTG<br>AAGGTCTCCTGCAAGGCTTCTGGAGGCACCTTCAGCAGCTATGCTATCAGCTGGG<br>TGCGACAGGCCCCTGGACAAGGGCTTGAGTGGATGGGAGGGATCATCCCTATCT<br>TTGGTACAGCAAACTACGCACAGAAGTTCCAGGGCAGAGTCACGATTACCGCGGA<br>CGAATCCACGAGCACAGCCTACATGGAGCTGAGCAGCCTGAGATCTGAGGACAC<br>GGCCGTGTATTACTGTGCGAGATTCGGAAGGCCGCAGCTGGGCTATGCTTTTGAT<br>ATCTGGGGCCAAGGGACAATGGTCACCGTGTCTTCA (SEQ ID No. 100) |
| E02 | CAAATGCAGCTGGTGCAATCTGGGGCTGAGGTGAAGAAGCCTGGGTCCTCGGTG<br>AAGGTCTCCTGCAAGGCTTCTGGAGGCACCTTCAGCAGCTATGCTATCAGCTGGG<br>TGCGACAGGCCCCTGGACAAGGGCTTGAGTGGATGGGAGGGATCATCCCTATCT<br>TTGGTACAGCAAACTACGCACAGAAGTTCCAGGGCAGAGTCACGATTACCGCGGA<br>CGAATCCACGAGCACAGCCTACATGGAGCTGAGCAGCCTGAGATCTGAGGACAC<br>GGCCGTGTATTACTGTGCAACAATGTCAGTGGCTGGTCCTTCAATATCTTTTGACT<br>ACTGGGGCCAGGGAACCCTGGTCACCGTGTCCTCA (SEQ ID No. 101) |
| E03 | CAGGTGCAGCTGGTGCAGTCTGGGGCTGAGGTGAAGAAGCCTGGGTCCTCGGTG<br>AAGGTCTCCTGCAAGGCTTCTGGAGGCACCTTCAGCAGCTATGCTATCAGCTGGG<br>TGCGACAGGCCCCTGGACAAGGGCTTGAGTGGATGGGAGGGATCACCCCTATCT<br>TTGGTACAGCAAACTACGCACAGAAGTTCCAGGGCAGAGTCACGATTACCGCGGA<br>CGAATCCACGAGCACAGCCTACATGGAGCTGAGCAGCCTGAGATCTGAGGACAC<br>GGCCGTGTATTACTGTGCGAGAGCGGGAATTTTGACTGGTTATTACTTTGACTACT<br>GGGGCCAGGGAACCCTGGTCACCGTGTCCTCA (SEQ ID No. 102) |
| E05 | GAGGTGCAGCTGGTGGAGTCTGGGGGAGGCTTGGTACAGCCTGGGGGGTCCCT<br>GAAACTCTCCTGTGCAGCCTCTGGATTCACCTTCAGTGGCTATGGCATGAACTGG<br>GTCCGCCAGGCTCCAGGGAAGGGGCTGGAGTGGGTTTCATACGTTGGTAGTAGT<br>AGTAGTACCATATACTACGCAGATTCTGTGAAGGGCCGATTCACCATCTCCAGAG<br>ACAATGCCAACAACTCACTGTATCTGCAAATGAACAGCCTGAGAGCCGAGGACAC<br>GGCTGTGTATTACTGTGCGAGAGGCCTCGGTGGTAATTGGGGCCAAGGGACAAT<br>GGTCACCGTGTCTTCA (SEQ ID No. 103) |
| F04 | GAGGTGCAGCTGGTGGAGTCTGGGGGAGGCGTGGTCCAGCCTGGGAGGTCCCT<br>GAGACTCTCCTGTGCAGCCTCTGGATTCACCTTCAGTAGCTATGGCATGCACTGG<br>GTCCGCCAGGCTCCAGGCAAGGGGCTGGAGTGGGTGGCAGTTATATCATATGAT<br>GGAAGTAATAAATACTATGCAGACTCCGTGAAGGGCCGATTCACCATCTCCAGAG<br>ACAATTCCAAGAACACGCTGTATCTGCAAATGAACAGCCTGAGAGCTGAGGACAC<br>GGCTGTGTATTACTGTGCGAAACTTTCCGGGCCCAACGGTGTGGACTACTGGGG<br>CCAGGGAACCCTGGTCACCGTGTCCTCA (SEQ ID No. 104) |
| G01 | CAGGTTCAGCTGGTGCAGTCTGGGGCTGAGGTGAAGAAGCCTGGGTCCTCGGTG<br>AAGGTCTCCTGCAAGGCTTCTGGAGGCACCTTCAGCAGCTATGCTATCAGCTGGG<br>TGCGACAGGCCCCTGGACAAGGGCTTGAGTGGATGGGAGGGATCATCCCTATCT<br>TTGGTACAGCAAACTACGCACAGAAGTTCCAGGGCAGAGTCACGATTACCGCGGA<br>CGAATCCACGAGCACAGCCTACATGGAGCTGAGCAGCCTGAGATCTGAGGACAC<br>GGCCGTGTATTACTGTGCGAGCATTACGGAGGGGGCCTTTGACTACTGGGGCCA<br>GGGAACCCTGGTCACCGTGTCCTCA (SEQ ID No. 105) |

TABLE 7

| VL nucleotide sequences | |
|---|---|
| Antibody | DNA of VL |
| A09 | CAGTCTGCCCTGACTCAGCCTGCCTCCGTGTCTGGGTCTCCTGGACAGTCGATCA CCATCTCCTGCACTGGAACCAGCAGTGACGTTGGTGGTTATAACTATGTCTCCTG GTACCAACAGCACCCAGGCAAAGCCCCCAAACTCATGATTTATGAGGTCAGTAAT CGGCCCTCAGGGGTTTCTAATCGCTTCTCTGGCTCCAAGTCTGGCAACACGGCCT CCCTGACCATCTCTGGGCTCCAGGCTGAGGACGAGGCTGATTATTACTGCAGCTC ATATACAAGCAGCAGCACTGTGGTATTCGGCGGAGGGACCAAGCTGACCGTCCTA (SEQ ID No. 106) |
| B06 | GACATCGTGATGACCCAGTCTCCAGACTCCCTGGCTGTGTCTCTGGGCGAGAGG GCCACCATCAACTGCAAGTCCAGCCAGAGTGTTTTATACAGCTCCAACAATAAGAA CTACTTATCTTGGTACCAGCAGAAACCAGGTCAGCCTCCTAAGCTGCTCATTTACT GGGCATCTACCCGGGAATCCGGGGTCCCTGACCGATTCAGTGGCAGCGGGTCTG GGACAGATTTCACTCTCACCATCAGCAGCCTGCAGGCTGAAGATGTGGCAGTTTA TTACTGTCAGCAATATTATAGTACTCCGCTCACTTTCGGCGGAGGGACCAAGGTG GAAATCAAA (SEQ ID No. 107) |
| C02 | GAAATAGTGATGACGCAGTCTCCAGACTCCCTGGCTGTGTCTCTGGGCGAGAGG GCCACCATCAACTGCAAGTCCAGCCAGAGTGTTTTATACAGCTCCAACAATAAGAA CTACTTAGCTTGGTACCAGCAGAAACCAGGACAGCCTCCTAAGCTGCTCATTTACT GGGCATCTACCCGGGAATCCGGGGTCCCTGACCGATTCAGTGGCAGCGGGTCTG GGACAGATTTCACTCTCACCATCAGCAGCCTGCAGGCTGAAGATGTGGCAGTTTA TTACTGTCAGCAATATTATAGTACTCCGCTCACTTTCGGCGGAGGGACCAAAGTG GATATCAAA (SEQ ID No. 108) |
| D10 | CAGTCTGCCCTGACTCAGCCTGCCTCCGTGTCTGGGTCTCCTGGACAGTCGATCA CCATCTCCTGCACTGGAACCAGCAGTGACGTTGGTGGTTATAACTATGTCTCCTG GTACCAACAGCACCCAGGCAAAGCCCCCAAACTCATGATTTATGAGGTCAGTAAT CGGCCCTCAGGGGTTTCTAATCGCTTCTCTGGCTCCAAGTCTGGCAACACGGCCT CCCTGACCATCTCTGGGCTCCAGGCTGAGGATGAGGCTGATTATTACTGCAGCTC ATATACAAGCAGCAGCACCCCTTATGTCTTCGGAACTGGGACCAAGCTGACCGTC CTA (SEQ ID No. 109) |
| F05 | GACATCCAGTTGACCCAGTCTCCAGACTCCCTGGCTGTGTCTCTGGGCGAGAGG GCCACCATCAACTGCAAGTCCAGCCAGAGTGTTTTATACAGCTCCAACAATAAGAA CTACTTAGCTTGGTACCAGCAGAAACCAGGACAGCCTCCTAAGCTGCTCATTTACT GGGCATCTACCCGGGAATCCGGGGTCCCTGACCGATTCAGTGGCAGCGGGTCTG GGACAGATTTCACTCTCACCATCAGCAGCCTGCAGGCCGAAGATGTGGCAGTTTA TTACTGTCAGCAATATTATAGTACTCCTCTCACTTTCGGCGGAGGGACCAAGGTG GAGATCAAA (SEQ ID No. 110) |
| B09 | CAGTCTGCCCTGACTCAGCCTGCCTCCGTGTCTGGGTCTCCTGGACAGTCGATCA CCATCTCCTGCACTGGAACCAGCAGTGACGTTGGTGGTTATAACTATGTCTCCTG GTACCAACAGCACCCAGGCAAAGCCCCCAAACTCATGATTTATGAGGTCAGTAAT CGGCCCTCAGGGGTTTCTAATCGCTTCTCTGGCTCCAAGTCTGGCAACACGGCCT CCCTGACCATCTCTGGGCTCCAGGCTGAGGACGAGGCTGATTATTACTGCAGCTC ATACACAAGCAGCAGCACTCTCGAGGTGGTATTCGGCGGAGGGACCAAGCTGAC CGTCCTA (SEQ ID No. 111) |
| B11 | GACATCCAGATGACCCAGTCTCCTTCCACCCTGTCTGCATCTGTAGGAGACAGAG TCACCATCACTTGCCGGGCCAGTCAGAGTATTAGTAGCTGGTTGGCCTGGTATCA GCAGAAACCAGGGAAAGCCCCTAAGCTCCTGATCTATAAGGCGTCTAGTTTAGAA AGTGGGGTCCCATCAAGGTTCAGCGGCAGTGGATCTGGGACAGAATTCACTCTCA CCATCAGCAGCCTGCAGCCTGATGATTTTGCAACTTATTACTGCCAACAGTATAAT AGTTACCCGCTCACTTTCGGCGGAGGGACCAAGGTGGAGATCAAA (SEQ ID No. 112) |
| C11 | GACATCGTGATGACCCAGTCTCCATCCTCCCTGTCTGCATCTGTAGGAGACAGAG TCACCATCACTTGCCGGGCAAGTCAGAGCATTAGCAGCTATTTAAATTGGTATCAG CAGAAACCAGGGAAAGCCCCTAAGCTCCTGATCTATGCTGCATCCAGTTTGCAAA GTGGGGTCCCATCAAGGTTCAGTGGCAGTGGATCTGGGACAGATTTCACTCTCAC CATCAGCAGTCTGCAACCTGAAGATTTTGCAACTTACTACTGTCAACAGAGTTACA GTACCCCAGGGTTCGGCGGAGGGACCAAGGTGGAGATCAAA (SEQ ID No. 113) |
| C12 | GATATTGTGATGACTCAGTCTCCATCCTCCCTGTCTGCATCTGTAGGAGACAGAGT CACCATCACTTGCCGGGCAAGTCAGAGCATTAGCAGCTATTTAAATTGGTATCAGC AGAAACCAGGGAAAGCCCCTAAGCTCCTGATCTATGCTGCATCCAGTTTGCAAAG TGGGGTCCCATCAAGGTTCAGTGGCAGTGGATCTGGGACAGATTTCACTCTCACC ATCAGCAGTCTGCAACCTGAAGATTTTGCAACTTACTACTGTCAACAGAGTTACAG TGAGTCGTGGACGTTCGGCCAGGGGACCACGGTGGACATCAAA (SEQ ID No. 114) |
| D12 | GAAACGACACTCACGCAGTCTCCAGGCACCCTGTCTGTGTCTCCAGGGGATAGA GCCACCCTCTCCTGCAGGGCCAGTCAGAGTCTTAGCGCCGACTACTTAGCCTGGT ACCAGCAGAAACCTGGCCAGGCTCCCAGGCTCCTCATCTATGGTGCATCCACAAG GGCCACTGGTATCCCAGCCAGGTTCAGTGGCAGTGGGTCTGGGACAGAGTTCAC TCTCACCGTCAGCAGCCTGCAGTCTGAAGATTTTGCAGTTTATTACTGTCAGCAGA |

TABLE 7-continued

| VL nucleotide sequences | |
|---|---|
| Antibody | DNA of VL |
| | ATGATAACTGGCCGTACACTTTTGGCCAGGGGACCAAGCTGGAGATCAAA (SEQ ID No. 115) |
| E02 | GACATCCAGATGACCCAGTCTCCATCTTCCCTGTCCGCATCTGTGGGAGACAGAG TCGCCATCCCTTGCCGGGCAAGTCAGAGCATTAGCAGCTACTTAAATTGGTATCA GCAGAAACCAGGGAAAGCCCCTAAACTGCTGATCTACGCTGCATCCAGTTTGCAA AGAGGGGTCCCATCAAGGTTCAGTGGCAGTGGATCTGGGACAGATTTCACTCTCA CCATCAGCAGTCTGCAACCTGAAGATTTTGCAACTTACTATTGTCAAGAGACTTAC AGTAACCTGTGGACGTTCGGCCAAGGGACCAAGGTGGAAATCAAA (SEQ ID No. 116) |
| E03 | AATTTTATGCTGACTCAGCCCCACTCTGTGTCGGAGTCTCCGGGGAAGACGGTAA CCATCTCCTGCACCCGCAGCAGTGGCAGCATTGCCAGCAACTATGTGCAGTGGTA CCAGCAGCGCCCGGGCAGTTCCCCCACCACTGTGATCTATGAGGATAACCAAAG ACCCTCTGGGGTCCCTGATCGGTTCTCTGGCTCCATCGACAGCTCCTCCAACTCT GCCTCCCTCACCATCTCTGGACTGAAGACTGAGGACGAGGCTGACTACTACTGTC AGTCTTATGATAGCAGCAATCGGCCTTGGGTGTTCGGCGGAGGGACCAAGCTGA CCGTCCTA (SEQ ID No. 117) |
| E05 | CAGCCTGGGCTGACTCAGCCACCCTCAGCGTCTGGGGCCCCCGGGCAGAGGGT CACCATCTCTTGTTCTGGAAGCAGGTCCAATATCGGTTCTAATTATGTACACTGGT ACCAACAACTCCCAGGAACGGCCCCCAAACTCATCATTTATAGGAATGATCAGCG GCCCTCAGGGGTCCCTGCCCGATTCTCTGCCTCCAAGTCTGGCACCTCAGCCTC CCTGGCCATCAGTGGGCTCCGGTCCGAGGATGAAGCTGATTACTACTGTGCAGC GTGGGATGACGGACTGAGTGTCCTATTCGGCGGAGGGACCAAGTTGACCGTCCT A (SEQ ID No. 118) |
| F04 | TCTTCTGAGCTGACTCAGGACCCCTCTGTGTCTGTGGCCTTGGGACAAACAGTCA CTATCACGTGCCAAGGAGACAGTGTCAGAAAGTATTATACGAACTGGTATCAACA GAAGCCAGGACAGGCCCCTATCCTTGTCCTCTATGGTAAAAACTACCGGCCCTCA GGGATCCCAGACCGATTCTCTGGCTCCACGTCCGGAGACACAGCGTACTTGACC ATCACTGGGGCTCAGGCGGAGGATGCGGCAGACTATTATTGTCACTCCCGGGAC ACCAGTGATATCCATCTAAATGTCTTCGGCACTGGGACCAAGGTCACCGTCCTA (SEQ ID No. 119) |
| G01 | GCCATCCAGTTGACCCAGTCTCCTTCCACCCTGTCTGCATCTGTAGGAGACAGAG TCACCATCACTTGCCGGGCCAGTCGGACTGTTGGTAGCTGGTTGGCCTGGTATCA GCAGAAACCAGGGAAAGCCCCTAAGCTCCTGATCTATGATGCCTCCAATTTGCAA AGTGGGGTCCCATCAAGGTTCAGCGGCAGTGGATCTGGGACAGAATTCACTCTCA CCATCAGCAGCCTGCAGCCTGATGATTTTGTCAACTTATTACTGCCAACAGTATAAT AGTTCCCCGTACACTTTTGGCCAGGGGACCAAGGTGGAGATCAAA (SEQ ID No. 120) |

TABLE 8

| Constant region amino acid sequences | |
|---|---|
| Constant region | AA |
| Human IgG4 heavy chain P01861.1 | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRVE SKYGPPCPSCPAPEFLGGPSVFLFPPKPKDTLMISRTPEVTCVVVDVSQE DPEVQFNWYVDGVEVHNAKTKPREEQFNSTYRVVSVLTVLHQDWLNGK EYKCKVSNKGLPSSIEKTISKAKGQPREPQVYTLPPSQEEMTKNQVSLTC LVKGFYPSDIAVEWESNGQPENNYKTTPPVLDSDGSFFLYSRLTVDKSR WQEGNVFSCSVMHEALHNHYTQKSLSLSLGK (SEQ ID No. 121) |
| Human IgG2 heavy chain P01859 | ASTKGPSVFPLAPCSRSTSESTAALGCLVKDYFPEPVTVSWNSGALTSG VHTFPAVLQSSGLYSLSSVVTVPSSNFGTQTYTCNVDHKPSNTKVDKTVE RKCCVECPPCPAPPVAGPSVFLFPPKPKDTLMISRTPEVTCVVVDVSHED PEVQFNWYVDGVEVHNAKTKPREEQFNSTFRVVSVLTVVHQDWLNGKE YKCKVSNKGLPAPIEKTISKTKGQPREPQVYTLPPSREEMTKNQVSLTCL VKGFYPSDISVEWESNGQPENNYKTTPPMLDSDGSFFLYSKLTVDKSRW QQGNVFSCSVMHEALHNHYTQKSLSLSPGK (SEQ ID No. 122) |
| Human light chain, lambda 1 P0CG04 | GQPKANPTVTLFPPSSEELQANKATLVCLISDFYPGAVTVAWKADGSPVK AGVETTKPSKQSNNKYAASSYLSLTPEQWKSHRSYSCQVTHEGSTVEKT VAPTECS (SEQ ID No. 123) |
| Human light chain, lambda 2 P0DOY2 | GQPKAAPSVTLFPPSSEELQANKATLVCLISDFYPGAVTVAWKADSSPVK AGVETTTPSKQSNNKYAASSYLSLTPEQWKSHRSYSCQVTHEGSTVEKT VAPTECS (SEQ ID No. 124) |

TABLE 8-continued

| Constant region amino acid sequences | |
|---|---|
| Constant region | AA |
| Human light chain, kappa P01834 | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC (SEQ ID No. 125) |

Method of Expressing Recombinant Protein in CHO Cells

The corresponding B06 and B09 cDNAs were cloned into evitria's vector system using conventional (non-PCR based) cloning techniques. The evitria vector plasmids were gene synthesized. Plasmid DNA was prepared under low-endotoxin conditions based on anion exchange chromatography. Correctness of the sequences was verified with Sanger sequencing (with up to two sequencing reactions per plasmid depending on the size of the cDNA.)

Suspension-adapted CHO K1 cells (evitria) was used for production. The seed was grown in eviGrow medium, a chemically defined, animal-component free, serum-free medium. Cells were transfected with eviFect, evitria's custom-made, proprietary transfection reagent, and cells were grown after transfection in eviMake, an animal-component free, serum-free medium, at 37° C. and 5% $CO_2$ for 7 days. Supernatant was harvested by centrifugation and subsequent filtration (0.2 μm filter).

The antibody was purified using MabSelect™ SuRe™ with Dulbecco's PBS (Lonza BE17-512Q) as wash buffer and 0.1 M Glycine pH 3.5 as elution buffer. Subsequent size exclusion chromatography was performed on a HiLoad Superdex 200 μg column using the final buffer as running buffer.

Monomericity was determined by analytical size exclusion chromatography with an Agilent AdvanceBio SEC column (300A 2.7 μm 7.8×300 mm) and DPBS as running buffer at 0.8 ml/min.

Example 2: Affinity Measurement

Octet BLI-Based Analysis

To assess the binding affinity in more detail, affinity measurements were performed using Biomolecular Interaction Analysis performed by an Octet platform (BLItz System), which is a Biolayer Interferometry (BLI) platform. To establish the assay, the target monoclonal antibody (mAb, 2 identical antigen binding moieties, 2 μg/ml in 1% BSA containing 0.05% Tween 20) was immobilized via Fc on the via AHC biosensor and the interaction with the antigen human IGFBP5 (R&D, cat n° 875-B5) and mouse IGFBP5 (R&D, cat n° 578-B5) at different concentration were measured.

The affinity measurement of B06 and B09 full length mAb for the target human and murine IGFBP5 are reported in the Table 9.

TABLE 9

| Affinity of B06 and B09 for the target human and murine IGFBP5 | | |
|---|---|---|
| Molecule id | B06 | B09 |
| hIGFBP-5 KD (M) | $1 \times 10^{-10}$ | $1 \times 10^{-10}$ |
| mIGFBP-5 KD (M) | $1 \times 10^{-10}$ | $1 \times 10^{-10}$ |

Newly generated anti-IGFBP5 mAbs show good human antigen binding affinity with KD below $4 \times 10^{-10}$ M. The antibodies also show murine cross reactivity. This data confirmed that mice can be considered a relevant animal species for testing of the monoclonal antibodies during preclinical development.

Example 3: Primary Cell-Based Assay Relevant to Fibrosis (IPF)

Fibrosis is a process of continuous tissue repair characterized by the formation and deposition of fibrillary collagen-rich extracellular matrix (ECM) leading to a progressive remodeling in most tissues and organs. Formation of fibrotic scar tissue is essential to restore and maintain tissue and organ integrity during wound healing after injury. However, when the scarring mechanisms exacerbate after repetitive injury, chronic fibrogenesis results in a shift from supportive fibrotic tissue to scar tissue. This coincides with an increased number and activity of extracellular matrix producing cells, which finally leads to destruction of normal tissue/organ architecture and function.

In the lung, such as in Idiopathic Pulmonary Fibrosis disease (IPF), tissue scarring/fibrosis occurs. Tissue damage is followed by the activation of the immune system that induces release of several cytokines and growth factors including transforming growth factor beta-1 (TGFβ-1) that signals the tissue to repair. Mechanistically, epithelial to mesenchymal transition (EMT) is one of the major drivers of fibrosis, and approximately 30% of ECM-producing (myo-) fibroblasts derive from epithelial cells through EMT. During EMT, tightly organized epithelial cells lose expression of the tight junction marker E-cadherin and transform to mesenchymal cells with expression of the mesenchymal cell markers N-cadherin, vimentin and fibronectin. Furthermore, the cells gain migratory potential, enabling them to migrate throughout the tissue. Another important mechanism during fibrosis is fibroblast to myofibroblast transformation (FMT), when EMT-derived, resident and invading fibroblastoid cells are activated (e.g., by TGFβ-1) and start to differentiate towards myofibroblasts. Myofibroblasts are a heterogeneous population derived from different progenitors, and are characterized by formation of alpha smooth muscle actin (αSMA) containing stress fibers and the expression and secretion of fibrillar collagen, fibronectin and additional ECM components. Increased production and accumulation of ECM result in a permanently damaged fibrotic tissue with an aberrant architecture unable to function properly.

FMT and EMT in vitro assays are established models to identify and characterize anti-fibrotic compounds (see Weigle et al. J Biol Methods (2019) Vol. 6 (2)).

Fibroblast-to-Myofibroblast Transition (FMT) Assay

Human bronchial lung fibroblasts derived from three IPF patients were seeded in 384-well plates (Cat. 6057302, Perkin Elmer) at a density of 750 cells/well in 2% FBS-DMEM (DMEM supplemented with 2% fetal bovine serum (Cat. 10100-147, Gibco) and 1% penicillin and streptomycin (Cat. 15140, Gibco)). Two days after seeding, cells were refreshed with 2% FBS-DMEM. Five days after seeding, cells were refreshed with 0.2% FBS-DMEM (DMEM supplemented with 0.2% fetal bovine serum (Cat. 10100-147, Gibco) and 1% penicillin and streptomycin (Cat. 15140, Gibco)) and the anti-IGFBP5 mAbs (B06 and B09) were added in an eight-step concentration response curve using 0.5LogM dilution steps with a top concentration of 1.1 μM for B06 and 1.5 UM for B09. ALK5 inhibitor (SB525334; Cat. S8822-25, Sigma at 1 μM in 0.1% DMSO (positive control), 0.1% DMSO (vehicle control 1; Cat. D8418, Sigma) and 3.6% PBS (vehicle control 2) were used to assess assay performance. One hour after the anti-IGFBP5 mAbs (B06 and B09), DMSO or PBS addition, cells were triggered with 1.25 ng/ml TGF-β1 (Cat. 240-B-010, R&D Systems) to induce Fibroblast-to-Myofibroblast Transition (FMT). Three (3) days after TGF-31 addition, the cells were fixed with 4% formaldehyde (Cat. 8187081000, Merck) and stained for α-smooth muscle actin (αSMA) as a marker of myofibroblast and nuclei (DAPI). For determination of αSMA expression, fixed lung fibroblasts were incubated in blocking buffer (PBS containing 5 mg/mL BSA (Cat. A2153, Sigma) and 0.2% (vol/vol) Triton X-100 (Cat. T8787, Sigma)) for one hour at room temperature. Cells were then incubated with a monoclonal Alexa Fluor 488-conjugated anti-αSMA antibody (1 μg/mL; Cat. AB184675, Abcam) for one hour at room temperature, washed with PBS and incubated with 4',6-diamidino-2-fenylindole (DAPI, 0.5 μg/mL; Cat. D3571, Life Technologies) and imaged on the In Cell Analyzer 2200 (GE Healthcare). Expression was quantified using the IN Cell developer software (GE Healthcare). αSMA expression is presented as the staining intensity multiplied by the stained area (D×A levels). Co-staining of cell nuclei with DAPI was performed to quantify cell number, as a measure of potential cytotoxicity.

After analysis, the anti-IGFBP5 mAbs showed a concentration-dependent inhibition of TGF-β1-mediated αSMA expression in IPF patient samples. Moreover, the anti-IGFBP5 mAbs showed no modulation of the number of nuclei, indicative of absence of potential cytotoxic side-effects (FIG. 1).

Epithelial-to-Mesenchymal Transition (EMT) Assay

Human bronchial epithelial cells (HBECs) derived from three IPF patients (IPF05, IPF06, and IPF07) were seeded in 384-well plates (Cat. 6057302, Perkin Elmer) at a density of 900 cells/well in KSFM Complete (keratinocyte serum-free medium supplemented with 0.2 ng/mL epidermal growth factor, 25 μg/mL bovine pituitary extract (all from Cat. 17005-075, Gibco), 1 μmol/L isoproterenol (Cat. 16504, Sigma) and 1% penicillin and streptomycin (Cat. 15140, Gibco)). Two days after seeding, cells were refreshed with KSFM Complete. Six days after seeding, cells were refreshed with KSFM Complete and the anti-IGFBP5 mAbs (B06 and B09) were added in an eight-step concentration response curve using 0.5LogM dilution steps with a top concentration of 1.1 μM for B06 and 1.5 UM for B09. ALK5 inhibitor (SB525334; Cat. S8822-25, Sigma) at 1 μM in 0.1% DMSO (positive control), 0.1% DMSO (vehicle control 1; Cat. D8418, Sigma) and 3.6% Limited) was PBS (vehicle control 2) were used to assess assay performance. One hour after the anti-IGFBP5 mAbs (B06 and B09), DMSO or PBS addition, cells were triggered with 5 ng/ml TGF-β1 (Cat. 240-B-010, R&D Systems) to induce Epithelial-to-Mesenchymal Transition (EMT). Three days after trigger addition, cells were fixed with 4% formaldehyde (Cat. 8187081000, Merck) and stained for fibronectin (FN1), a mesenchymal cell marker and nuclei (DAPI). For determination of FN1 expression, fixed HBECs were incubated in blocking buffer (PBS containing 5 mg/mL BSA (Cat. A2153, Sigma) and 0.2% (vol/vol) Triton X-100 (Cat. T8787, Sigma)) for one hour at room temperature. Cells were then incubated with a monoclonal anti-FN1 antibody (0.125 μg/mL; Cat. 610001, Biohit healthcare) for one hour at room temperature, washed with 0.05% Tween-20 (Cat. P1379, Sigma) in PBS and incubated with an Alexa Fluor 546-conjugated donkey anti-mouse secondary antibody (4 μg/mL; Cat. A10036, Life Technologies) for one hour at room temperature. Plates were then washed with 0.05% Tween in PBS, incubated with 4',6-diamidino-2-fenylindole (DAPI, 0.5 μg/mL; Cat. D3571, Life Technologies) and imaged on the In Cell Analyzer 2200 (GE Healthcare). Expression was quantified using the IN-Cell developer software (GE Healthcare). FN1 expression is presented as the staining intensity multiplied by the stained area (DxA levels). Co-staining of cell nuclei with DAPI was performed to quantify cell number, as a measure of potential cytotoxicity.

Figure 2:
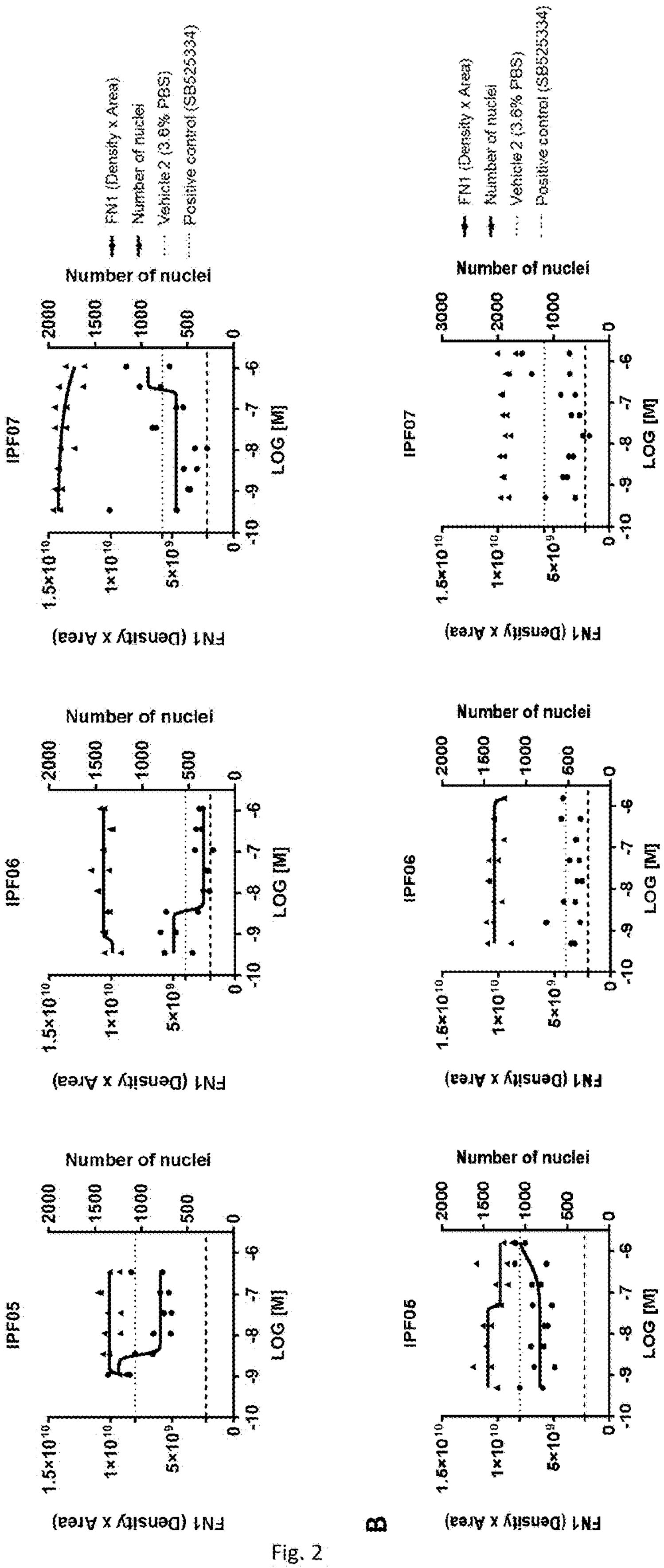
FIG. 2. Effect of anti-IGFBP5 mAbs on Epithelial-to-Mesenchymal Transition (EMT) assay upon TGF-β1 exposure. Human primary bronchial epithelial cells (HBECs) from three IPF donors (IPF05, IPF06 and IPF07) were triggered with 5 ng/ml of TGF-β1 to induce EMT. The anti-IGFBP5 mAbs, B06 (A) and B09 (B) were tested in an EMT assay to check its capacity to inhibits the FN1 expression. Anti-IGFBP5 mAb B06 showed a concentration-dependent inhibition of TGF-β1-mediated FN1 expression in tissue of IPF patient donors. Vehicle 2: cells treated with 3.6% PBS and 5 ng/ml of TGF-β1.

After analysis, the anti-IGFBP5 mAb B06 showed a concentration-dependent inhibition of TGF-β1-mediated FN1 expression in IPF patient samples of donors IPF05 and IPF06. Moreover, all the anti-IGFBP5 mAbs showed no modulation of the number of nuclei, indicative of absence of potential cytotoxic side-effects (FIG. 2).

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

While various specific embodiments have been illustrated and described, the above specification is not restrictive. It will be appreciated that various changes can be made without departing from the spirit and scope of the invention (s). Many variations will become apparent to those skilled in the art upon review of this specification.

The invention claimed is:

1. An inhibitor of IGFBP5 and/or of at least one of its receptors, wherein said inhibitor binds to IGFBP5 and has anti-fibrotic effect and/or an anti-fibrosis activity, and wherein the inhibitor is an antibody or antigen binding fragment thereof, having three heavy chain (VH) CDRs and three light chain (VL) CDRS according to the following:

(a) A09: SEQ ID NO:1 (VH CDR1), SEQ ID NO:6 (VH CDR2), SEQ ID NO: 12 (VH CDR3), SEQ ID NO:27 (VL CDR1), SEQ ID NO:37 (VL CDR2), and SEQ ID NO: 48 (VL CDR3);

(b) B06: SEQ ID NO:2 (VH CDR1), SEQ ID NO:7 (VH CDR2), SEQ ID NO: 13 (VH CDR3), SEQ ID NO:28 (VL CDR1), SEQ ID NO:38 (VL CDR2), and SEQ ID NO: 49 (VL CDR3);

(c) C02: SEQ ID NO:1 (VH CDR1), SEQ ID NO:6 (VH CDR2), SEQ ID NO: 14 (VH CDR3), SEQ ID NO:29 (VL CDR1), SEQ ID NO:38 (VL CDR2), and SEQ ID NO: 49 (VL CDR3);

(d) D10: SEQ ID: 1 (VH CDR1), SEQ ID NO:6 (VH CDR2), SEQ ID NO: 15 (VH CDR3), SEQ ID NO:27 (VL CDR1), SEQ ID NO:39 (VL CDR2), and SEQ ID NO: 50 (VL CDR3);

(e) F05: SEQ ID: 1 (VH CDR1), SEQ ID NO:6 (VH CDR2), SEQ ID NO: 16 (VH CDR3), SEQ ID NO:29 (VL CDR1), SEQ ID NO:38 (VL CDR2), and SEQ ID NO: 49 (VL CDR3);

(f) B09: SEQ ID: 1 (VH CDR1), SEQ ID NO:6 (VH CDR2), SEQ ID NO: 17 (VH CDR3), SEQ ID NO:27 (VL CDR1), SEQ ID NO:39 (VL CDR2), and SEQ ID NO: 51 (VL CDR3);

(g) B11: SEQ ID NO:3 (VH CDR1), SEQ ID NO:8 (VH CDR2), SEQ ID NO: 18 (VH CDR3), SEQ ID NO:30 (VL CDR1), SEQ ID NO:40 (VL CDR2), and SEQ ID NO: 52 (VL CDR3);

(h) C11: SEQ ID NO:4 (VH CDR1), SEQ ID NO:9 (VH CDR2), SEQ ID NO: 19 (VH CDR3), SEQ ID NO:31 (VL CDR1), SEQ ID NO:41 (VL CDR2), and SEQ ID NO: 53 (VL CDR3);

(i) C12: SEQ ID NO:3 (VH CDR1), SEQ ID NO:8 (VH CDR2), SEQ ID NO:20 (VH CDR3), SEQ ID NO:31 (VL CDR1), SEQ ID NO:41 (VL CDR2), and SEQ ID NO: 54 (VL CDR3);

(i) D12: SEQ ID NO:3 (VH CDR1), SEQ ID NO:8 (VH CDR2), SEQ ID NO:21 (VH CDR3), SEQ ID NO:32 (VL CDR1), SEQ ID NO:42 (VL CDR2), and SEQ ID NO: 55 (VL CDR3);

(k) E02: SEQ ID NO:3 (VH CDR1), SEQ ID NO:8 (VH CDR2), SEQ ID NO:22 (VH CDR3), SEQ ID NO:31 (VL CDR1), SEQ ID NO:43 (VL CDR2), and SEQ ID NO: 56 (VL CDR3);

(l) E03: SEQ ID NO:3 (VH CDR1), SEQ ID NO: 10 (VH CDR2), SEQ ID NO:23 (VH CDR3), SEQ ID NO:33 (VL CDR1), SEQ ID NO:44 (VL CDR2), and SEQ ID NO: 57 (VL CDR3);

(m) E05: SEQ ID NO:5 (VH CDR1), SEQ ID NO: 11 (VH CDR2), SEQ ID NO:24 (VH CDR3), SEQ ID NO:34 (VL CDR1), SEQ ID NO:45 (VL CDR2), and SEQ ID NO: 58 (VL CDR3);

(n) F04: SEQ ID NO:4 (VH CDR1), SEQ ID NO:9 (VH CDR2), SEQ ID NO:25 (VH CDR3), SEQ ID NO:35 (VL CDR1), SEQ ID NO:46 (VL CDR2), and SEQ ID NO: 59 (VL CDR3); and (o) G01: SEQ ID NO:3 (VH CDR1), SEQ ID NO:8 (VH CDR2), SEQ ID NO:26 (VH CDR3), SEQ ID NO:36 (VL CDR1), SEQ ID NO:47 (VL CDR2), and SEQ ID NO: 60 (VL CDR3).

2. The inhibitor according to claim 1, comprising:

(a). a heavy chain variable domain (VH) comprising:

i. a CDR1 sequence of SEQ ID NO. 2;

ii. a CDR2 sequence of SEQ ID NO. 7; and iii. a CDR3 sequence of SEQ ID NO. 13; and (b). a light chain variable domain (VL) comprising:

i. a CDR1 sequence of SEQ ID NO. 28;

ii. a CDR2 sequence of SEQ ID NO. 38; and iii. a CDR3 sequence of SEQ ID NO. 49.

3. The inhibitor according to claim 1, comprising:

(a). a heavy chain variable domain (VH) comprising:

i. a CDR1 sequence of SEQ ID NO. 1;

ii. a CDR2 sequence of SEQ ID NO. 6; and iii. a CDR3 sequence of SEQ ID NO. 17; and (b). a light chain variable domain (VL) comprising:

i. a CDR1 sequence of SEQ ID NO. 27;

ii. a CDR2 sequence of SEQ ID NO. 39; and iii. a CDR3 sequence of SEQ ID NO. 51.

4. The inhibitor according to claim 1, comprising:

(a). a heavy chain variable domain sequence of the amino acid sequence selected from the group consisting of: SEQ ID NO:61, 62, 63, 64, 65, 66, 67, 68, 69, 70, 71, 72, 73, 74 and 75 and, (b). a light chain variable domain sequence of the amino acid sequence selected from the group consisting of: SEQ ID NO: 76, 77, 78, 79, 80, 81, 82, 83, 84, 85, 86, 87, 88, 89, and 90.

5. The inhibitor according to claim 1, having an affinity constant lower than or equal to $10^{-8}$ M for human IGFBP5.

6. The inhibitor according to claim 1, being a human or a humanized antibody.

7. The inhibitor according to claim 6, being an IgG2 or IgG4 antibody, an IgG2 kappa antibody, an IgG2 lambda antibody, an IgG4 kappa antibody or an IgG4 lambda antibody.

8. The inhibitor according to claim 1, wherein said inhibitor reduces or inhibits the binding of IGFBP5 to at least one of its receptors.

9. The inhibitor according to claim 1, wherein said inhibitor i) reduces or inhibits extracellular matrix production and/or ii) reduces or inhibits extracellular matrix deposition and/or iii) reduces or inhibits collagen and/or fibronectin production in primary lung fibroblasts and/or iv) reduces or inhibits collagen and/or fibronectin deposition in primary lung fibroblasts.

10. A pharmaceutical composition comprising an inhibitor of IGFBP5 and/or of at least one of its receptors, wherein said inhibitor has anti-fibrotic effect and/or an anti-fibrosis activity and a pharmaceutically acceptable carrier, for use in the treatment of fibrosis or of a fibrotic condition, wherein the inhibitor is an antibody or antigen binding fragment thereof having three heavy chain (VH) CDRs and three light chain (VL) CDRS, according to the following:

(a) A09: SEQ ID NO:1 (VH CDR1), SEQ ID NO:6 (VH CDR2), SEQ ID NO: 12 (VH CDR3), SEQ ID NO:27 (VL CDR1), SEQ ID NO:37 (VL CDR2), and SEQ ID NO: 48 (VL CDR3);

(b) B06: SEQ ID NO:2 (VH CDR1), SEQ ID NO:7 (VH CDR2), SEQ ID NO: 13 (VH (b) B06: CDR3), SEQ ID NO:28 (VL CDR1), SEQ ID NO:38 (VL CDR2), and SEQ ID NO: 49 (VL CDR3);

(c) C02: SEQ ID NO: 1 (VH CDR1), SEQ ID NO:6 (VH CDR2), SEQ ID NO: 14 (VH CDR3), SEQ ID NO:29 (VL CDR1), SEQ ID NO:38 (VL CDR2), and SEQ ID NO: 49 (VL CDR3);

(d) D10: SEQ ID: 1 (VH CDR1), SEQ ID NO:6 (VH CDR2), SEQ ID NO: 15 (VH CDR3), SEQ ID NO:27 (VL CDR1), SEQ ID NO:39 (VL CDR2), and SEQ ID NO: 50 (VL CDR3);

(e) F05: SEQ ID: 1 (VH CDR1), SEQ ID NO:6 (VH CDR2), SEQ ID NO: 16 (VH CDR3), SEQ ID NO:29 (VL CDR1), SEQ ID NO:38 (VL CDR2), and SEQ ID NO: 49 (VL CDR3);

(f) B09: SEQ ID: 1 (VH CDR1), SEQ ID NO:6 (VH CDR2), SEQ ID NO: 17 (VH CDR3), SEQ ID NO:27 (VL CDR1), SEQ ID NO:39 (VL CDR2), and SEQ ID NO: 51 (VL CDR3);

(g) B11: SEQ ID NO:3 (VH CDR1), SEQ ID NO:8 (VH CDR2), SEQ ID NO: 18 (VH CDR3), SEQ ID NO:30 (VL CDR1), SEQ ID NO:40 (VL CDR2), and SEQ ID NO: 52 (VL CDR3);

(h) C11: SEQ ID NO:4 (VH CDR1), SEQ ID NO:9 (VH CDR2), SEQ ID NO: 19 (VH CDR3), SEQ ID NO:31 (VL CDR1), SEQ ID NO:41 (VL CDR2), and SEQ ID NO: 53 (VL CDR3);

(i) C12: SEQ ID NO:3 (VH CDR1), SEQ ID NO:8 (VH CDR2), SEQ ID NO:20 (VH CDR3), SEQ ID NO:31 (VL CDR1), SEQ ID NO:41 (VL CDR2), and SEQ ID NO: 54 (VL CDR3);

(j) D12: SEQ ID NO:3 (VH CDR1), SEQ ID NO:8 (VH CDR2), SEQ ID NO:21 (VH CDR3), SEQ ID NO:32 (VL CDR1), SEQ ID NO:42 (VL CDR2), and SEQ ID NO: 55 (VL CDR3);

(k) E02: SEQ ID NO:3 (VH CDR1), SEQ ID NO:8 (VH CDR2), SEQ ID NO:22 (VH CDR3), SEQ ID NO:31 (VL CDR1), SEQ ID NO:43 (VL CDR2), and SEQ ID NO: 56 (VL CDR3);

(l) E03: SEQ ID NO:3 (VH CDR1), SEQ ID NO: 10 (VH CDR2), SEQ ID NO:23 (VH CDR3), SEQ ID NO:33 (VL CDR1), SEQ ID NO:44 (VL CDR2), and SEQ ID NO: 57 (VL CDR3);

(m) E05: SEQ ID NO:5 (VH CDR1), SEQ ID NO: 11 (VH CDR2), SEQ ID NO:24 (VH CDR3), SEQ ID NO:34 (VL CDR1), SEQ ID NO:45 (VL CDR2), and SEQ ID NO: 58 (VL CDR3);

(n) F04: SEQ ID NO:4 (VH CDR1), SEQ ID NO:9 (VH CDR2), SEQ ID NO:25 (VH CDR3), SEQ ID NO:35 (VL CDR1), SEQ ID NO:46 (VL CDR2), and SEQ ID NO: 59 (VL CDR3); and (O) G01: SEQ ID NO:3 (VH CDR1), SEQ ID NO:8 (VH CDR2), SEQ ID NO:26 (VH CDR3), SEQ ID NO:36 (VL CDR1), SEQ ID NO:47 (VL CDR2), and SEQ ID NO: 60 (VL CDR3).

11. The inhibitor according to claim 8, wherein said inhibitor reduces or inhibits the binding of IGFBP5 to at least one of its receptors and the at least one receptor is $\alpha 2\beta 1$ integrin or $\alpha v\beta 6$ integrin.

12. The inhibitor according to claim 1, comprising:

a heavy chain variable domain sequence of the amino acid sequence SEQ ID NO:66 and a light chain variable domain sequence of the amino acid sequence SEQ ID NO: 81.

13. An isolated polynucleotide comprising at least one sequence that encodes the inhibitor according to claim 1.

14. A method of treating and/or inhibiting fibrosis and/or a fibrotic condition, the method comprising administering a therapeutically effective amount of an inhibitor of IGFBP5 and/or of at least one of its receptors, wherein the inhibitor is an antibody or antigen binding fragment thereof having three heavy chain (VH) CDRs and three light chain (VL) CDRS, selected from the following:

(a) A09: SEQ ID NO:1 (VH CDR1), SEQ ID NO:6 (VH CDR2), SEQ ID NO: 12 (VH CDR3), SEQ ID NO:27 (VL CDR1), SEQ ID NO:37 (VL CDR2), and SEQ ID NO: 48 (VL CDR3);

(b) B06: SEQ ID NO:2 (VH CDR1), SEQ ID NO:7 (VH CDR2), SEQ ID NO: 13 (VH CDR3), SEQ ID NO:28 (VL CDR1), SEQ ID NO:38 (VL CDR2), and SEQ ID NO: 49 (VL CDR3);

(c) C02: SEQ ID NO:1 (VH CDR1), SEQ ID NO:6 (VH CDR2), SEQ ID NO: 14 (VH CDR3), SEQ ID NO:29 (VL CDR1), SEQ ID NO:38 (VL CDR2), and SEQ ID NO: 49 (VL CDR3);

(d) D10: SEQ ID: 1 (VH CDR1), SEQ ID NO:6 (VH CDR2), SEQ ID NO: 15 (VH CDR3), SEQ ID NO:27 (VL CDR1), SEQ ID NO:39 (VL CDR2), and SEQ ID NO: 50 (VL CDR3);

(e) F05: SEQ ID: 1 (VH CDR1), SEQ ID NO:6 (VH CDR2), SEQ ID NO: 16 (VH CDR3), SEQ ID NO:29 (VL CDR1), SEQ ID NO:38 (VL CDR2), and SEQ ID NO: 49 (VL CDR3);

(f) B09: SEQ ID: 1 (VH CDR1), SEQ ID NO:6 (VH CDR2), SEQ ID NO: 17 (VH CDR3), SEQ ID NO:27 (VL CDR1), SEQ ID NO:39 (VL CDR2), and SEQ ID NO: 51 (VL CDR3);

(g) B11: SEQ ID NO:3 (VH CDR1), SEQ ID NO:8 (VH CDR2), SEQ ID NO: 18 (VH CDR3), SEQ ID NO:30 (VL CDR1), SEQ ID NO:40 (VL CDR2), and SEQ ID NO: 52 (VL CDR3);

(h) C11: SEQ ID NO:4 (VH CDR1), SEQ ID NO:9 (VH CDR2), SEQ ID NO: 19 (VH CDR3), SEQ ID NO:31 (VL CDR1), SEQ ID NO:41 (VL CDR2), and SEQ ID NO: 53 (VL CDR3);

(i) C12: SEQ ID NO:3 (VH CDR1), SEQ ID NO:8 (VH CDR2), SEQ ID NO:20 (VH CDR3), SEQ ID NO:31 (VL CDR1), SEQ ID NO:41 (VL CDR2), and SEQ ID NO: 54 (VL CDR3);

(j) D12: SEQ ID NO:3 (VH CDR1), SEQ ID NO:8 (VH CDR2), SEQ ID NO:21 (VH CDR3), SEQ ID NO:32 (VL CDR1), SEQ ID NO:42 (VL CDR2), and SEQ ID NO: 55 (VL CDR3);

(k) E02: SEQ ID NO:3 (VH CDR1), SEQ ID NO:8 (VH CDR2), SEQ ID NO:22 (VH CDR3), SEQ ID NO:31 (VL CDR1), SEQ ID NO:43 (VL CDR2), and SEQ ID NO: 56 (VL CDR3);

(l) E03: SEQ ID NO:3 (VH CDR1), SEQ ID NO: 10 (VH CDR2), SEQ ID NO:23 (VH CDR3), SEQ ID NO:33 (VL CDR1), SEQ ID NO:44 (VL CDR2), and SEQ ID NO: 57 (VL CDR3);

(m) E05: SEQ ID NO:5 (VH CDR1), SEQ ID NO: 11 (VH CDR2), SEQ ID NO:24 (VH CDR3), SEQ ID NO:34 (VL CDR1), SEQ ID NO:45 (VL CDR2), and SEQ ID NO: 58 (VL CDR3);

(n) F04: SEQ ID NO:4 (VH CDR1), SEQ ID NO:9 (VH CDR2), SEQ ID NO:25 (VH CDR3), SEQ ID NO:35 (VL CDR1), SEQ ID NO:46 (VL CDR2), and SEQ ID NO: 59 (VL CDR3); and (O) G01: SEQ ID NO:3 (VH CDR1), SEQ ID NO:8 (VH CDR2), SEQ ID NO:26 (VH CDR3), SEQ ID NO:36 (VL CDR1), SEQ ID NO:47 (VL CDR2), and SEQ ID NO: 60 (VL CDR3).

15. The method according to claim 14, wherein fibrosis or of a fibrotic condition is scleroderma or pulmonary fibrosis, morphea, fibrosis as a result of Graft-Versus-Host Disease (GVHD), keloid and hypertrophic scar, subepithelial fibrosis, endomyocardial fibrosis, uterine fibrosis, myelofibrosis, retroperitoneal fibrosis, nephrogenic systemic fibrosis, scarring after surgery, asthma, aberrant wound healing, multifocal fibrosclerosis, cryptogenic fibrosing alveolitis (CFA), and idiopathic pulmonary fibrosis (IPF).

* * * * *